US011439359B2

(12) United States Patent
Sugihara et al.

(10) Patent No.: US 11,439,359 B2
(45) Date of Patent: Sep. 13, 2022

(54) X-RAY CT IMAGING APPARATUS AND METHOD OF CONTROLLING X-RAY CT IMAGING APPARATUS

(71) Applicant: J. MORITA MANUFACTURING CORPORATION, Kyoto (JP)

(72) Inventors: Yoshito Sugihara, Kyoto (JP); Tomoyuki Sadakane, Kyoto (JP); Masanori Otsuka, Kyoto (JP); Takahiro Yoshimura, Kyoto (JP); Yutaka Ito, Kyoto (JP); Sho Matsushita, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 71 days.

(21) Appl. No.: 17/050,454

(22) PCT Filed: Apr. 25, 2019

(86) PCT No.: PCT/JP2019/017564
§ 371 (c)(1),
(2) Date: Oct. 26, 2020

(87) PCT Pub. No.: WO2019/208679
PCT Pub. Date: Oct. 31, 2019

(65) Prior Publication Data
US 2021/0228166 A1 Jul. 29, 2021

(30) Foreign Application Priority Data

Apr. 27, 2018 (JP) .............................. JP2018-086455

(51) Int. Cl.
*A61B 6/14* (2006.01)
*A61B 6/03* (2006.01)
*A61B 6/00* (2006.01)

(52) U.S. Cl.
CPC ............... *A61B 6/14* (2013.01); *A61B 6/032* (2013.01); *A61B 6/42* (2013.01); *A61B 6/4452* (2013.01); *A61B 6/4476* (2013.01); *A61B 6/54* (2013.01)

(58) Field of Classification Search
CPC .. A61B 6/54; A61B 6/035; A61B 6/52; A61B 6/4441; A61B 6/4476; A61B 6/14; A61B 6/032; A61B 6/42; A61B 6/4452
See application file for complete search history.

(56) References Cited

U.S. PATENT DOCUMENTS

2005/0117693 A1   6/2005  Miyano
2007/0041491 A1   2/2007  Sadakane et al.
(Continued)

FOREIGN PATENT DOCUMENTS

JP   2002-219127 A   8/2002
JP   2007-029168 A   2/2007
(Continued)

OTHER PUBLICATIONS

The Preliminary Report on Patentability (with Written Opinion) from the corresponding International Patent Application No. PCT/JP2019/017564 dated Oct. 27, 2020.
(Continued)

*Primary Examiner* — Don K Wong
(74) *Attorney, Agent, or Firm* — Shinjyu Global IP

(57) ABSTRACT

An object of the present invention is to prevent an X-ray generator and an X-ray detector that turn around a subject from contacting with the subject. An X-ray CT imaging apparatus includes a turning support that supports an X-ray generator and an X-ray detector, a turning drive mechanism including a turning mechanism and a turning axis moving mechanism, an imaging region position setting unit that receives a setting of a position of an imaging region to a
(Continued)

local part of a dental arch of a head, and a turning controller. The position of the mechanical turning axis X1 is controlled according to the position of the imaging region set by the imaging region position setting unit.

15 Claims, 25 Drawing Sheets

(56) References Cited

U.S. PATENT DOCUMENTS

| | | | |
|---|---|---|---|
| 2011/0222646 A1 | 9/2011 | Suzuki et al. | |
| 2012/0307960 A1 | 12/2012 | Choi et al. | |
| 2021/0093282 A1* | 4/2021 | Sadakane | ............... A61B 6/588 |

FOREIGN PATENT DOCUMENTS

| | | |
|---|---|---|
| JP | 2010-046360 A | 3/2010 |
| JP | 2011-206534 A | 10/2011 |
| JP | 2014-138911 A | 7/2014 |
| JP | 2015-177964 A | 10/2015 |

OTHER PUBLICATIONS

The Search Report from the corresponding International Patent Application No. PCT/JP2019/017564 dated Jul. 16, 2019.
The Office Action from the corresponding Japanese Patent Application No. 2018-086455 dated Sep. 23, 2020.
The Search Report from the corresponding European Patent Application No. 19792072.1 dated Nov. 17, 2021.

* cited by examiner

F I G. 4
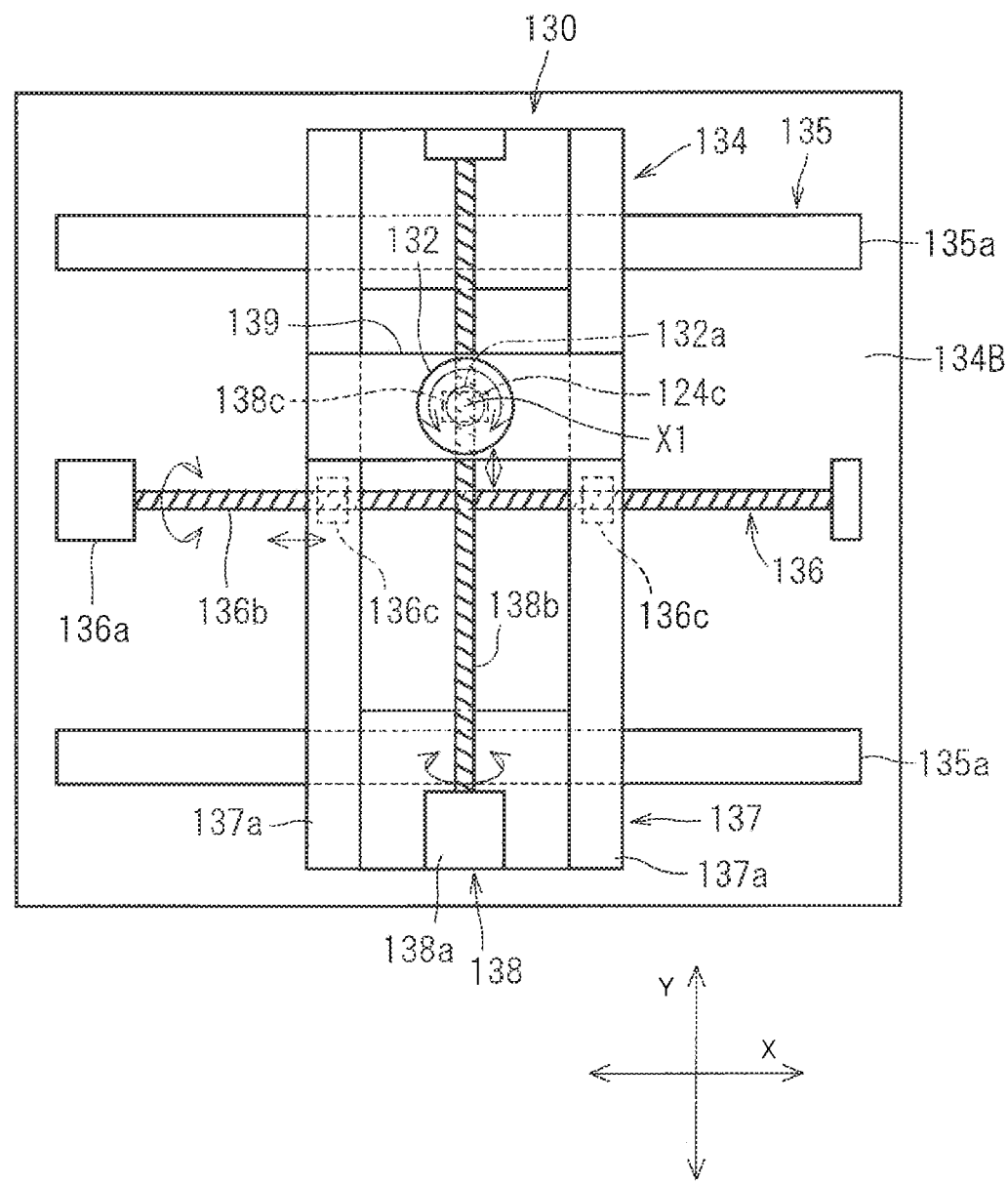

F I G . 9

| POSITION OF IMAGING REGION | TURNING CONTROL CONTENT | SEPARATION DISTANCE (MAGNIFICATION) | REGULATION WIDTH |
|---|---|---|---|
| FRONT TOOTH | TURNING WITH RADIUS r ABOUT CENTER A | D(1) m(1) | w(1) |
| MOLAR TOOTH | TURNING WITH TURNING AXIS X1 MATCHED WITH CENTER A | D(2) m(2) | w(2) |

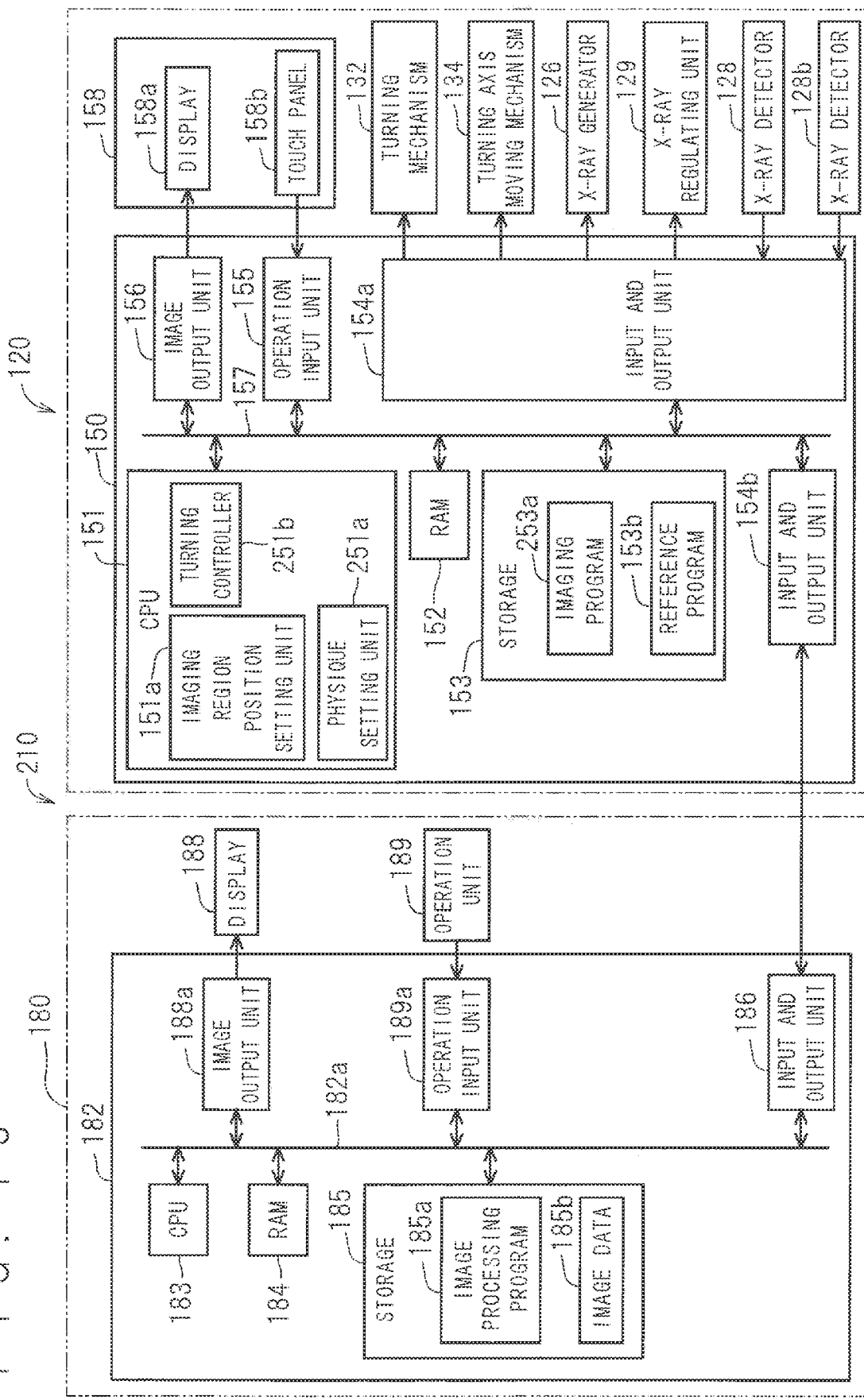

F I G . 1 7
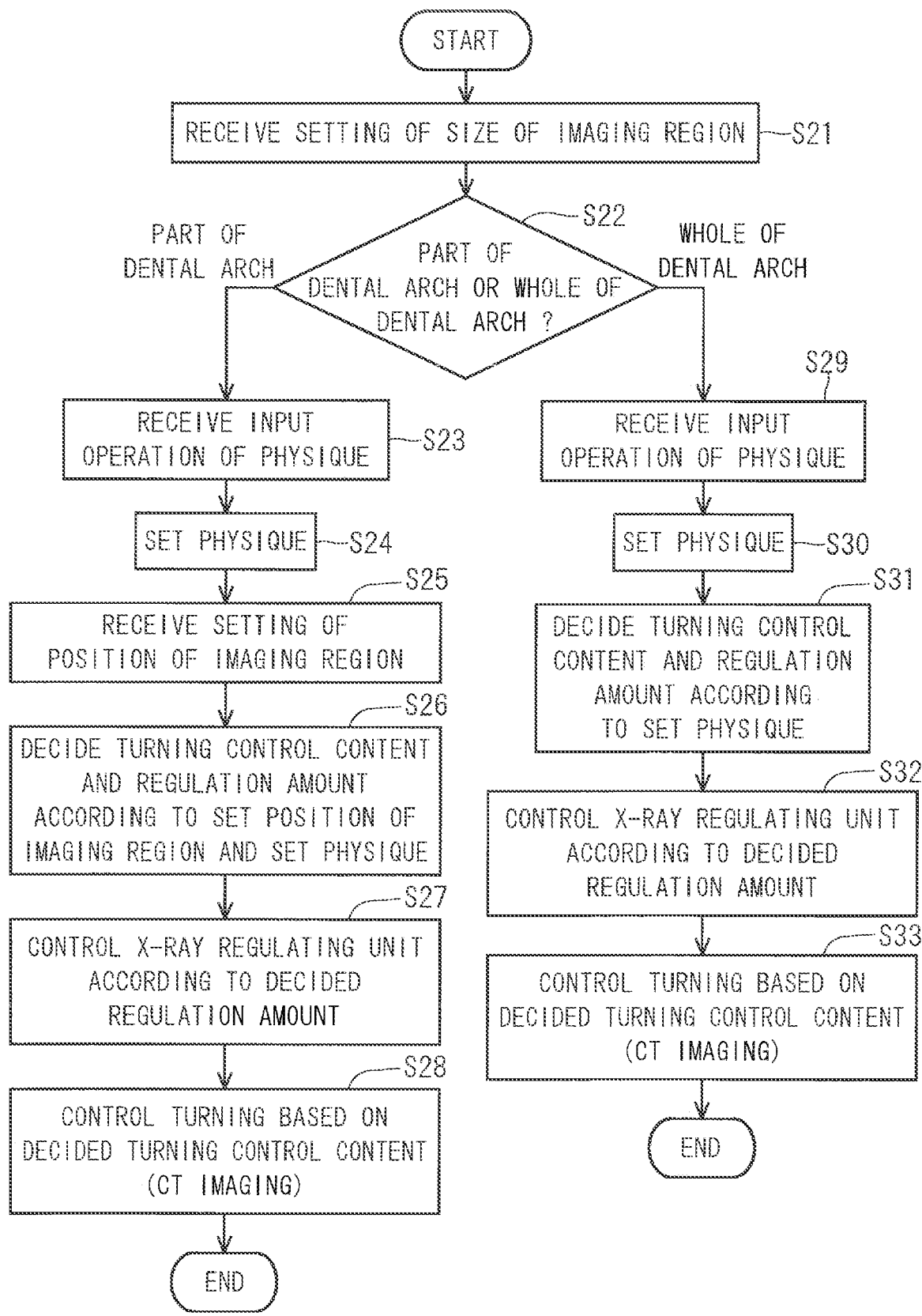

FIG. 20

| PHYSIQUE | POSITION OF IMAGING REGION | TURNING CONTROL CONTENT | SEPARATION DISTANCE (MAGNIFICATION) | REGULATION WIDTH |
|---|---|---|---|---|
| P (M) | FRONT TOOTH | TURNING WITH RADIUS r (M1) ABOUT CENTER A | D (M1) m (M1) | W (M1) |
| P (M) | MOLAR TOOTH | TURNING WITH TURNING AXIS X1 MATCHED WITH CENTER A | D (M2) m (M2) | W (M2) |
| P (L) | FRONT TOOTH | TURNING WITH RADIUS r (L1) ABOUT CENTER A | D (L1) m (L1) | W (L1) |
| P (L) | MOLAR TOOTH | TURNING WITH RADIUS r (L2) ABOUT CENTER A | D (L2) m (L2) | W (L2) |

FIG. 21

| PHYSIQUE | TURNING CONTROL CONTENT | SEPARATION DISTANCE (MAGNIFICATION) | REGULATION WIDTH |
|---|---|---|---|
| P (M) | TURNING WITH TURNING AXIS X1 MATCHED WITH CENTER A | D (M) m (M) | w (M) |
| P (L) | TURNING WITH RADIUS r ABOUT CENTER A | D (L) m (L) | w (L) |

F I G . 2 3
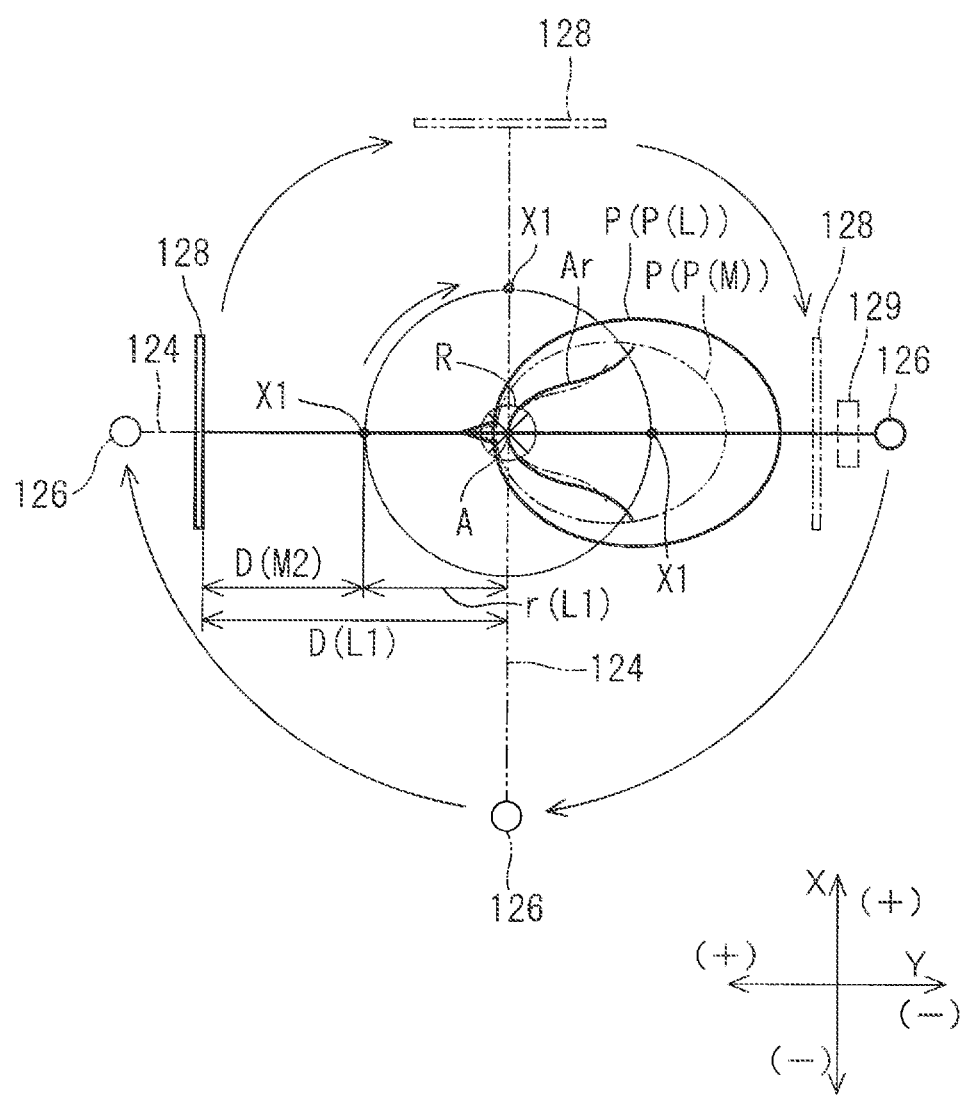

X-RAY CT IMAGING APPARATUS AND METHOD OF CONTROLLING X-RAY CT IMAGING APPARATUS

CROSS-REFERENCE TO RELATED APPLICATIONS

This application is the U.S. National Phase of International Application No. PCT/JP2019/017564, filed Apr. 25, 2019. That application claims priority to Japanese Patent Application No. 2018-086455, filed Apr. 27, 2018. Both of those applications are incorporated by reference herein in their entireties.

TECHNICAL FIELD

The present invention relates to an X-ray CT imaging apparatus that performs X-ray imaging by rotating an X-ray generator and an X-ray detector around a subject.

BACKGROUND

Japanese Patent Application Laid-Open No. 2007-029168 discloses an X-ray CT imaging apparatus including a turning mechanism and a moving mechanism. The turning mechanism turns turning means, in which the X-ray generator and the X-ray detector are disposed opposite to each other while the subject is sandwiched therebetween, around a turning axis. The moving mechanism moves the turning axis and/or the subject in a plane perpendicular to the turning axis. In the X-ray CT imaging apparatus, the turning means is turned by combined motion of the turning of the turning unit and the turning axis and/or the movement of the subject while a center of a region of interest of the subject is always set to a rotation center on the imaging different from the turning axis of the turning mechanism. Consequently, a magnification ratio can be changed by relatively changing a distance between the X-ray generator and the rotation center and/or a distance between the X-ray detector and the rotation center.

BRIEF SUMMARY

By the way, in performing the X-ray CT imaging, there are various positions of an imaging region in the subject.

In Japanese Patent Application Laid-Open No. 2007-029168, the X-ray generator and the X-ray detector, which turn about the subject, possibly contact with the subject because the position of the imaging region in the subject is not taken into consideration.

An object of the present invention is to prevent the X-ray generator and the X-ray detector that turn around the subject from contacting with the subject.

In order to solve the above problem, according to a first aspect of the present invention, an X-ray CT imaging apparatus includes: a turning support that supports an X-ray generator and an X-ray detector such that the X-ray generator and the X-ray detector are opposed to each other with a subject sandwiched therebetween; a turning drive mechanism including a turning mechanism that turns the turning support about a mechanical turning axis located between the X-ray generator and the X-ray detector and a turning axis moving mechanism that moves the mechanical turning axis in a direction intersecting with an axial direction of the mechanical turning axis; an imaging region position setting unit that receives a setting a position of an X-ray CT imaging region with respect to a local part of a dental arch of a head of the subject; and a turning controller that controls the turning mechanism and the turning axis moving mechanism. The turning axis moving mechanism moves the mechanical turning axis in synchronization with turning of the turning support about the mechanical turning axis using the turning mechanism, and the turning support is caused to perform combined motion, which allows the X-ray generator and the X-ray detector to turn about the X-ray CT imaging region, and a position of the mechanical turning axis is controlled according to the position of the X-ray CT imaging region set by the imaging region position setting unit.

According to a second aspect that is the X-ray CT imaging apparatus of the first aspect, when X-ray CT imaging is performed on a molar tooth of the dental arch as the X-ray CT imaging region, the position of the mechanical turning axis is controlled such that the X-ray detector passes through a trajectory closer to a center of the X-ray CT imaging region than the X-ray detector during the performance of the X-ray CT imaging on a front tooth of the dental arch as the X-ray CT imaging region.

According to a third aspect that is the X-ray CT imaging apparatus of the first or second aspect, drive control in which the turning support is caused to perform the combined motion and drive control in which the turning support is turned while the mechanical turning axis is fixed to the position of the center of the X-ray CT imaging region are switched according to the position of the X-ray CT imaging region set by the imaging region position setting unit.

According to a fourth aspect that is the X-ray CT imaging apparatus of the third aspect, drive control in which the turning support is caused to perform the combined motion when X-ray CT imaging is performed on a front tooth of the dental arch as the X-ray CT imaging region, and drive control in which the turning support is turned while the mechanical turning axis is fixed to the position of the center of the X-ray CT imaging region when X-ray CT imaging is performed on a molar tooth of the dental arch as the X-ray CT imaging region.

According to a fifth aspect that is the X-ray CT imaging apparatus of any one of the first to fourth aspects, a distance between the mechanical turning axis and the center of the X-ray CT imaging region is changed according to the position of the X-ray CT imaging region set by the imaging region position setting unit when the turning support is caused to perform the combined motion.

According to a sixth aspect that is the X-ray CT imaging apparatus of the first aspect, when X-ray CT imaging is performed on a local part of the dental arch according to the position of the X-ray CT imaging region set by the imaging region position setting unit, the position of the mechanical turning axis with respect to the center of the X-ray CT imaging region is changed such that a separation distance is larger than a maximum distance on assumption that smaller one of a distance between the center of the X-ray CT imaging region and the X-ray generator and a distance between the center of the X-ray CT imaging region and the X-ray detector is set to the separation distance, and that the maximum distance between a surface of the head and the center of the X-ray CT imaging region is set in a turning range of the X-ray generator or the X-ray detector closer to the center of the X-ray CT imaging region.

According to a seventh aspect that is the X-ray CT imaging apparatus of the sixth aspect, the imaging region position setting unit can receive a first imaging region and a second imaging region where the maximum distance is smaller than the maximum distance of the first imaging region as the X-ray CT imaging region, and according to the position of the X-ray CT imaging region set by the imaging region position setting unit, the position of the mechanical turning axis with respect to the center of the X-ray CT imaging region is changed such that the separation distance when the X-ray CT imaging region is the first imaging region is larger than the separation distance when the X-ray CT imaging region is the second imaging region.

According to an eighth aspect that is the X-ray CT imaging apparatus of the seventh aspect, drive control in which the turning support is caused to perform the combined motion is performed when the X-ray CT imaging region is the first imaging region, and drive control in which the turning support is turned while the mechanical turning axis is fixed to the position of the center of the X-ray CT imaging region is performed when the X-ray CT imaging region is the second imaging region.

According to a ninth aspect that is the X-ray CT imaging apparatus of any one of the first to eighth aspects, the mechanical turning axis is set at a position closer to the X-ray detector than the X-ray generator.

According to a tenth aspect, the X-ray CT imaging apparatus of any one of the first to ninth aspects further includes a subject physique setting unit capable of setting a first physique and a second physique smaller than the first physique as a setting of a size of the physique of the subject. The position of the mechanical turning axis is controlled according to the size of the physique of the subject set by the subject physique setting unit.

According to an eleventh aspect that is the X-ray CT imaging apparatus of the tenth aspect, drive control in which the turning support is caused to perform the combined motion and drive control in which the turning support is turned while the mechanical turning axis is fixed to a position of the center of the X-ray CT imaging region are switched according to the size of the physique of the subject set by the subject physique setting unit.

According to a twelfth aspect that is the X-ray CT imaging apparatus of the tenth or eleventh aspect, a distance of the mechanical turning axis to the center of the X-ray CT imaging region is changed according to the size of the physique of the subject set by the subject physique setting unit when the turning support is caused to perform the combined motion.

According to a thirteenth aspect that is the X-ray CT imaging apparatus of any one of the first to twelfth aspects, when the turning support is caused to perform the combined motion, the turning axis moving mechanism rotates the mechanical turning axis about the center of the X-ray CT imaging region in synchronization with the turning of the turning support about the mechanical turning axis using the turning mechanism.

According to a fourteenth aspect that is the X-ray CT imaging apparatus of any one of the first to thirteenth aspects, the distance of the X-ray generator to the center of the X-ray CT imaging region and the distance of the X-ray detector to the center of the X-ray CT imaging region are kept constant while the X-ray CT imaging is performed by irradiating the subject with the X-ray generated from the X-ray generator.

According to a fifteenth aspect, a method of controlling an X-ray CT imaging apparatus including: a turning support that supports an X-ray generator and an X-ray detector so that the X-ray generator and the X-ray detector are opposed to each other with a subject sandwiched therebetween; a turning drive mechanism including a turning mechanism that turns the turning support about a mechanical turning axis located between the X-ray generator and the X-ray detector and a turning axis moving mechanism that moves the mechanical turning axis in a direction intersecting with an axial direction of the mechanical turning axis; and a turning controller that controls the turning mechanism and the turning axis moving mechanism, the method includes: turning the turning support about the mechanical turning axis using the turning mechanism in synchronization with movement of the mechanical turning axis using the turning axis moving mechanism, and causing the turning support to perform combined motion, which allows the X-ray generator and the X-ray detector to turn about an X-ray CT imaging region; and controlling a position of the mechanical turning axis according to a setting of the position of the X-ray CT imaging region to a local part of a dental arch of a head of the subject.

Effects of the Invention

According to the first aspect, since the position of the mechanical turning axis is controlled according to the position of the X-ray CT imaging region set by the imaging region position setting unit, the trajectories of the X-ray generator and the X-ray detector can be controlled according to the position of the mechanical turning axis, and the X-ray generator and the X-ray detector, which turn about the subject, can be prevented from contacting with the subject.

The head is usually long in the front-back direction. For this reason, when the X-ray CT imaging is performed on the front tooth of the dental arch as the X-ray CT imaging region, the distance between the front tooth and the rear portion of the head is lengthened, and the X-ray generator or the X-ray detector contacts easily with the head. On the other hand, when the X-ray CT imaging is performed on the molar tooth of the dental arch as the X-ray CT imaging region, the distance between the molar tooth and the side or rear portion of the head is relatively shortened. Consequently, as in the second aspect, during the performance of the X-ray CT imaging on the molar tooth of the dental arch as the X-ray CT imaging region, when the position of the mechanical turning axis is controlled such that the X-ray detector passes through the trajectory closer to the center of the X-ray CT imaging region than the X-ray detector during the performance of the X-ray CT imaging on the front tooth of the dental arch as the X-ray CT imaging region, the X-ray generator and the X-ray detector, which turn about the subject, can be prevented from contacting with the subject.

According to the third aspect, the drive control in which the turning support is caused to perform the combined motion and the drive control in which the turning support is turned while the mechanical turning axis is fixed to the position of the center of the X-ray CT imaging region are switched according to the position of the X-ray CT imaging region set by the imaging region position setting unit. Thus, the trajectories of the X-ray generator and the X-ray detector can be controlled according to the position, and the X-ray generator and the X-ray detector, which turn about the subject, can be prevented from contacting with the subject.

According to the fourth aspect, the drive control in which the turning support is caused to perform the combined motion when the X-ray CT imaging is performed on the front tooth of the dental arch as the X-ray CT imaging region, and the drive control in which the turning support is turned while the mechanical turning axis is fixed to the position of the center of the X-ray CT imaging region is performed when the X-ray CT imaging is performed on the molar tooth of the dental arch as the X-ray CT imaging region. Thus, the trajectories of the X-ray generator and the X-ray detector can be controlled according to the position of the X-ray CT imaging region, and the X-ray generator and the X-ray detector, which turn about the subject, can be prevented from contacting with the subject.

According to the fifth aspect, when the turning support is caused to perform the combined motion, the distance between the center of the X-ray CT imaging region and the mechanical turning axis is changed according to the position of the X-ray CT imaging region set by the imaging region position setting unit. Thus, the trajectories of the X-ray generator and the X-ray detector can be controlled according to the position of the X-ray CT imaging region, and the X-ray generator and the X-ray detector, which turn about the subject, can be prevented from contacting with the subject.

According to the sixth aspect, when the X-ray CT imaging is performed on the local part of the dental arch according to the position of the X-ray CT imaging region set by the imaging region position setting unit, the position of the mechanical turning axis with respect to the center of the X-ray CT imaging region is changed such that the separation distance is larger than the maximum distance on assumption that smaller one of the distance between the center of the X-ray CT imaging region and the X-ray generator and the distance between the center of the X-ray CT imaging region and the X-ray detector is set to the separation distance, and that the maximum distance between the surface of the head and the center of the X-ray CT imaging region is set in the turning range of the X-ray generator or the X-ray detector closer to the center of the X-ray CT imaging region, so that the X-ray generator and the X-ray detector, which turn about the subject, can be prevented from contacting with the subject.

According to the seventh aspect, the position of the mechanical turning axis with respect to the center of the X-ray CT imaging region is changed such that the separation distance when the X-ray CT imaging region is the first imaging region is larger than the separation distance when the X-ray CT imaging region is the second imaging region where the maximum distance is smaller than the maximum distance of the first imaging region according to the set position of the X-ray CT imaging region, so that the X-ray generator and the X-ray detector can be prevented from contacting with the subject.

According to the eighth aspect, the drive control in which the turning support is caused to perform the combined motion is performed when the X-ray CT imaging region is the first imaging region, and the drive control in which the turning support is turned while the mechanical turning axis is fixed to the position of the center of the X-ray CT imaging region when the X-ray CT imaging region is the second imaging region, so that the X-ray generator and X-ray detector can be prevented from contacting with the subject.

According to the ninth aspect, since the X-ray detector turns near the X-ray CT imaging region, the X-ray CT image can be made clear as much as possible.

According to the tenth aspect, the position of the mechanical turning axis is controlled according to the size of the physique of the subject set in the subject physique setting unit. Thus, the trajectories of the X-ray generator and the X-ray detector can be controlled according to the size of the physique of the subject, and the X-ray generator and the X-ray detector, which turn about the subject, can be prevented from contacting with the subject.

In the eleventh aspect, the drive control in which the turning support is caused to perform the combined motion and the drive control in which the turning support is turned while the mechanical turning axis is fixed to the position of the center of the X-ray CT imaging region can be changed according to the size of the physique of the subject set by the subject physique setting unit, so that the X-ray generator and the X-ray detector, which turn about the subject, can be prevented from contacting with the subject.

In the twelfth aspect, the distance between the mechanical turning axis and the center of the X-ray CT imaging region is changed according to the size of the physique of the subject set by the subject physique setting unit when the turning support is caused to perform the combined motion, so that the X-ray generator and the X-ray detector, which turn about the subject, can be prevented from contacting with the subject.

In the thirteenth aspect, when the turning support is caused to perform the combined motion, the turning axis moving mechanism rotates the mechanical turning axis about the center of the X-ray CT imaging region in synchronization with the turning of the turning support about the mechanical turning axis using the turning mechanism, so that the X-ray generator and the X-ray detector can be turned along the orbit as close as possible to the circle even when the mechanical turning axis is moved during the performance of the X-ray CT imaging.

In the fourteenth aspect, the X-ray CT imaging can be performed while the magnification ratio is kept constant.

According to the fifteenth aspect, the position of the mechanical turning axis is controlled according to the position setting of the X-ray CT imaging region with respect to the local part of the dental arch of the head of the subject. Thus, the trajectories of the X-ray detector and the X-ray detector can be controlled according to the position, and the X-ray generator and the X-ray detector, which turn about the subject, can be prevented from contacting with the subject.

BRIEF DESCRIPTION OF THE DRAWINGS

FIG. 4 is a schematic bottom view illustrating a turning drive mechanism.

FIG. 9 is a view illustrating an example of a reference table.

FIG. 16 is a block diagram illustrating an electric configuration of an X-ray CT imaging apparatus according to a third embodiment.

FIG. 17 is a flowchart illustrating processing of an imaging program.

FIG. 20 is a view illustrating an example of a reference table.

FIG. 21 is a view illustrating an example of the reference table.

FIG. 23 is a view illustrating an example of the turning operation.

DETAILED DESCRIPTION

First Embodiment

Figure 1:
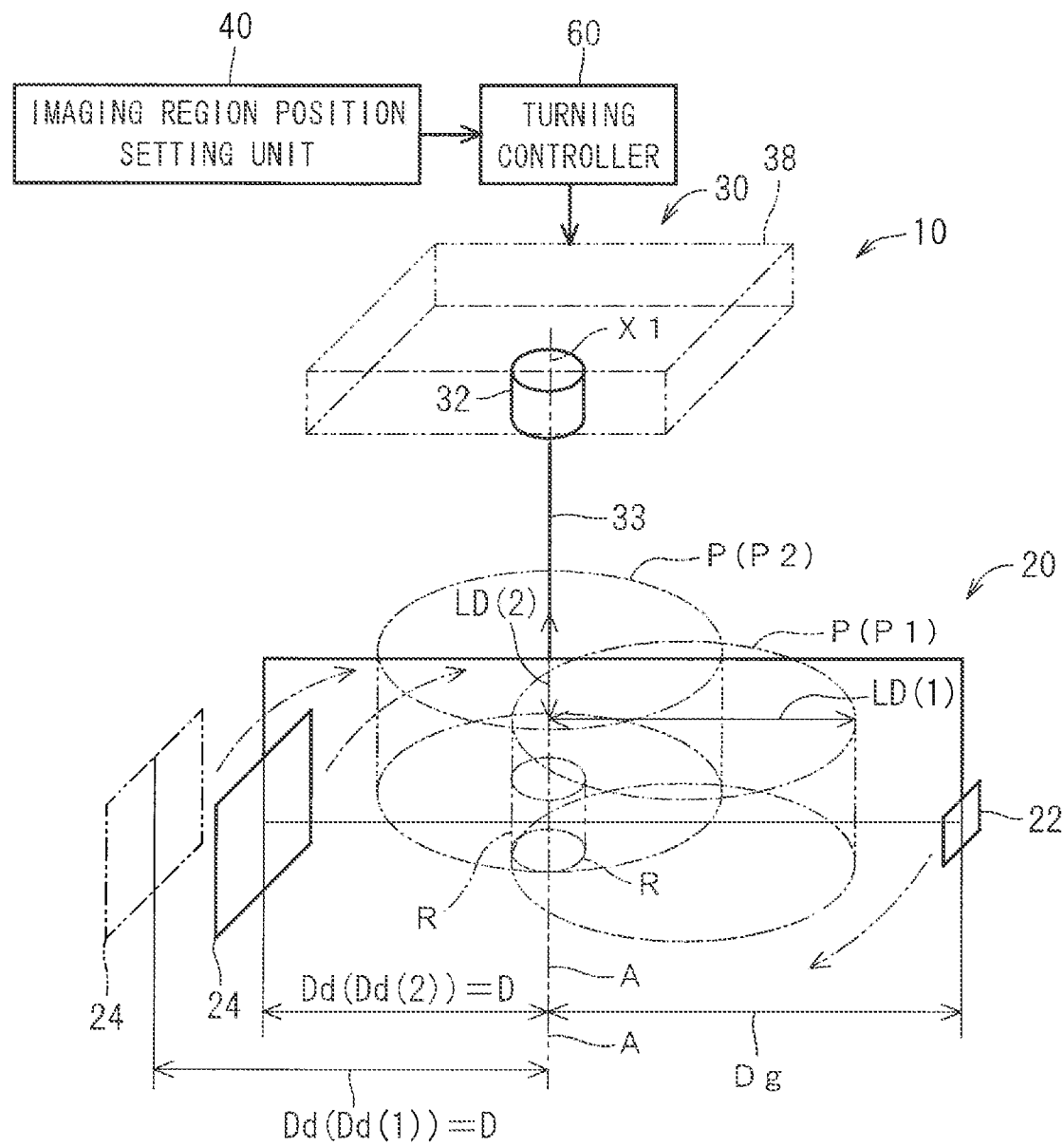
FIG. 1 is a schematic diagram illustrating an X-ray CT imaging apparatus according to a first embodiment.

A medical X-ray CT imaging apparatus according to an embodiment and a control method thereof will be described below. FIG. 1 is a schematic diagram illustrating an X-ray CT imaging apparatus 10.

The X-ray CT imaging apparatus 10 is an apparatus that performs X-ray computed tomography (CT) imaging of a head P of a subject, and includes a turning support 20, a turning drive mechanism 30, an imaging region position setting unit 40, and a turning controller 60.

The turning support 20 supports an X-ray generator 22 and an X-ray detector 24 such that the X-ray generator 22 and the X-ray detector 24 are opposed to each other with the head P of the subject interposed therebetween. The X-ray generator 22 generates an X-ray (X-ray beam). The X-ray detector 24 detects the X-ray emitted from the X-ray generator 22. The X-ray generator 22 and the X-ray detector 24 are supported by the turning support 20 with a space where the head P can be disposed between the X-ray generator 22 and the X-ray detector 24. The X-ray emitted from the X-ray generator 22 is incident on the X-ray detector 24 through the head P. The X-ray incident on the X-ray detector 24 is converted into an electric signal corresponding to intensity of the X-ray in each unit pixel. The X-ray CT image or the like is generated based on each electric signal.

The turning drive mechanism 30 includes a turning mechanism 32 and a turning axis moving mechanism 38.

The turning mechanism 32 turns the turning support 20 about a mechanical turning axis X1 located between the X-ray generator 22 and the X-ray detector 24. For example, the turning mechanism 32 includes an electric motor, and includes an acceleration and deceleration mechanism such as a gear as necessary. The turning mechanism 32 rotatably supports a shaft 33 protruding from the turning support 20 at a position between the X-ray generator 22 and the X-ray detector 24. A center axis of the shaft 33 constitutes the mechanical turning axis X1. The turning support 20 turns about the mechanical turning axis X1 by driving the turning mechanism 32. The turning mechanism 32 may have any configuration as long as the turning mechanism 32 turns the turning support 20 about the mechanical turning axis X1.

The turning axis moving mechanism 38 moves the mechanical turning axis X1 in a direction intersecting with the mechanical turning axis X1. For example, the turning axis moving mechanism 38 is constructed with an XY-stage mechanism and the like. The XY-stage mechanism is a combination of two sets of linear actuators with moving directions of the linear actuators intersecting with each other. As the linear actuator, a linear moving mechanism in which a linear guide and a ball screw feed mechanism are combined, a linear motor, and an air cylinder can be used. The moving direction of each of the two sets of linear actuators of the XY-stage mechanism is set to intersect with the mechanical turning axis X1, and the turning mechanism 32 is supported so as to be able to be moved in the moving direction of each of the two sets of linear actuators. Consequently, the turning mechanism 32 can be moved along a plane intersecting with the mechanical turning axis X1, and therefore the mechanical turning axis X1 can be moved along the plane intersecting with the mechanical turning axis X1.

The turning axis moving mechanism 38 is not limited to the above example, but any turning axis moving mechanism that moves the mechanical turning axis X1 in the direction intersecting with the mechanical turning axis X1 may be used.

When performing X-ray CT imaging by irradiating the subject P with the X-ray generated from the X-ray generator 22, the X-ray CT imaging apparatus 10 can turn the X-ray generator 22 and the X-ray detector 24 about the center of an X-ray CT imaging region R. In synchronization with the turning of the turning support 20 about the mechanical turning axis X1 using the turning mechanism 32, the turning axis moving mechanism 38 moves the mechanical turning axis X1, and causes the turning support 20 to perform combined motion, thereby performing the turning of the X-ray generator 22 and the X-ray detector 24. The case that the X-ray generator 22 and the X-ray detector 24 are turned around a center A of the imaging region R includes the case that the X-ray generator 22 and the X-ray detector 24 are turned while drawing a circular trajectory around the center A and the case that the X-ray generator 22 and the X-ray detector 24 are turned while drawing a trajectory other than a circle.

The imaging region position setting unit 40 is configured to be able to receive the setting of the position of the X-ray CT imaging region R (hereinafter, sometimes simply referred to as the imaging region R) with respect to a local part of the dental arch of the head P. At least the local part of the dental arch is included as a target region of the X-ray CT imaging, but the imaging region R may be set so as to include not only the local part of the dental arch but also a jaw joint region. That is, since a jaw bone region is set to a target of the X-ray CT imaging, the position of the imaging region R may be assigned so as to include the jaw bone region in addition to the local part of the dental arch. For example, the setting of the position of the imaging region R can be performed by assigning a schematic dental arch image through a pointing device such as a touch panel and a mouse. The dental arch image may be based on an actually captured X-ray image. The dental arch image may be a planar image of the dental arch or a front or side image of the dental arch. The position may be assigned through a direction key. Additionally, the position of the imaging region R may be set by assigning or selecting one or a plurality of dental formulas. The dental formula is a formula in which each tooth is distinguished by a number or the like. The dental formula may be a Japanese type dental formula, an FDI type (two-digit system) type dental formula, or an American type (Universal system) type dental formula. An operator performs the above setting. The imaging region position setting unit 40 sets the position of the imaging region R with respect to the turning controller 60 based on the received position setting of the imaging region R.

Examples of the position setting of the imaging region R with respect to the dental arch include a one-side molar region that is the local part of the dental arch and a front tooth region that is the local part of the dental arch. In FIG. 1, the head P is illustrated as a head P1 when the front tooth region is set as the imaging region R, and the head P is illustrated as a head P2 when the molar region is set as the imaging region R. The imaging region position setting unit may be any interface that receives the setting of the position of the imaging region on a plane orthogonal to the mechanical turning axis X1.

The turning controller 60 controls the turning mechanism 32 and the turning axis moving mechanism 38. In particular, the turning controller 60 controls the position of the turning axis X1 according to the position of the imaging region R set by the imaging region position setting unit 40.

The turning controller 60 includes at least one processor. For example, the turning controller 60 is constructed with a computer including at least one processor, a Random Access Memory (RAM), a storage, and an input and output unit. The storage is constructed with a nonvolatile storage device such as a flash memory or a hard disk drive, and stores a turning control program in controlling the turning mechanism 32 and the turning axis moving mechanism 38. The RAM serves as a work area when at least one processor performs predetermined processing. The input and output unit is connected to the turning mechanism 32, the turning axis moving mechanism 38, the imaging region position setting unit 40, and the like. At least one processor performs predetermined arithmetic processing according to the turning control program stored in the storage, and controls the turning mechanism 32 and the turning axis moving mechanism 38 according to the set position of the imaging region R.

Figure 2:
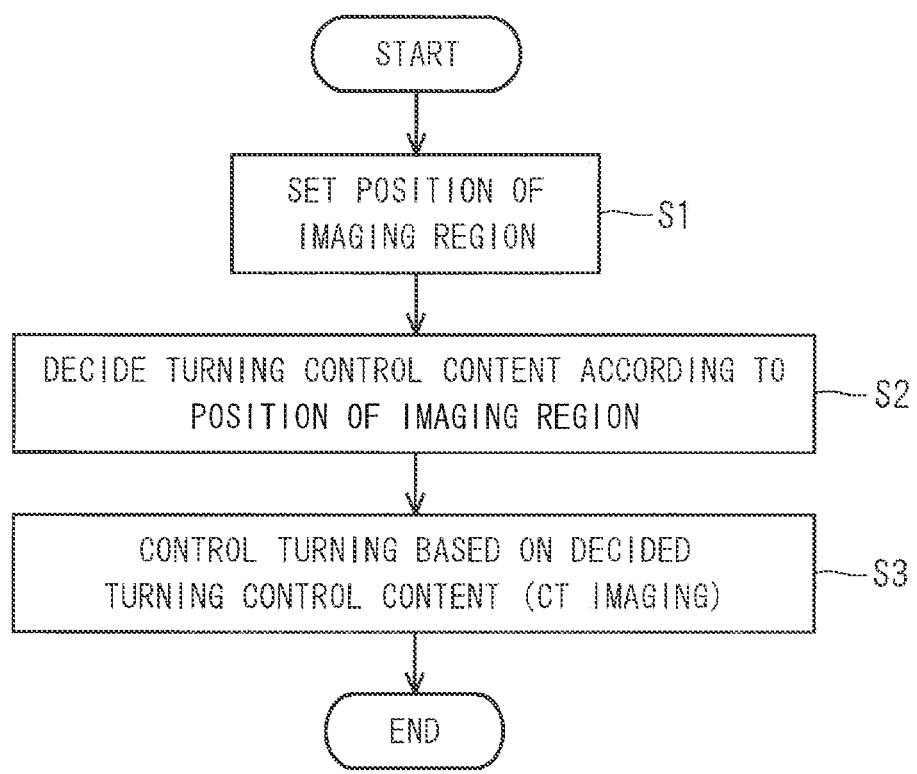
FIG. 2 is a flowchart illustrating an example of processing performed by a turning controller.

FIG. 2 is a flowchart illustrating processing performed by the turning controller 60.

That is, in performing the X-ray CT imaging, the position of the imaging region R is set through the imaging region position setting unit 40 in step S1.

Subsequently, in step S2, turning control content is determined according to the position setting of the imaging region R.

The turning control content includes information about the position control such as how to control the position of the mechanical turning axis X1 during the turning of the X-ray generator 22 and the X-ray detector 24 about the center of the imaging region R. The following example can be considered as an example of the position control of the mechanical turning axis X1. In the first position control example, the turning axis moving mechanism 38 moves the mechanical turning axis X1 in synchronization with the turning of the turning support 20 about the mechanical turning axis X1 using the turning mechanism 32. In this case, the turning axis moving mechanism 38 may turn the mechanical turning axis X1 about the imaging region R in synchronization with the turning of the turning support 20 about the mechanical turning axis X1 using the turning mechanism 32. At this point, the turning axis moving mechanism 38 may rotate the mechanical turning axis X1 with the center A of the imaging region R as a rotation center. In the second position control example, the mechanical turning axis X1 is fixed to the position of the center A of the imaging region R when the turning mechanism 32 turns the turning support 20 about the mechanical turning axis X1.

By switching the position control of the mechanical turning axis X1 between the first position control example and the second position control example, the trajectory along which the X-ray generator 22 or the X-ray detector 24 turns can be moved away from or brought close to the imaging region R. Alternatively, by changing the position (distance) of the mechanical turning axis X1 with respect to the center A of the imaging region R in the second position control example, the trajectory along which the X-ray generator 22 or the X-ray detector 24 turns can be moved away from or brought close to the imaging region R. These position control examples are more specifically described in a second embodiment.

By combination of the first and second position control examples, the trajectory along which the X-ray generator 22 or the X-ray detector 24 turns can be changed at multiple stages so as to be moved away from or brought close to the X-ray CT imaging region R.

The X-ray CT imaging region R is a region that is set as the target of the X-ray CT imaging with respect to the local part of the dental arch in the subject P.

The X-ray generator 22 and the X-ray detector 24 may turn by 360 degrees about the center A of the imaging region R, or may turn by less than 360 degrees, for example, 180 degrees.

It is assumed that the X-ray CT imaging of the local part of the dental arch is performed according to the position of the imaging region R set by the imaging region position setting unit 40. In this case, because of a positional relationship in an orbit setting in which the X-ray generator 22 and the X-ray detector 24 turn with the imaging region R interposed therebetween, a distance is kept between the center A and the X-ray generator 22 and between the center A and the X-ray detector 24. In the setting of the distance, it is assumed that separation distance D is a distance that is smaller one of a distance between the center A of the imaging region R and the X-ray generator 22 and a distance between the center A of the imaging region R and the X-ray detector 24. Similarly, it is assumed that the X-ray CT imaging is performed on the local part of the dental arch according to the position of the imaging region R set by the imaging region position setting unit 40. In this case, it is assumed that maximum distance LD is a distance of a surface of the head P with respect to the center A of the imaging region R in a turning range of the X-ray generator 22 or the X-ray detector 24 closer to the center A of the imaging region R. When the X-ray generator 22 and the X-ray detector 24 rotate by 360 degrees or more, the maximum distance LD is the maximum distance of the entire surface of the head P with respect to the center A of the imaging region R. When the X-ray generator 22 and the X-ray detector 24 rotate by less than 360 degrees, the maximum distance LD is decided by the center A of the imaging region R and the region existing inside the turning range closer to the center A of the imaging region R in the X-ray generator 22 or the X-ray detector 24 on the surface of the head P. This means that when the X-ray generator 22 and the X-ray detector 24 turn by less than 360 degrees to perform the X-ray CT imaging, the separation distance D is determined on the assumption that the X-ray generator 22 or the X-ray detector 24, which is located closer to the center A of the imaging region R in the head P, possibly partially comes into contact with the head P. When the X-ray CT imaging of the local part of the dental arch is performed according to the position of the imaging region R set by the imaging region position setting unit 40, the position of the mechanical turning axis X1 with respect to the center A of the imaging region R may be controlled such that the separation distance D is larger than the maximum distance LD according to the position of the imaging region R set by the imaging region position setting unit 40.

Whether the separation distance D is defined with respect to the X-ray generator 22 or the X-ray detector 24, namely, whether the X-ray detector 24 is brought closer to the center A than the X-ray generator 22 or whether the X-ray generator 22 is brought closer to the center A than the X-ray detector 24 depends on the situation. For example, the X-ray detector 24 is brought closer than the X-ray generator 22 in order to lower magnification, and the X-ray generator 22 is brought closer than the X-ray detector 24 in order to increase the magnification.

The description will be made based on an example of the positions of the two imaging regions R in FIG. 1. When the head P is irradiated with the X-ray generated from the X-ray generator 22 to perform the X-ray CT imaging on the local part of the dental arch, it is assumed that the separation distance D is a distance that is smaller one of a distance Dg between the center A of the imaging region R and the X-ray generator 22 and a distance Dd between the center A of the imaging region R and the X-ray detector 24. The separation distance D becomes Dd because the mechanical turning axis X1 is closer to the X-ray detector 24 than the X-ray generator 22.

Further, it is assumed maximum distances LD(1) and LD(2) of the surface of the head P with respect to the center A of the imaging region R. In the example of FIG. 1, the maximum distance LD(2) in which the head P2 where the molar region is set to the imaging region R is assumed is the distance between the center A of the imaging region R and a side portion opposite to the imaging region R in the head P. It can be understood that the dental arch has a right portion and a left portion when being divided into two, and that the dental arch has a central portion (front tooth center), a right portion, and a left portion when being divided into three. In each case, assuming that the imaging region R is set to one of the left and right molar regions, for example, the left molar region, the maximum distance LD(2) is the distance between the center A of the imaging region R and the right surface that is the other of the right and left surfaces in the head. The maximum distance LD(1) in which the head P1 where the front tooth region is set to the imaging region R is assumed is the distance between the center A of the imaging region R and a rear portion of the head P. The maximum distance LD(1) is larger than the maximum distance LD(2) because a front-back direction of the head is usually longer than a width direction of the head. It is assumed that the head P1 and the head P2 have the same size and shape.

When the X-ray CT imaging is performed on the local part of the dental arch according to the position of the imaging region R set by the imaging region position setting unit 40, the position of the mechanical turning axis X1 with respect to the center A of the imaging region R is controlled such that the separation distance D is larger than the maximum distances LD(1), LD(2) according to the position of the imaging region R set by the imaging region position setting unit 40.

When the molar region is set to the imaging region R, a separation distance Dd (hereinafter, sometimes referred to as a separation distance Dd(2)) is set to be larger than the maximum distance LD(2). When the front tooth region is set to the imaging region R, the separation distance Dd (hereinafter, sometimes referred to as a separation distance Dd(1)) is set to be larger than the maximum distance LD(1). When the separation distance Dd is increased, the X-ray generator 22 approaches the center A of the imaging region R, and it is assumed that the separation distance Dd is set within a range equal to or less than the changed distance Dg.

When the maximum distance LD(2) is relatively small while the molar region is set to the imaging region R, the X-ray detector 24 turns at the separation distance Dd(2) larger than the relatively small maximum distance LD(2). For this reason, the X-ray detector 24 can be turned while brought as close as possible to the head P2. The X-ray generator 22 turns at a position farther from the center A of the imaging region R than the X-ray detector 24.

When the maximum distance LD(1) is relatively large while the front tooth region is set to the imaging region R, the X-ray detector 24 turns at the separation distance Dd(1) larger than the relatively large maximum distance LD(1). The separation distance Dd(1) is larger than the separation distance Dd(2). Consequently, the X-ray detector 24 can be turned while brought as close as possible to the head P2 without contacting with the head P1. The X-ray generator 22 turns at a position farther from the center A of the imaging region R than the X-ray detector 24.

That is, the position of the turning axis X1 is controlled such that one of the X-ray generator 22 and the X-ray detector 24 (in this case, the X-ray detector 24) closer to the center A of the imaging region R during the performance of the X-ray CT imaging with the molars as the imaging region R passes through the trajectory closer than one of the X-ray generator 22 and the X-ray detector 24 (in this case, the X-ray detector 24) closer to the center A of the imaging region R during the performance of the X-ray CT imaging with the front tooth as the imaging region R with respect to the center A of the imaging region R.

For example, the turning control content of the mechanical turning axis X1 according to the position of the imaging region R is determined by referring to a reference table previously stored in the storage according to the set position of the imaging region R (for example, an anterior tooth region or a molar region). For example, the reference table can be set to a table in which the turning control content of the turning axis X1 is associated with each of the plurality of positions of the imaging region R.

On the assumption of the first position control example, the turning control content is defined as fixing of the mechanical turning axis X1 to a fixed position. On the assumption of the second position control example, the turning control content is defined as a pattern for moving the mechanical turning axis X1 about the center A of the imaging region R. A more specific example is a pattern for rotating the mechanical turning axis X1 at a predetermined axis turning radius with the center A of the imaging region R as the rotation center. The predetermined axis turning radius may be a value previously set according to the position of the imaging region R. The maximum distance between the center A of the imaging region R and the outer peripheral portion of the head P is calculated each time according to the position of the center A of the set imaging region R, and the predetermined axis turning radius may be obtained by arithmetic processing using an arithmetic expression or the like set based on a result of the calculation. In this case, for example, previously-stored data indicating a standard outer peripheral boundary of the head can be used as an outer peripheral boundary of the head P. Consequently, the turning control content including the position control of the turning axis X1 is decided.

In step S3, based on the decided turning control content, the turning controller 60 controls the turning mechanism 32 and the turning axis moving mechanism 38, and turns the X-ray generator 22 and the X-ray detector 24 about the center A of the imaging region R of the head P. At this point, the X-rays emitted from the X-ray generator 22 is incident on the X-ray detector 24 through the head P, and data used to generate the X-ray CT image is obtained. The X-ray CT image is generated based on this data.

In the X-ray CT imaging apparatus 10 configured as described above and the control method thereof, the position of the turning axis X1 is controlled according to the position of the imaging region R set by the imaging region position setting unit 40 and the like, so that the orbit along which the X-ray generator 22 and the X-ray detector 24 turn can be changed to prevent the X-ray generator 22 and the X-ray detector 24, which turn about the subject P, from contacting with the subject P.

In particular, according to the position of the imaging region R, the position of the turning axis X1 is controlled to change the turning locus of the X-ray detector 24. For this reason, according to the position of the imaging region R, the X-ray detector 24 can be brought as close as possible to the head P to perform the X-ray CT imaging while the contact between the X-ray detector 24 and the head P is prevented. Consequently, the clear X-ray image can be generated.

Second Embodiment

An X-ray CT imaging apparatus according to a second embodiment will be described.

Figure 3:
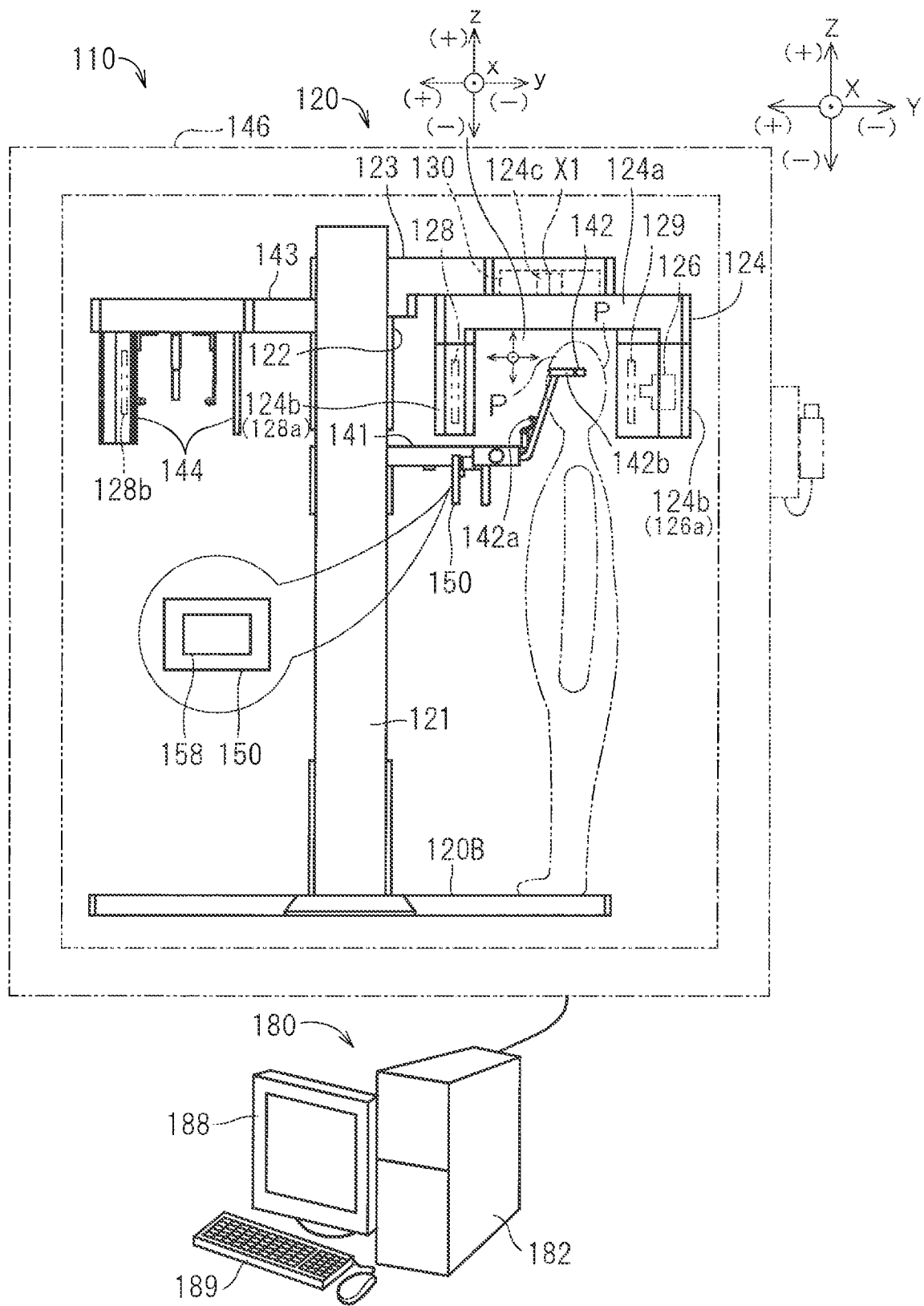
FIG. 3 is a schematic diagram illustrating an entire configuration of an X-ray CT imaging apparatus according to a second embodiment.

FIG. 3 is a schematic diagram illustrating an entire configuration of an X-ray CT imaging apparatus 110. An example in which the X-ray CT imaging apparatus 110 can perform not only the X-ray CT imaging but also panoramic imaging, cephalogram imaging, and the like will be described.

<Entire Configuration>

The X-ray CT imaging apparatus 110 includes an imaging main body 120 and an X-ray image processing apparatus 180. The imaging main body 120 is an apparatus that performs the X-ray imaging such as the X-ray CT imaging to collect projection data. The X-ray image processing apparatus 180 is an apparatus that processes the projection data collected by the imaging main body 120 and generates various images.

The imaging main body 120 includes a turning support 124 and a turning drive mechanism 130. The turning support 124 supports an X-ray generator 126 and an X-ray detector 128 such that the X-ray generator 126 and the X-ray detector 128 are opposed to each other with the head P sandwiched therebetween. The turning drive mechanism 130 includes a turning mechanism 132 and a turning axis moving mechanism 134. The turning mechanism 132 is a mechanism that turns the turning support 124 about the mechanical turning axis X1 between the X-ray generator 126 and the X-ray detector 128. The turning axis moving mechanism 134 is a mechanism that moves the mechanical turning axis X1 in a direction intersecting with the mechanical turning axis X1.

More specifically, a post 121 is supported in a perpendicular posture on a base 120B. A lifting unit 122 is liftably provided on the post 121. A lifting drive mechanism moves the lifting unit 122 up and down. A linear actuator such as a moving mechanism including a ball screw mechanism and a motor and a linear motor is used as the lifting drive mechanism, and the lifting drive mechanism moves the lifting unit 122 up and down while being incorporated in the post 121. A horizontal arm 123 is supported by the lifting unit 122 so as to extend in a horizontal direction. A turning drive mechanism 130 is incorporated at a leading end of the horizontal arm 123. A head fixing apparatus arm 141 (to be described later) extends from the post 121 in the same direction as the horizontal arm 123. A head fixing apparatus 142 is provided at the leading end of the head fixing apparatus arm 141, and the head P is held by the head fixing apparatus 142. In FIG. 3, a base end of the lifting unit 122 moves up and down behind the post 121. Assuming that the side on which the base end of the lifting unit 122 moves up and down is a back face and that a reverse of the back face is a front face, the horizontal arm 123 extends from the lifting unit 122 to the right of the post 121 in front view of FIG. 3. The head P is held in the head fixing apparatus 142 with the right in FIG. 3 as the rear and with the left as the front.

At this point, the direction is defined for convenience.

An XYZ-orthogonal coordinate system is an orthogonal coordinate system defined in a three-dimensional space in which the imaging main body 120 is installed. A Z-axis direction is a direction parallel to the axial direction of the mechanical turning axis X1. In the second embodiment, the direction parallel to the axial direction of the mechanical turning axis X1 and the lifting direction of the lifting unit 122 are matched with each other as the Z-axis direction. A Y-axis direction is a direction orthogonal to the Z-axis direction, and an X-axis direction is a direction orthogonal to the Z-axis direction and the Y-axis direction. A front-rear direction of the head P fixed to the head fixing apparatus 142 is set to the Y-axis direction, and a right and left direction of the head is set to the X-axis direction. In the present invention, sometimes the Z-axis direction is referred to as a Z-direction, the Y-axis direction is referred to as a Y-direction, and the X-axis direction is referred to as an X-direction.

The direction from the head P toward the base 120B, namely, a lower side is set to a −Z-side, and the direction away from the base 120B from the head P, namely, an upper side is set to a +Z-side. The front side of the head P is set to a +Y-side, and the rear side is set to a −Y-side. The right side of the head P is set to an +X-side, and the left side is set to an −X-side. Each axial direction, "+", and "−" are illustrated in FIG. 3.

An xyz-orthogonal coordinate system is an orthogonal coordinate system defined in the turning support 124 constituting an imaging system that performs the X-ray generation and the X-ray detection, the imaging system rotating around the mechanical turning axis X1. At this point, the axial direction of the mechanical turning axis X1 is set to a z-axis direction, and the z-axis direction is matched with the Z-axis direction of the XYZ-orthogonal coordinate system. A direction in which the X-ray generator 126 and the X-ray detector 128 are opposed to each other is set to a y-axis direction, and a direction orthogonal to the y-axis direction and the z-axis direction is set to an x-axis direction. The turning support 124 rotates with the mechanical turning axis X1 as the rotation axis, which allows the xyz-orthogonal coordinate system to rotate around the Z-axis (=z-axis) with respect to the XYZ-orthogonal coordinate system. In the present invention, sometimes the z-axis direction is referred to as a z-direction, the y-axis direction is referred to as a y-direction, and the x-axis direction is referred to as an x-direction.

In the y-axis direction, the side of the X-ray detector 128 is set to a +y-side, and the side of the X-ray generator 126 is set to a −y-side. In the x-axis direction, the right side from the −y-side toward the +y-side is set to a +x-side, and the left side is set to a −x-side. In the z-axis direction, the upper side in the vertical direction is set to a +z-side, and the lower side is set to a −z-side.

FIG. 4 is a schematic bottom view illustrating the turning drive mechanism 130. As illustrated in FIGS. 3 and 4, the turning drive mechanism 130 includes a turning axis moving mechanism 134 supported by the horizontal arm 123 as a kind of bracket and a turning mechanism 132 supported movably by the turning axis moving mechanism 134.

The turning axis moving mechanism 134 is a mechanism that moves the mechanical turning axis X1 in the direction intersecting with the mechanical turning axis X1, in this case, the direction orthogonal to the mechanical turning axis X1. The turning axis moving mechanism 134 is constructed with an XY-table mechanism, and moves the turning mechanism 132 to which the mechanical turning axis X1 is connected in the direction intersecting with the mechanical turning axis X1, thereby moving the mechanical turning axis X1 in the direction intersecting with the mechanical turning axis X1. More specifically, the turning axis moving mechanism 134 includes a fixed table 134B, an X-direction movable support 135, an X-direction drive unit 136, a Y-direction movable support 137, a Y-direction drive unit 138, and a movable table 139.

The X-direction movable support 135 includes a pair of linear guides 135*a* extending in the X-direction, the linear guides 135*a* being supported on the fixed table 134B in a spaced and parallel state. The Y-direction movable support 137 includes a pair of linear guides 137*a* extending in the Y-direction. The pair of linear guides 137*a* are movably supported on the pair of linear guides 135*a* along the X-direction that is the extending direction while having a posture intersecting with the pair of linear guides 135*a* (in this case, a posture orthogonal to the pair of linear guides 135*a*) in the spaced and parallel state. The movable table 139 is supported on the pair of linear guides 137*a* so as to be movable along the Y-direction that is the extending direction. The Y-direction movable support 137 moves along the X-direction on the X-direction movable support 135, which allows the movable table 139 to move in the X-direction. The movable table 139 moves along the Y-direction on the Y-direction movable support 137, which allows the movable table 139 to move in the Y-direction. Consequently, the movable table 139 can move freely in a plane orthogonal to the mechanical turning axis X1.

The X-direction drive unit 136 is a mechanism that reciprocally drives the Y-direction movable support 137 along the X-direction. For example, a ball screw mechanism in which a nut 136*c* fixed to the Y-direction movable support 137 is screwed to a ball screw 136*b* rotationally driven in both forward and reverse directions by a motor 136*a* can be used as the X-direction drive unit 136.

The Y-direction drive unit 138 is a mechanism that reciprocally drives the movable table 139 along the Y-direction. For example, a ball screw mechanism in which a nut 138*c* fixed to the movable table 139 is screwed to a ball screw 138*b* rotationally driven in both the forward and reverse directions by a motor 138*a* can be used as the Y-direction drive unit 138.

The turning mechanism 132 includes a motor 132*a*, and is supported in a suspended state by the movable table 139. A shaft 124*c* protruding upward from an intermediate portion in the extending direction of the turning support 124 is supported in the suspended state by the turning mechanism 132. The rotating movement of the motor 132*a* is transmitted to the shaft 124*c*, and the turning support 124 is turned about the shaft 124*c* by driving the motor 132*a*. The center axis of the shaft 124*c* is the mechanical turning axis X1. The turning axis X1 is located between the X-ray generator 126 and the X-ray detector 128, which are supported by the turning support 124. The rotating movement of the motor 132*a* is transmitted to the shaft 124*c* through a transmission mechanism such as a gear and a pulley as necessary. The shaft 124*c* is disposed along the vertical direction along a direction of gravity. Thus, the mechanical turning axis X1 is also disposed along the vertical direction.

The turning mechanism 132 supported by the movable table 139 can be moved along the plane orthogonal to the mechanical turning axis X1 by driving the X-direction drive unit 136 and the Y-direction drive unit 138. In particular, by combining the drive in the X-direction by the X-direction drive unit 136 and the drive in the Y-direction by the Y-direction drive unit 138, the turning mechanism 132 can rotationally be moved so as to draw a circular or arc-shaped orbit.

The mechanism that moves the movable table 139 in the X-direction and the mechanism that moves the movable table 139 in the Y-direction are not limited to the above examples, but a configuration using a linear actuator such as a linear motor can be adopted. The turning axis moving mechanism 134 does not necessarily have the above configuration. The turning axis moving mechanism may be a mechanism that moves the turning mechanism only along one linear direction intersecting with the mechanical turning axis X1. The turning axis moving mechanism may be a mechanism, such as a robot arm including a plurality of joints, which turns an arm supporting the turning mechanism, thereby turning the turning mechanism in the direction intersecting with the mechanical turning axis X1.

The turning mechanism may be provided in the turning support. For example, the turning axis moving mechanism may directly move the mechanical turning axis X1 with no use of the turning mechanism. As a more specific example, a shaft corresponding to the mechanical turning axis X1 is fixed to the movable table 139 so as not to be turnable and so as to be movable in the direction intersecting with the mechanical turning axis X1, and the turning support 124 is turnably connected to the shaft. The turning mechanism 132 is provided in the turning support 124, and the turning mechanism 132 generates turning force with respect to the shaft, whereby the turning support 124 may be turned with respect to the shaft.

When the X-ray CT imaging is performed by irradiating the head P that is the subject with the X-ray generated from the X-ray generator 126, the turning axis moving mechanism 134 moves the mechanical turning axis X1 in synchronization with the turning of the turning support 124 about the mechanical turning axis X1 using the turning mechanism 132, and the turning support 124 is caused to perform the combined motion, which allows the X-ray generator 126 and the X-ray detector 128 to be turned around the center of an imaging region R.

As illustrated in FIG. 3, the turning support 124 is a portion that is supported such that the X-ray generator 126 and the X-ray detector 128 are opposed to each other with the head P interposed therebetween. The turning support 124 has a shape in which suspending supports 124*b* are provided at both ends of an elongated arm body 124*a*, namely, a U-shape that is open downward. The shaft 124*c* protruding upward is provided in the intermediate portion in the extending direction of the arm body 124a, and the shaft 124c is supported in the suspended state by the turning mechanism 32.

The X-ray generator 126 is provided in one suspending support 124b. The X-ray generator 126 includes an X-ray tube, and is configured to be capable of outputting the X-ray emitted from the X-ray tube toward the X-ray detector 128. The suspending support 124b on the side on which the X-ray generator 126 is provided is also an X-ray generating unit 126a including the X-ray generator 126.

An X-ray regulating unit 129 that adjusts a regulation amount of the X-ray generated from the X-ray generator 126 is provided on the side irradiated with the X-ray with respect to the X-ray detector 128. The X-ray regulating unit 129 is a member in which an X-ray regulating hole is made. The X-ray regulating unit 129 permits passage of part of the X-ray generated from the X-ray generator 126 according to the shape and size of the X-ray regulating hole, and shields an outside of a passage range of the X-ray. Consequently, the range of the X-ray beam traveling to the X-ray detector 128 is regulated. In the X-ray regulating unit 129, a plurality of types of X-ray regulating holes are made to switch the X-ray regulating holes regulating X-rays, or a member in which the X-ray regulating hole is made is moved to adjust an opening width of the X-ray regulating hole, thereby adjusting a shielded amount of the X-ray generated from the X-ray generator 126, namely, the regulation amount.

The X-ray detector 128 is provided on the other suspending support 124b, so that the X-ray detector 128 is disposed so as to be opposed to the X-ray generator 126 with the head P interposed therebetween. The X-ray detector 128 includes an X-ray detector including a planar detection surface, and is configured to be able to detect the X-ray (X-ray beam), which is emitted from the X-ray generator 126 and transmitted through the head P. Projection data of the X-ray imaging can be obtained by the X-ray detector 128. The suspending support 124b on the side on which the X-ray detector 128 is provided is also an X-ray detecting unit 128a including the X-ray detector 128.

A space in which the head P can be disposed is provided between the X-ray generator 126 and the X-ray detector 128.

In the second embodiment, the X-ray generator 126 and the X-ray detector 128 are attached to both ends of the U-shaped turning support. Alternatively, the X-ray generator and the X-ray detector may be supported by an annular member while opposed to each other. A shaft can be provided on a support member traversing a part in a circumferential direction or an inside of the annular member such that the annular member can turnably be supported. In the second embodiment, the X-ray generator 126 and the X-ray detector 128 are supported so as to be rotatable around the vertical axis. Alternatively, the X-ray generator 126 and the X-ray detector 128 may be supported so as to be rotatable about an axis oblique to the vertical direction, or the X-ray generator 126 and the X-ray detector 128 may be supported so as to be rotatable about a horizontal axis.

The turning support 124 can move up and down by the lifting unit 122 according to a height of the head P. The turning support 124 can be turned by the turning drive mechanism 130 such that the X-ray generator 126 and the X-ray detector 128 turn about the head P.

The head fixing apparatus arm 141 extending in the horizontal direction is provided in a portion of the post 121 below the horizontal arm 123. The horizontal arm 123 and the head fixing apparatus arm 141 extend in the same direction with the side of the post 121 as the base end. The head fixing apparatus arm 141 extends toward the lower side of the horizontal arm 123, and the head fixing apparatus 142 is provided at a leading end of the head fixing apparatus arm 141. The head fixing apparatus 142 is located between the X-ray generator 126 and the X-ray detector 128. The head fixing apparatus 142 includes a chin rest 142a on which a chin of the head P that is the subject can be placed and supported and a holder 142b that holds the head P that is the subject while sandwiching the head P from both outsides. The chin of the head P is supported on the chin rest 142a, and the head P is sandwiched by the holder 142b, whereby the head P is held at a fixed position between the X-ray generator 126 and the X-ray detector 128. The head fixing apparatus 142 may be constructed with at least one of the chin rest 142a and the holder 142b. A cephalogram imaging head fixing apparatus hanging arm 143 is provided so as to extend horizontally from the post 121 to the opposite side to the side where the horizontal arm 123 extends. A cephalogram imaging head fixing apparatus 144 is held while suspended from the cephalogram imaging head fixing apparatus hanging arm 143. A cephalogram imaging X-ray detector 128b is incorporated in the cephalogram imaging head fixing apparatus 144.

A main body controller 150 including an operation panel apparatus 158 is provided in an intermediate portion in the extending direction of the head fixing apparatus arm 141. In FIG. 3, the operation panel apparatus 158 of the main body controller 150 is enlarged and drawn in a balloon.

The X-ray imaging is performed in the state in which the head P that is the subject is fixed by the head fixing apparatus 142, and in the state in which the turning support 124 is stopped or rotated according to a desired imaging mode. Consequently, the X-ray image data necessary for generating the X-ray CT image, panoramic image, and the like can be obtained. For example, the X-ray imaging is performed while the turning support 124 is turned, which allows the obtainment of the X-ray CT image data necessary for the generation of the X-ray CT image. In addition, panoramic photographed images can be obtained by carrying out the X-ray imaging while the turning support 124 is rotated within a certain range. Additionally, the X-ray CT imaging apparatus 110 may also perform the X-ray imaging in order to obtain the cephalogram image and a pseudo-oral image. For example, while the turning support 124 is stopped, the head P is fixed to the cephalogram imaging head fixing apparatus 144 that is supported by the cephalogram imaging head fixing apparatus hanging arm 143 extending horizontally from the post 121. In this state, the X-ray generator 126 emits the X-ray to perform the X-ray imaging, whereby a cephalogram image can be obtained. A function of imaging the panoramic image and a function of imaging the cephalogram image are sometimes omitted.

The main body controller 150 is configured to be able to receive each instruction to the imaging main body 120, and is configured to be able to control each action of the imaging main body 120. The main body controller 150 is fixed to the head fixing apparatus arm 141 extending in the horizontal direction from the post 121. The operation panel apparatus 158 is provided in the main body controller 150, the operation panel apparatus 158 displaying various kinds of information from the main body controller 150 while receiving various commands to the main body controller 150. The operation panel apparatus 158 is a touch panel including a display apparatus such as a liquid crystal display panel and a touch detector disposed on a display screen of the display apparatus. A touch operation of the user on the display screen is detected with the touch detector, which allows the reception of the operation performed on the X-ray CT imaging apparatus 110. A push button or the like may be provided near the operation panel apparatus 158. The display apparatus and an input apparatus that receives the operation of the user may separately be provided.

Each unit of the imaging main body 120 is accommodated in an X-ray protection chamber 146. A push button switch called a deadman switch that issues an instruction of the X-ray irradiation to the main body controller 150 is provided on an outside of a wall of the X-ray protection chamber 146.

The X-ray image processing apparatus 180 includes an information processing main body 182 constructed with, for example, a computer or a work station, and is connected to the imaging main body 120 through a communication cable so as to be able to transmit and receive various data. However, the transmission and reception of the data may be performed by wireless communication between the imaging main body 120 and the X-ray image processing apparatus 180. The information processing main body 182 can perform various pieces of image processing based on the data transmitted from the imaging main body 120.

A display 188 constructed with the display apparatus such as a liquid crystal monitor and an operating unit 189 constructed with a keyboard, a mouse, and the like are connected to the X-ray image processing apparatus 180. The operator can issue various instructions to the information processing main body 182 by operating a pointer through the mouse on characters or images displayed on the display 188. The display 188 may be constructed with a touch panel.

Part or whole of the processing of the X-ray image processing apparatus 180 may be performed by the main body controller 150. Alternatively, part or whole of the processing of the main body controller 150 may be performed by the X-ray image processing apparatus 180.

<Block Diagram of X-Ray CT Imaging Apparatus>

Figure 5:
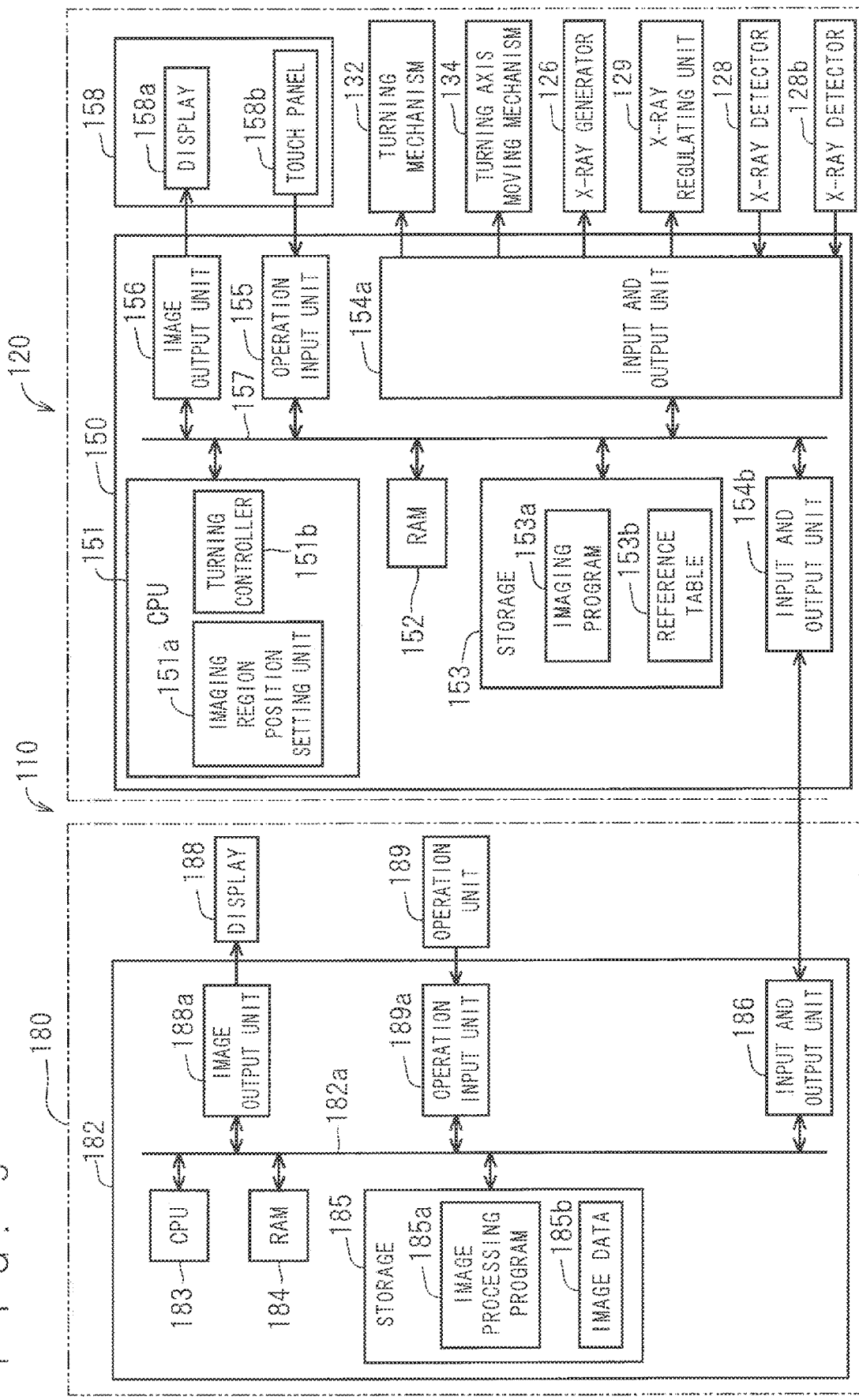
FIG. 5 is a block diagram illustrating an electric configuration of the X-ray CT imaging apparatus.

FIG. 5 is a block diagram illustrating an electric configuration of the X-ray CT imaging apparatus 110.

The main body controller 150 of the imaging main body 120 controls an X-ray imaging action of the imaging main body 120, and is constructed with a computer in which a Central Processing Unit (CPU) 151 that is at least one processor, a Random Access Memory (RAM) 152, a storage 153, input and output units 154a, 154b, an operation input unit 155, and an image output unit 156 are interconnected to one another through a bus line 157. The storage 153 includes a nonvolatile storage device such as a flash memory or a hard disk drive. An imaging program 153a, which receives various instructions relating to the X-ray imaging while controlling the X-ray imaging action by controlling the turning drive mechanism 130, the X-ray generator 126, the X-ray regulating unit 129, and the like according to the instructions, is stored in the storage 153. A reference table 153b, which is referred to when the turning control content of the turning drive mechanism 130 is decided according to the set position of the imaging region R during the setting of the position of the imaging region R in the head P, is stored in the storage 153. The reference table 153b is a table in which the position of the imaging region R is associated with the turning control content of the turning drive mechanism 130 and the like. In consideration of the position of the imaging region R in the head P, the shape and size of the standard (for example, standard adult) head P, each of the distances between the X-ray generator 126 and the X-ray detector 128 and the mechanical turning axis X1, and the like, the turning control content of the turning drive mechanism 130 such that the X-ray generator 126 and the X-ray detector 128 do not contact with the head P are theoretically and experimentally determined when turning. An example of the turning control content according to the position of the imaging region R will be described later. The RAM 152 serves as a work area when the CPU 151 performs predetermined processing. The input and output unit 154a is connected to a motor of the turning mechanism 132 that turns the turning support 124 of the imaging main body 120, a motor of the turning axis moving mechanism 134 that moves the turning support 124, the X-ray generator 126, the X-ray detectors 128, 128b, and the X-ray regulating unit 129, and the input and output unit 154b is communicably connected to the X-ray image processing apparatus 180. The operation input unit 155 is connected to the touch detector 158b of the operation panel apparatus 158, and the image output unit 156 is connected to the display 158a of the operation panel apparatus 158.

In the main body controller 150, the CPU 151 performs arithmetic processing according to a procedure described in the imaging program 153a, an instruction received through the touch detector 158b, and the like. Thus, the CPU 151 performs functions as an imaging region position setting unit 151a that receives the setting of the position of the imaging region R with respect to the local part of the dental arch of the head P of the subject and a turning controller 151b that controls the turning mechanism 132 and the turning axis moving mechanism 134 when the X-ray imaging such as the X-ray CT imaging is performed. Specifically, the CPU 151 controls the turning drive mechanism 130, specifically, the turning mechanism 132 and the turning axis moving mechanism 134 to turn the X-ray generator 126 and the X-ray detector 128 about the head P, and a result of the X-ray detected by the X-ray detectors 128 through the head P can be obtained. The CPU 151 can also obtain a result of the X-ray, the head P fixed to the cephalogram imaging head fixing apparatus 144 being irradiated with the X-ray emitted from the X-ray generator 126 and the X-ray being detected by the X-ray detector 128b.

The imaging program 153a and the reference table 153b are previously stored in the storage 153. Alternatively, the imaging program 153a and the reference table 153b may be provided to the existing X-ray CT imaging apparatus or the information processing main body that controls the X-ray CT imaging apparatus in the form of being recorded on a recording medium such as a CD-ROM, a DVD-ROM, or an external flash memory, or by download from an external server through a network.

The X-ray image processing apparatus 180 generates X-ray image data 185b based on the imaging data from the imaging main body 120. The information processing main body 182 is constructed with a computer in which a CPU 183 that is at least one processor, a RAM 184, a storage 185, an input and output unit 186, an operation input unit 189a, an image output unit 188a, and the like are interconnected to one another through a bus line 182a. The storage 185 is constructed with a nonvolatile storage device such as a flash memory or a hard disk drive. The storage 185 stores an image processing program 185a with which the information processing main body 182 generates the X-ray image data 185b based on the imaging data from the imaging main body 120 and X-ray image data 185b. Management data in which the X-ray image data 185b is correlated with specific information about the head P (specific information about a patient) may be stored in the storage 185. The X-ray image processing apparatus 180 receives data relating to an imaging condition from the main body controller 150, and may store the data relating to an imaging condition in the storage 185 while correlating the data relating to an imaging condition with the generated X-ray image data 185b. The RAM 184 serves as a work area when the CPU 183 performs predetermined processing. The input and output unit 186 is connected to the imaging main body 120, and the X-ray imaging data obtained by the imaging main body 120 is input to the input and output unit 186 through the input and output unit 186. A signal, such as a command signal, from the X-ray image processing apparatus 180 to the imaging main body 120 is also output through the input and output unit 186. The operation input unit 189a is connected to the operating unit 189, and the image output unit 188a is connected to the display 188. For example, the operation input unit 189a may be configured to convert a manual operation applied to the operating unit 189 into an electric signal suitable for a signal format of the bus line 182a. For example, the image output unit 188a may be configured to convert the image data 185b and other graphic data into a signal suitable for display on the display 188, a connection format, and the like.

In the information processing main body 182, the CPU 183 performs the arithmetic processing according to the image processing program 185a, thereby performing the processing as the image processor that generates the desired X-ray image data based on the X-ray imaging data obtained by the imaging main body 120. That is, data such as the CT image, the panoramic image, and the cephalogram image is generated in response to an instruction received through the main body controller 150. The storage 185 stores the generated X-ray image data 185b.

A part or whole of the function implemented in each of the above units may be implemented in a hardware manner using a dedicated logic circuit or the like. A part or whole of the function implemented in each of the above units may be processed by a single processor in an integrated manner, or appropriately processed by a plurality of processors in a distributed manner.

<Setting of Position of Imaging Region R and Turning Processing During Imaging>

Figure 6:
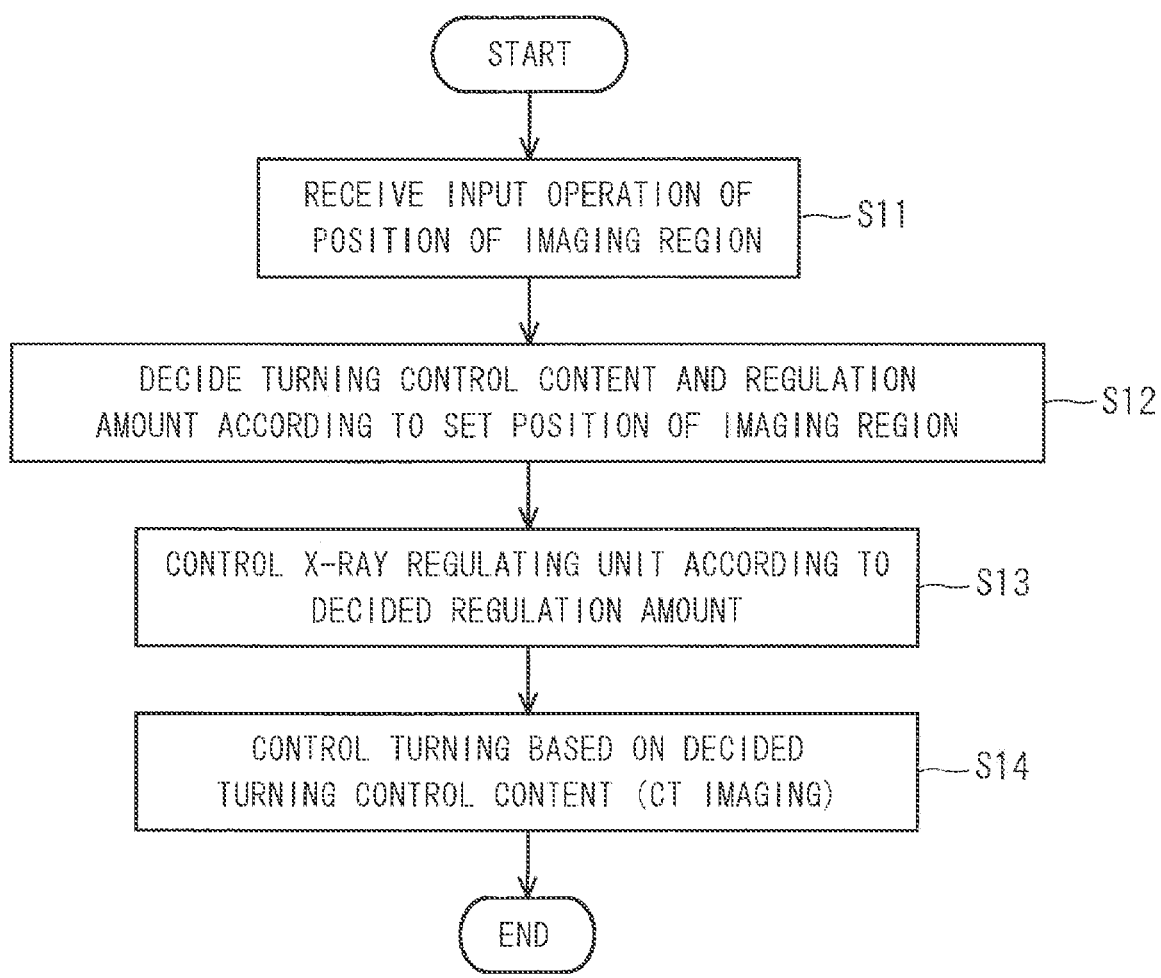
FIG. 6 is a flowchart illustrating a processing example of an imaging program.

With reference to a flowchart in FIG. 6, the imaging program 153a will be described centered on the setting of the position of the imaging region R and the turning processing during the imaging.

When the performance of the CT imaging is set, the setting operation of the position of the imaging region R is received in step S11.

Figure 7:
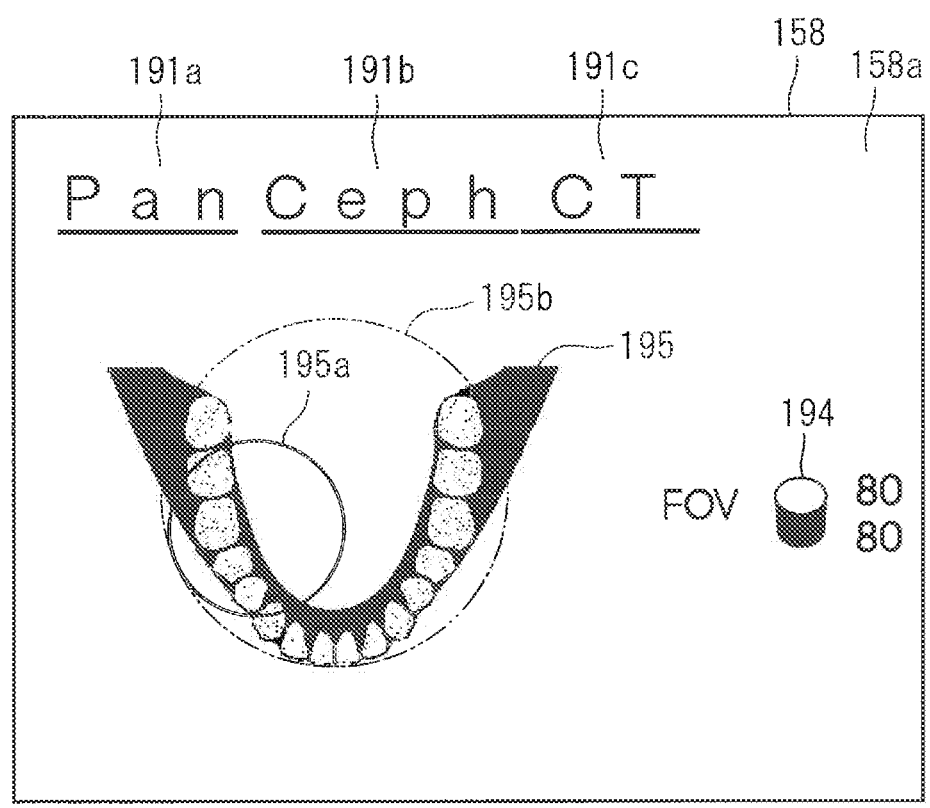
FIG. 7 is a view illustrating a display example in an operation panel apparatus.

An example in which the setting operation of the position of the imaging region R is received will be described below. FIG. 7 is a view illustrating a display example in the operation panel apparatus 158. A panorama selection image 191a (see characters "Pan"), a cephalogram selection image 191b (see characters "Ceph"), and a CT selection image 191c (see characters "CT") are displayed on the display 158a of the operation panel apparatus 158 as the image used to select the imaging mode. On the display 158a, an imaging region setting image 194 is displayed as an image for setting an imaging condition. In this case, the imaging region setting image 194 is displayed on the right side of the display 158a (the left side when viewed in the direction toward the front of the drawing). An illustration image 195 is displayed on the display 158a. The illustration image 195 is displayed on the lower sides of the panorama selection image 191a, the cephalogram selection image 191b, and the CT selection image 191c in the display 158a. The illustration image 195 is an image for representing the imaging region R, and the dental arch is displayed as the illustration image.

A touch panel is provided on the display 158a as touch detector 158b that is a two-dimensional position detector that detects the touch position with respect to the display region.

When the operator touches any one of the panorama selection image 191a, the cephalogram selection image 191b, and the CT selection image 191c, the touch operation is detected by the touch detector 158b. Consequently, the main body controller 150 receives whether to perform the panoramic imaging, the cephalogram imaging, or the X-ray CT imaging. This can be said to be the reception of a selection operation of an imaging mode in each imaging.

Figure 8:
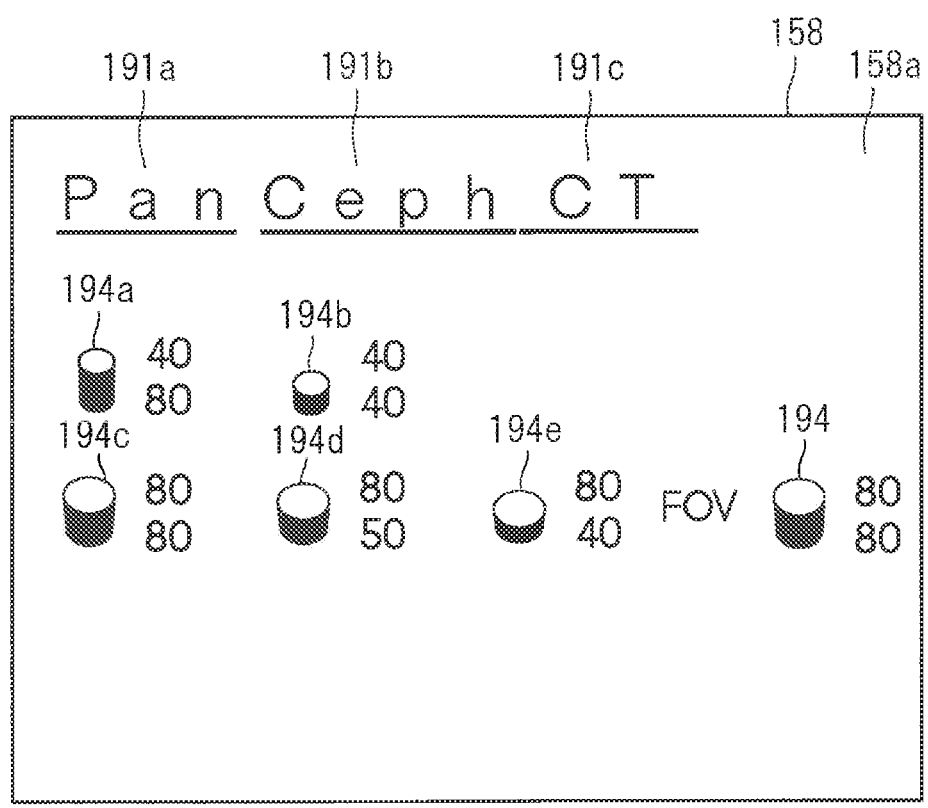
FIG. 8 is a view illustrating a display example in the operation panel apparatus.

As illustrated in FIG. 8, when the operator touches the imaging region setting image 194, a plurality of imaging region selection images 194a, 194b, 194c, 194d, 194e corresponding to the imaging region setting image 194 are displayed according to the touch operation. The plurality of imaging region selection images 194a, 194b, 194c, 194d, 194e indicate regions in which sizes (a diameter and a height) are different from one another. The operation to set the imaging region is received when the user selectively touches any one of the plurality of imaging region selection images 194a, 194b, 194c, 194d, 194e.

In the example of FIG. 8, the imaging region selection images 194a, 194b are images used to select the imaging region R having a diameter of 40 mm. The imaging region selection image 194a indicates that the imaging region R has the height of 80 mm, and the imaging region selection image 194b indicates that the imaging region R has the height of 40 mm. Regardless of the height of the imaging region R, the fact that the imaging region R has the diameter of 40 mm indicates that the local part of the dental arch, strictly, the local part viewed from a body axial direction is designated as the region. Thus, it can be said that the imaging region selection images 194a, 194b are images for receiving the performance of the X-ray CT imaging while the local part of the dental arch is set to the target.

The imaging region selection images 194c, 194d, 194e are images for selecting the imaging region R having the diameter of 80 mm. The imaging region selection images 194c, 194d, 194e indicate that the heights of the imaging region R are 80 mm, 50 mm, and 40 mm, respectively. Regardless of the height of the imaging region R, the fact that the imaging region R has the diameter of 80 mm indicates that a whole of the dental arch is designated as the region. Thus, it can be said that the imaging region selection images 194b, 194c, 194d are images for receiving the performance of the X-ray CT imaging while the whole of the dental arch, strictly, the whole viewed from the body axial direction is designated as the region.

When the X-ray detector 128 has the narrow detection surface, a configuration in which the X-ray CT imaging can be performed only in the local part, for example, the imaging region R having the diameter of 40 mm may be adopted.

When the entire jawbone is set to the imaging target, the X-ray detector 128 having a wide detection surface may be used to select the imaging region R having the diameter of 130 mm or more.

Even if the X-ray detector 128 does not have the wide detection surface, offset scanning is performed on the imaging region R having the diameter more than 80 mm, so that the X-ray CT imaging may be performed on the imaging region R having the diameter of 130 mm or more, for example. In this way, the X-ray CT imaging is performed on the imaging region R of the local part and/or whole of the dental arch by normal scan that is not the offset scan, and the X-ray CT imaging is performed on the imaging region R exceeding the whole of the dental arch by the offset scan.

The offset scan can be performed by performing the following operation. For example, the mechanical turning axis X1 is offset from the center of the imaging region R in a direction including a component in the x-direction by the turning axis moving mechanism 134. In this state, in synchronization with the turning of the turning support 124 about the mechanical turning axis X1 using the turning mechanism 132, the turning axis moving mechanism 134 moves the mechanical turning axis X1 along a circular orbit about the center of the imaging region R, and causes the turning support 124 to perform the combined motion. Consequently, the X-ray generator 126 and the X-ray detector 128 turn about the center of the imaging region R while being maintained in the offset state.

Returning to FIG. 7, an imaging region image 195a (or an imaging region image 195b) is displayed while superimposed on the illustration image 195. A circle having the size set through the imaging region setting images 194 is displayed as the imaging region images 195a, 195b. The imaging region image 195a is an image that is displayed during the selection of the imaging region R where the local part of the dental arch is set to the target, and the imaging region image 195b is an image that is displayed during the selection of the imaging region R where the whole of the dental arch is set to the target. When the imaging region image 195a is selected, the operator touches any position of the illustration image 195 to move the imaging region image 195a to the position where the local part of the dental arch is designated. Consequently, the imaging region R can be designated at any position of the dental arch (for example, a front tooth region, a right molar region, a left molar region).

The example in which the imaging mode is designated or the imaging region R is designated using the touch panel is described above. Alternatively, various settings may be received through a switch (push button) that physically receives an operation.

In this way, in step S11, the imaging region position setting unit 151a receives the setting operation of the position of the imaging region R with respect to the local part of the dental arch of the head P through the operation panel apparatus 158. At this point, the imaging region position setting unit 151a receives the setting of the position of the imaging region R by receiving the selection of any one of the imaging region selection images 194a, 194b and the position setting of the illustration image 195 using the imaging region image 195a or 195b through the operation panel apparatus 158.

In step S12, the turning control content and the regulation amount are decided according to the set position of the imaging region. The turning control content indicates how to turn the X-ray generator 126 and the X-ray detector 128 around the head P with what kind of trajectory. The turning control content includes the trajectory of at least one of the X-ray generator 126 and the X-ray detector 128, the moving trajectory of the mechanical turning axis X1 by the turning axis moving mechanism with respect to the turning speed of the turning support 124 by the turning mechanism 132, or the moving coordinates of the turning axis X1 by the X-direction drive unit 136 and the Y-direction drive unit 138 with respect to the turning speed of the turning support 124 by the turning mechanism 132.

When the turning control content is decided, the separation distance D is decided on the assumption that the separation distance D is the distance that is smaller one of the distance between the center A of the imaging region R and the X-ray generator 126 and the distance between the center A of the imaging region R and the X-ray detector 128 during the turning of the X-ray generator 126 and the X-ray detector 128 about the center A of the imaging region R. In the second embodiment, the turning axis X1 is located closer to the X-ray detector 128 in the turning support 124, and the position of the turning axis X1 is preferentially matched with the center A of the imaging region R as much as possible in setting of the orbit, and the distance between the X-ray detector 128 and the center A of the imaging region R is made smaller than the distance between the X-ray generator 126 and the center A of the imaging region R. For this reason, the separation distance D is the distance between the center A of the imaging region R and the X-ray detector 128. The position of the imaging region R in the apparatus 110 is already calculated or at least can be calculated, because the head P is held at a fixed position by the head fixing apparatus 142 and the imaging region is set as described above.

Because the distance of the X-ray generator 126 to the center A of the imaging region R is also decided, magnification is also decided when the X-ray emitted from the X-ray generator 126 is incident on the X-ray detector 128 through the head P. Assuming that DA is the distance between the X-ray generator 126 and the X-ray detector 128, and that D1 is the distance between the X-ray generator 126 and the center A of the imaging region R, magnification m becomes m=DA/D1. Assuming that D2 is the distance between the X-ray detector 128 and the center A of the imaging region R, the magnification may be calculated as n=DA/D2. A change in magnification m and a change in magnification n are inversely proportional to each other.

When the turning control content is decided, the minimum width of the X-ray is decided to allow the X-ray generated from the X-ray generator 126 to pass through the whole of the imaging region R. Consequently, an amount of the X-ray regulation width (X-ray regulation hole) to be regulated by the X-ray regulating unit 129 can also be set within a range larger than the minimum width and a range in which the surrounding area is not excessively irradiated with the X-ray. When the size of the imaging region R is identical, it can also be said that the regulation width is set according to the distance between the center A of the imaging region R and the X-ray generator 126 during the turning of the X-ray generator 126 and the X-ray detector 128 about the center A of the imaging region R. The X-ray regulating unit 129 adjusts the regulation amount of the X-ray generated from the X-ray generator 126 according to the distance between the center A of the imaging region R and the X-ray generator 126.

For example, the X-ray regulating unit 129 is constructed with four X-ray shielding members, and the X-ray shielding members are disposed on a front surface of an X-ray irradiation port of the X-ray generator 126 on the +z-side, the −z-side, +x-side, and −x-side centered on the X-ray irradiation port. The X-ray shielding member on the +z-side and the X-ray shielding member on the −z-side are independently driven so as to be displaceable in the z-direction, the X-ray shielding member on the +x-side and the X-ray shielding member on the −x-side are independently driven so as to be displaceable in the x-direction, and the drive of the X-ray shielding members is controlled by an X-ray regulating unit drive controller (not illustrated). A space surrounded by the X-ray shielding members is a region through which the X-ray can pass, and is the X-ray regulating hole. The X-ray regulating hole having a desired shape is formed by displacement drive control of the four X-ray shielding members. In other words, the region through which the X-ray can pass, namely, the X-ray regulating hole is an X-ray passage permitting unit. The regulation width means the width of the regulated space, and is the width of the X-ray passage permitting unit, namely, the width of the X-ray regulating hole. Thus, a relationship that the regulation width is decreased to increase the regulation amount while the regulation width is increased to decrease the regulation amount holds.

For example, the decision of the turning control content and the regulation amount according to the set position of the imaging region can be performed by referring to the reference table in FIG. 9. That is, the reference table in which the turning control content, the separation distance D (magnification m), and the regulation width W are associated with the position of the imaging region is previously registered. In the example of FIG. 9, the turning of the mechanical turning axis X1 with a radius r about the center A of the imaging region R, a separation distance D(1) (magnification m(1)), and a regulation width W(1) are associated with the case where the position of the imaging region is set to the front tooth as the turning control content. The turning of the mechanical turning axis X1 with the mechanical turning axis X1 matched with the center A of the imaging region R, a separation distance D(2) (magnification m(2)), and a regulation width W(2) are associated with the case where the position of the imaging region is set to the molar tooth as the turning control content. The separation distance D(1), the magnification m(1), the regulation width W(1), the separation distance D(2), the magnification m(2), the regulation width W(2), and the radius r are specified as specific numerical values. As described later, when the position of the imaging region is set to the front tooth, the X-ray detector 128 is located farther from the center A of the imaging region than the case where the position of the imaging region is set to the molar tooth (in contrast, the X-ray generator 126 comes close to the center A of the imaging region R). For this reason, the separation distance D(1)>the separation distance D(2), the magnification m(1)>the magnification m(2), and the regulation width W(1)>the regulation width W(2) hold.

The information about the regulation width W(n) may be accompanied with information about a regulation amount WL(n) corresponding to a regulation width W(n), and the regulation amount WL(n) may be replaced with the regulation amount W(n).

Whether the imaging region R is the front tooth or the molar tooth is determined based on the set imaging region R, and the corresponding turning control content, the separation distance D (magnification m), and the regulation width W are decided based on the determination result. For example, the position (the front tooth or the molar tooth) of the imaging region R based on the set imaging region R can be determined based on whether the set coordinate of the center A of the imaging region R belongs to the front tooth region and the molar tooth region. The imaging region in the reference table may be divided into a larger number of regions for the dental arch.

In this case, in the reference table, the turning control content corresponding to the position of the imaging region R is defined on the assumption that the physique (size) of the head P is identical. Alternatively, the turning control content corresponding to the position of the imaging region R may be defined for each of the heads P having different sizes (for example, a head for an adult physique and a head for a child physique). In this case, according to the physique input by the operator, the position of the imaging region R may be controlled according to the physique. This will also be described in a modification (to be described later).

In step S13, the X-ray regulating unit 129 is controlled according to the regulation widths W(1), W(2) corresponding to the decided regulation amount such that the X-ray having the width corresponding to the imaging region R is emitted from the X-ray detector 128.

In step S14, the CT imaging is performed by performing the turning control based on the decided turning control content. That is, when the X-ray CT imaging is performed by irradiating the head P with the X-ray generated from the X-ray detector 128, the position of the turning axis X1 is controlled according to the position of the imaging region set by the imaging region position setting unit 151a.

An example in which the drive control causing the turning mechanism 32 to perform the above combined motion and the drive control turning the turning support 124 with the mechanical turning axis X1 fixed to the position of the center A of the imaging region R are switched according to the position of the imaging region set by the imaging region position setting unit 151a will be described below.

In this case, it is assumed that the X-ray CT imaging is performed on the local part of the dental arch according to the position of the imaging region R set by the imaging region position setting unit 151a when the X-ray generator 126 and the X-ray detector 128 are turned about the center A of the imaging region R. At this point, the position of the mechanical turning axis X1 with respect to the center A of the imaging region R is controlled such that the separation distance D is larger than the maximum distance LD according to the position of the imaging region R set by the imaging region position setting unit 151a. As described in the first embodiment, the maximum distance LD is the maximum distance LD of the surface of the head P with respect to the center A of the imaging region R in the range in which the X-ray generator 22 or the X-ray detector 24 closer to the center A of the imaging region R turns when the X-ray CT imaging is performed on the local part of the dental arch according to the position of the set imaging region R. The maximum distance LD changes according to the position of the imaging region R. When the X-ray generator 126 and the X-ray detector 128 rotate by 360 degrees or more to perform the CT imaging, the maximum distance LD is the maximum distance LD of the whole surface around the head P with respect to the center A of the imaging region R. When the X-ray generator 126 and the X-ray detector 128 rotate by less than 360 degrees (for example, 180 degrees) to perform the CT imaging, the maximum distance LD is the maximum distance between the surface of the head P existing inside the range in which the X-ray generator 126 or the X-ray detector 128 closer to the center A of the imaging region R turns and the center A of the imaging region R. The separation distance D is a smaller one of the distance between the center A of the imaging region R and the X-ray generator 126 and the distance between the center A of the imaging region R and the X-ray detector 128. In the second embodiment, the mechanical turning axis X1 turns about the center A of the imaging region R while the positional relationship provided between the center A of the imaging region R and the X-ray detector 128 is maintained.

In this case, in the case where the imaging region R is the front tooth, when the X-ray CT imaging is performed by irradiating the head P with the X-ray generated from the X-ray generator 126, the turning axis moving mechanism 134 rotates the mechanical turning axis X1 about the center A of the imaging region R in synchronization with the turning of the turning support 124 about the mechanical turning axis X1 using the turning mechanism 132, whereby the turning support 124 is caused to perform the combined motion. In the case where the imaging region R is the molar tooth, when the X-ray CT imaging is performed by irradiating the head P with the X-ray generated from the X-ray generator 126, the turning mechanism 132 turns the turning support 124 about the mechanical turning axis X1 while the turning axis moving mechanism 134 fixes the mechanical turning axis X1 to the position of the center A of the imaging region R.

The switching of the drive control with respect to the position of the imaging region R is reversed in some cases depending on the position of the turning axis X1 with respect to the X-ray generator 126 and the X-ray detector 128. For example, in the case where the turning axis X1 is located at the position close to the middle between the X-ray generator 126 and the X-ray detector 128, the drive control in which the turning support 124 is turned while the mechanical turning axis X1 is fixed to the position of the center of the imaging region R may be performed when the imaging region R is set to the front tooth, and the drive control in which the turning support 124 is caused to perform the above combined motion may be performed when the imaging region R is set to the molar tooth.

An example of the turning operation will be described in more detail with reference to FIGS. 10 and 11.

Figure 10:
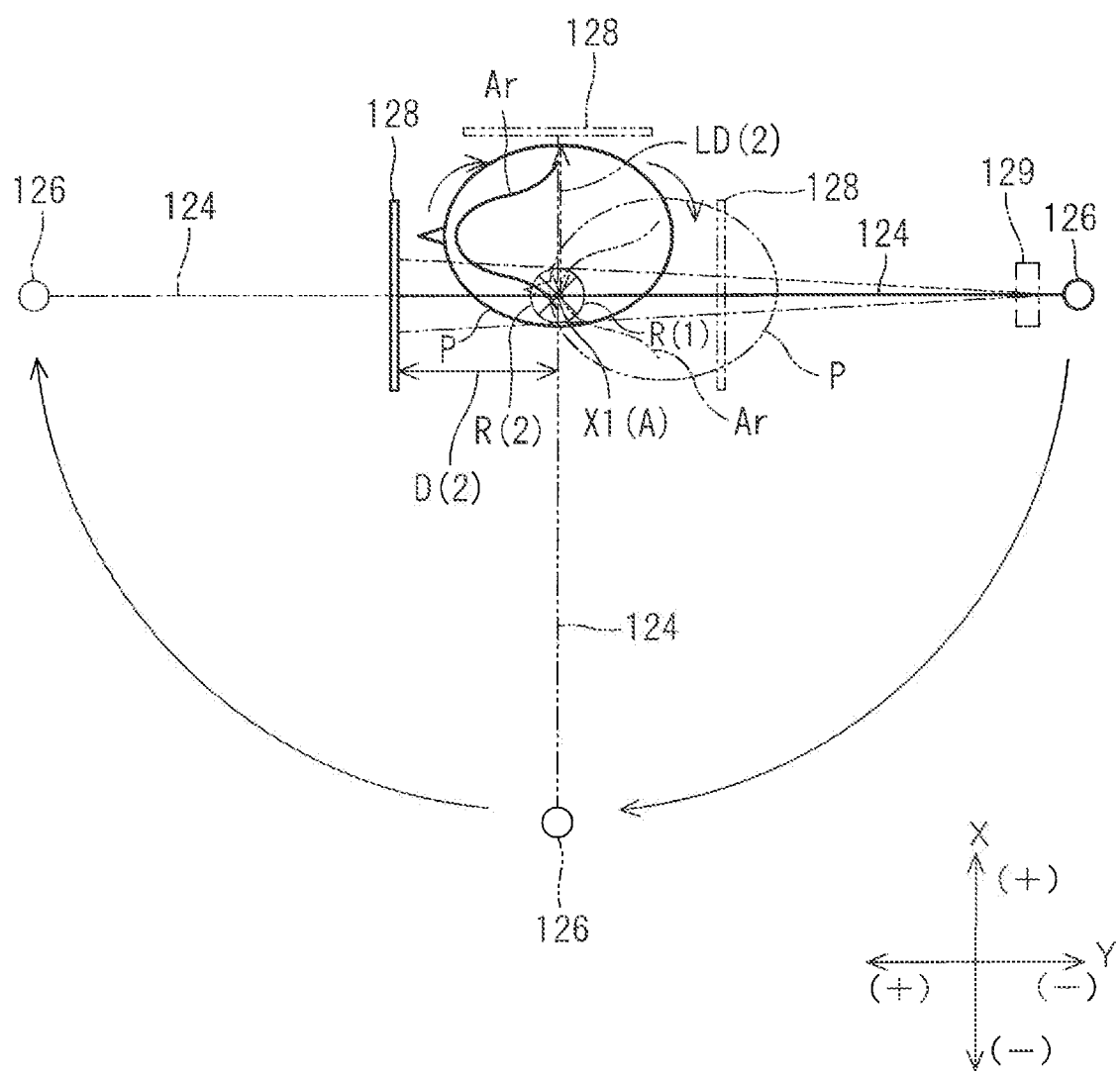
FIG. 10 is a view illustrating an example of a turning operation.
Figure 11:
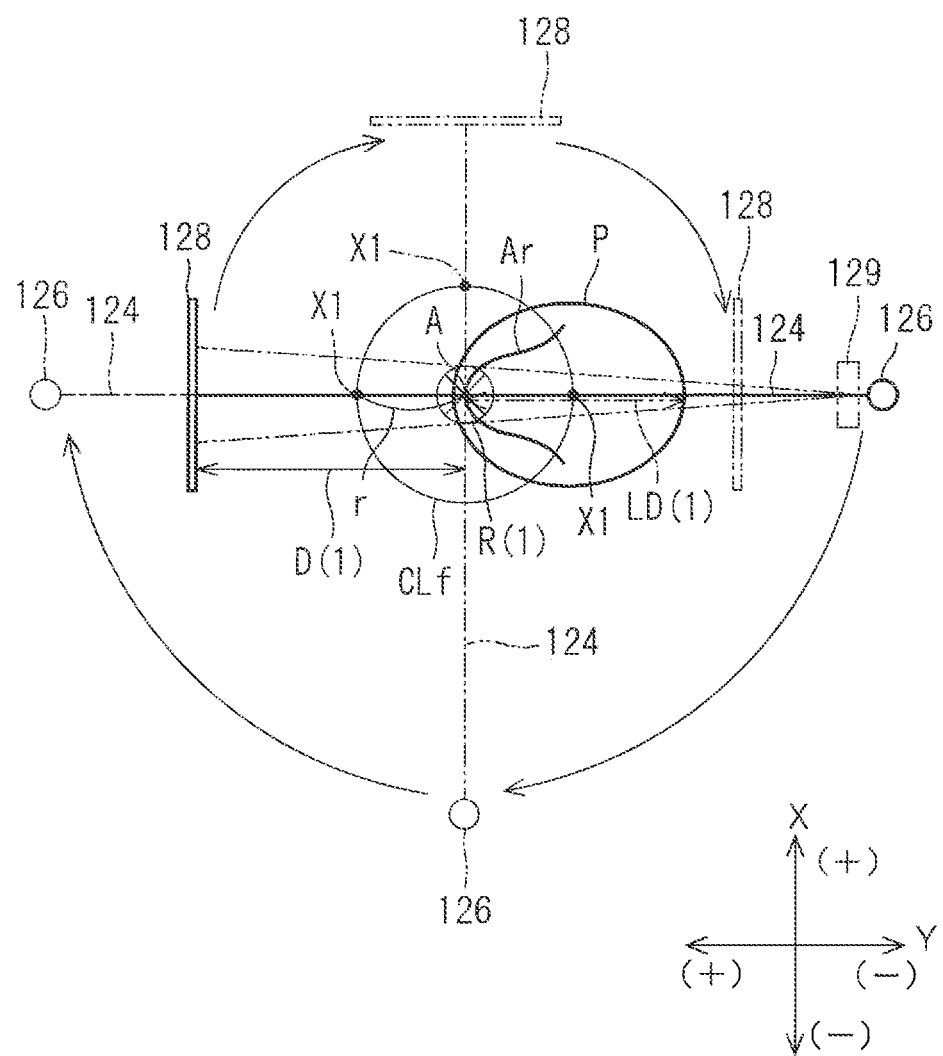
FIG. 11 is a view illustrating an example of the turning operation.

In the examples of FIGS. 10 and 11, the mechanical turning axis X1 is located closer to the X-ray detector 128 than the center position between the X-ray generator 126 and the X-ray detector 128. On the setting of the imaging orbit, the X-ray detector 128 is closer to the center A of the imaging region R than the X-ray generator 126, so the separation distance D becomes the distance between the X-ray detector 128 and the center A of the imaging region R.

The configuration in which the mechanical turning axis X1 is provided at the position closer to the X-ray detector 128 than the center position between the X-ray generator 126 and the X-ray detector 128 satisfies the following two requirements. The first requirement is to bring the X-ray detector 128 as close as possible to the imaging region R in order to reduce the magnification as much as possible to clear the projected image. The second requirement is to minimize the movement amount of the mechanical turning axis X1 during the X-ray imaging. Panoramic imaging is taken as an example. With the above configuration, during the X-ray imaging, when viewed from the direction parallel to the axial direction of the mechanical turning axis X1 (or when viewed from the body axis direction), the X-ray detector 128 is disposed near the dental arch and the mechanical turning axis X1 is arranged near the dental arch, which allows the movement amount of the mechanical turning axis X1 can be reduced.

In the example of FIG. 10, the molar region on one side that is the local part of a dental arch Ar is designated as the imaging region R. In the example of FIG. 11, the front tooth region that is the local part of the dental arch Ar is designated as the imaging region R. The region of the front tooth is set to a first imaging region R(1), and the region of the molar tooth is set to a second imaging region R(2). For convenience, FIGS. 10 and 11 illustrate the range in which the turning support 124 is turned by 180 degrees. However, the turning support 124 is rotated by 360 degrees by drawing a similar trajectory. The CT imaging may be performed by rotating the turning support 124 by 180 degrees. This case will also be described in a later modification.

It is assumed that LD is the maximum distance of the imaging region R with respect to the surface of the head P. When the front tooth region is set to the first imaging region R(1), because the front tooth region is located closer to the front of the head P, the rear surface of the head P is farthest from the first imaging region R(1), and the distance between the center A of the first imaging region R(1) and the rear surface of the head P becomes the maximum distance LD(1) (see FIG. 11). When the molar region is set to the second imaging region R(2), the molar region is located closer to the center in the front-back direction of the head P and closer to one side in the width direction. For this reason, the side surface on the other side of the head P is farthest from the second imaging region R(2), and the distance between the center A of the second imaging region R(2) and the rear surface of the head P becomes the maximum distance LD(2) (see FIG. 10). Since the head P has a shape similar to an elliptical shape that is long in the front-back direction, the maximum distance LD(1) in the case where the front tooth is set to the first imaging region R(1) is usually larger than the maximum distance LD(2) in the case where the molar region is set to the second imaging region R(2). Thus, in the case where the front tooth is set to the first imaging region R(1), the X-ray generator 126 or the X-ray detector 128 closer to the imaging region is turned outside as compared with the case where the molar region is set to the second imaging region R(2).

For this reason, when the X-ray CT imaging is performed with the molar region set to the second imaging region R(2), as illustrated in FIG. 10, the turning support 124 is turned with the mechanical turning axis X1 matched with the center A of the second imaging region R(2). In this case, the distance between the center A and the X-ray detector 128 is the separation distance D(2). In this case, the separation distance D(2) is identical to the distance between the mechanical turning axis X1 and the X-ray detector 128.

When the X-ray generator 126 and the X-ray detector 128 are turned along the same trajectory while the front tooth region is set to the first imaging region R(1), the X-ray detector 128 is in danger of the contact with the head P. When the X-ray generator 126 and the X-ray detector 128 are turned along the same trajectory, the head P is indicated by the two-dot chain line in FIG. 10. The second imaging region R(2) for the head P indicated by the solid line is the first imaging region R(1) for the head P indicated by the two-dot chain line (see FIG. 11). For the head P indicated by the two-dot chain line, it can be seen that the X-ray detector 128 is in danger of the contact with the head P when coming to the −Y-side.

For this reason, when the X-ray CT imaging is performed with the front tooth region as the first imaging region R(1), as illustrated in FIG. 11, the turning support 124 is turned about the mechanical turning axis X1 while the mechanical turning axis X1 is turned with the radius r about the center A of the first imaging region R(1). That is, the mechanical turning axis X1 moves on a circular orbit CLf having the radius r. In this case the distance between the center A and the X-ray detector 128 is the separation distance D (1). In order to move the X-ray detector 128 away from the center A of the imaging region R, the mechanical turning axis X1 is moved away from the center A of the imaging region R toward the X-ray detector side. That is, the mechanical turning axis X1 moves on the circular orbit CLf while being located between the center A and the X-ray detector 128. The separation distance D(1) has a value obtained by adding the radius r to the distance between the mechanical turning axis X1 and the X-ray detector 128.

In this case, the X-ray generator 126 turns while drawing a radius smaller than the case in FIG. 10. The X-ray detector 128 turns while drawing a radius larger than the case in FIG. 10. The relationship between the orbit of the X-ray generator 126 and the orbit of the X-ray detector 128 in FIG. 11 are closer to each other than that in FIG. 10. For this reason, the X-ray generator 126 and the X-ray detector 128 can rotate about the head P without contacting with the head P.

At this point, in order to describe a more specific control example, the coordinate of the mechanical turning axis X1 is temporarily considered while leaving FIG. 11. For example, it is assumed that (X(a), Y(a)) are coordinates of X and Y in the XYZ-coordinate system of the center A of the imaging region R, and that $\theta$ is a turning angle of the turning support 124 rotated by the turning mechanism 132 (an angle at which the X-ray generator 126 and the X-ray detector 128 rotate clockwise from the state in which the X-ray generator 126 is provided on the +X-side while the X-ray detector (and the turning axis X1) is provided on the −X-side). The turning mechanism 132 and the turning axis moving mechanism 134 are controlled such that the X-direction drive unit 136 sets the X-coordinate of the mechanical turning axis X1 to "$X(a)−r \cos \theta$", and such that the Y-direction drive unit 138 sets the Y-coordinate of the mechanical turning axis X1 to "$Y(a)+r \sin \theta$". The control content can similarly be applied to the following modifications in which the mechanical turning axis X1 is turned.

By turning the X-ray generator 126 and the X-ray detector 128 around the imaging region R of the head P, the X-ray image data necessary for the generation of the X-ray CT image of the imaging region R is obtained, and the X-ray CT image is generated based on the obtained data.

<Effect>

According to the X-ray CT imaging apparatus 110 configured as described above and the control method thereof, the position of the turning axis X1 is controlled according to the position of the imaging region R set by the imaging region position setting unit 151a and the like. Consequently, the trajectories of the X-ray generator 126 and the X-ray detector 128 can be controlled according to the position, and the X-ray generator 126 and the X-ray detector 128, which turn about the head P, can be prevented from contacting with the subject.

The head P is usually long in the front-back direction. For this reason, when the X-ray CT imaging is performed on the front tooth of the dental arch Ar as the imaging region R, the distance between the front tooth and the rear portion of the head P is lengthened, and the X-ray generator 126 or the X-ray detector 128 contacts easily with the head. On the other hand, when the X-ray CT imaging is performed on the molar tooth of the dental arch Ar as the imaging region R, the distance between the molar tooth and the side or rear portion of the head P is relatively shortened. For this reason, in the case where the X-ray CT imaging is performed on the molar tooth, when the position of the turning axis X1 is controlled such that one of the X-ray generator 126 and the X-ray detector 128 that is closer to the center A of the imaging region R (in this case, the X-ray detector 128) passes through the trajectory closer to the center A of the imaging region R than the X-ray generator 126 or the X-ray detector 128 closer to the center A of the imaging region R when the X-ray CT imaging is performed on the front tooth, the X-ray generator 126 and the X-ray detector 128, which turn about the head P, can be prevented from contacting with the head P.

The position of the mechanical turning axis X1 with respect to the center A of the imaging region R is changed such that the separation distances D(1), D(2), which is smaller one of the distance between the center A of the imaging region R and the X-ray generator 126 and the distance between the center A of the imaging region R and the X-ray detector 128, is larger than the maximum distance LD(1), LD(2) of the surface of the head P with respect to the center A of the imaging region R. Consequently, the X-ray generator 126 and the X-ray detector 128, which turn about the head P, can be prevented from contacting with the head P.

The turning trajectory of the X-ray detector 128 is changed according to the position of the imaging region R, so that the X-ray CT imaging can be performed by bringing the X-ray detector 128 as close as possible to the head P while the contact between the X-ray detector 128 and the head P is prevented. Consequently, the clear X-ray image can be generated.

As a more specific example, the imaging region position setting unit 151a can receive the first imaging region R(1) and the second imaging region R(2) where the maximum distance LD(2) is smaller than the maximum distance LD(1) of the first imaging region R(1) as the imaging region R. Then, the position of the mechanical turning axis X1 with respect to the center A of the imaging region R is changed such that the separation distance D(1) in the case where the imaging region R is the first imaging region R(1) according to the positions of the imaging regions R(1), R(2) set by the imaging region position setting unit 151a is larger than the separation distance D(2) in the case where the imaging region R is the second imaging region R(2). Consequently, the X-ray generator 126 and the X-ray detector 128 can be prevented from contacting with the head P.

In this case, the position of the mechanical turning axis X1 with respect to the center A of the first imaging region R(1) is changed to cause the turning support 124 to perform the combined motion such that the position of the mechanical turning axis X1 is separated from the center A of the first imaging region R(1) when the imaging region R is the first imaging region R(1). This enables the separation distance D(1) to be increased to prevent the X-ray generator 126 and the X-ray detector 128, which turn about the head P, from contacting with the head P. When the imaging region R is the second imaging region R(2), the mechanical turning axis X1 is fixed to the position of the center A of the second imaging region R(2). Consequently, the X-ray detector 128 can be turned as close as possible to the head P while the X-ray generator 126 and the X-ray detector 128, which turn about the head P, are prevented from contacting with the head P.

As described above, the turning axis moving mechanism 134 moves the mechanical turning axis X1 in synchronization with the turning of the turning support 124 about the mechanical turning axis X1 using the turning mechanism 132, and the turning support 124 is caused to perform the combined motion, which allows the turning axis moving mechanism 134 to turn the mechanical turning axis X1 about the center A of the imaging region R when the X-ray generator 126 and the X-ray detector 128 are turned about the center A of the imaging region R. For this reason, even when the mechanical turning axis X1 is moved during the performance of the X-ray CT imaging, the X-ray generator 126 and the X-ray detector 128 are turned along the orbit as close as possible to the circle, and a magnification ratio can be kept constant as much as possible.

When the mechanical turning axis X1 is matched with the center A of the second imaging region R(2) as in the case where the imaging region R is the second imaging region R(2), the actual turning centers of the X-ray generator 126 and the X-ray detector 128 can be set to the center A of the imaging region R. Consequently, accuracy of the turning of the imaging system including the X-ray generator 126 and the X-ray detector 128 can be enhanced.

The X-ray CT imaging can be performed while the distance between the X-ray generator 126 and the center of the imaging region R and the distance between the X-ray detector 128 and the center A of the imaging region R are kept constant when the X-ray CT imaging is performed by irradiating the head P with the X-ray generated from the X-ray generator 126.

The mechanical turning axis X1 is set at the position closer to the X-ray detector 128 than to the X-ray generator 126. For this reason, the X-ray detector 128 turns near the imaging region R, and the X-ray CT image can be made as clear as possible.

<Modifications>

Modifications will be described below based on the first embodiment or the second embodiment.

In the examples in FIGS. 10 and 11, the description is mainly made on the assumption that the X-ray generator 126 and the X-ray detector 128 turn by 360 degrees. However, sometimes the CT imaging is performed while the X-ray generator 126 and the X-ray detector 128 turn by less than 360 degrees, for example, 180 degrees.

Also in this case, the position of the turning axis X1 may be controlled when the X-ray CT imaging is performed on the local part of the dental arch Ar according to the set position of the imaging region R. More specifically, the position of the mechanical turning axis X1 with respect to the center A of the imaging region R is controlled such that the separation distance D is larger than the maximum distance LD according to the set position of the imaging region R. At this point, the separation distance D is a smaller one of the distance between the center A of the imaging region R and the X-ray generator 126 and the distance between the center A of the imaging region R and the X-ray detector 128. The maximum distance LD is the maximum distance of the surface of the head P with respect to the center A of the imaging region R in the turning range of the X-ray generator 126 or the X-ray detector 128 closer to the center A of the imaging region R.

Figure 12:
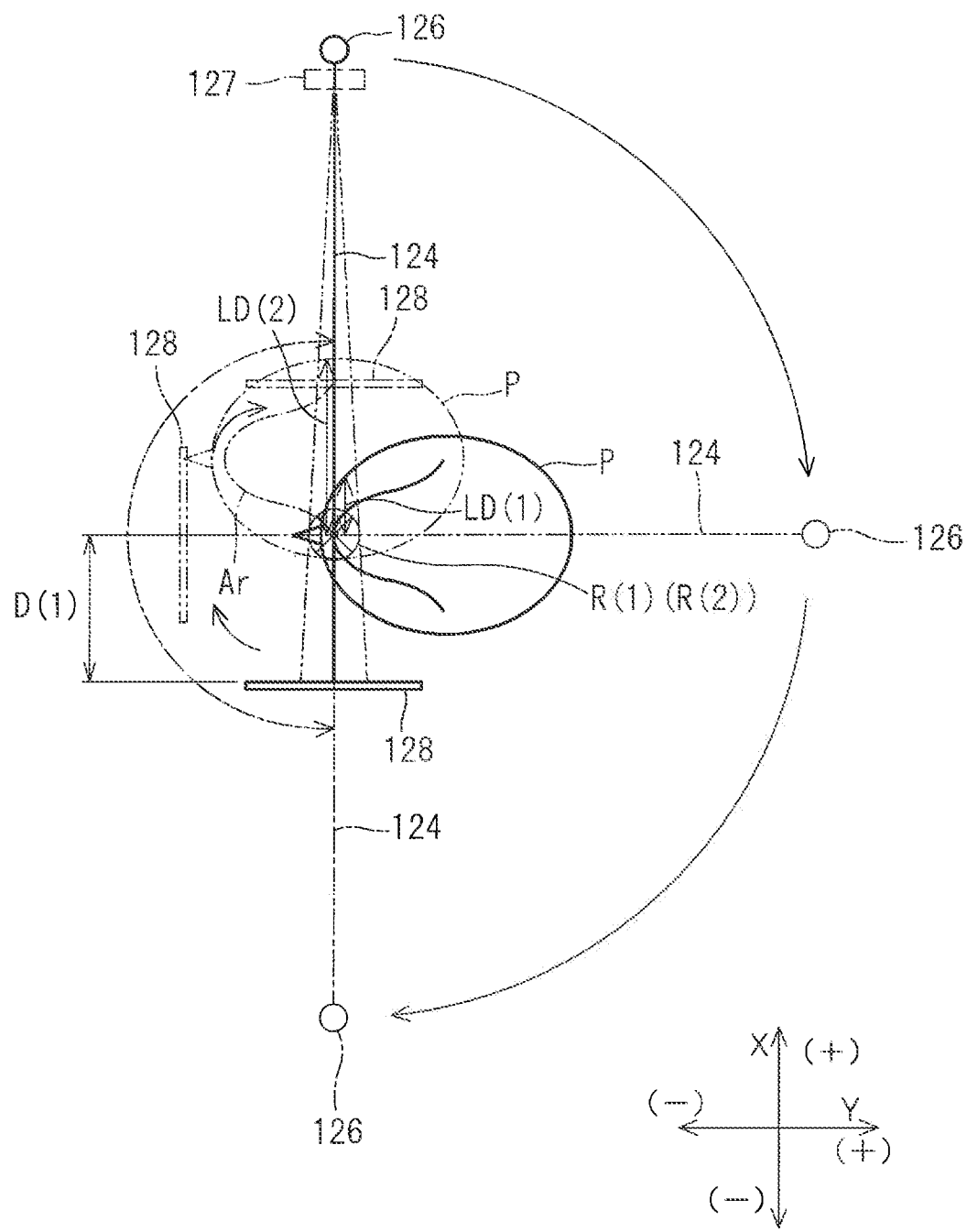
FIG. 12 is a view illustrating an example of the turning operation according to a modification.
Figure 13:
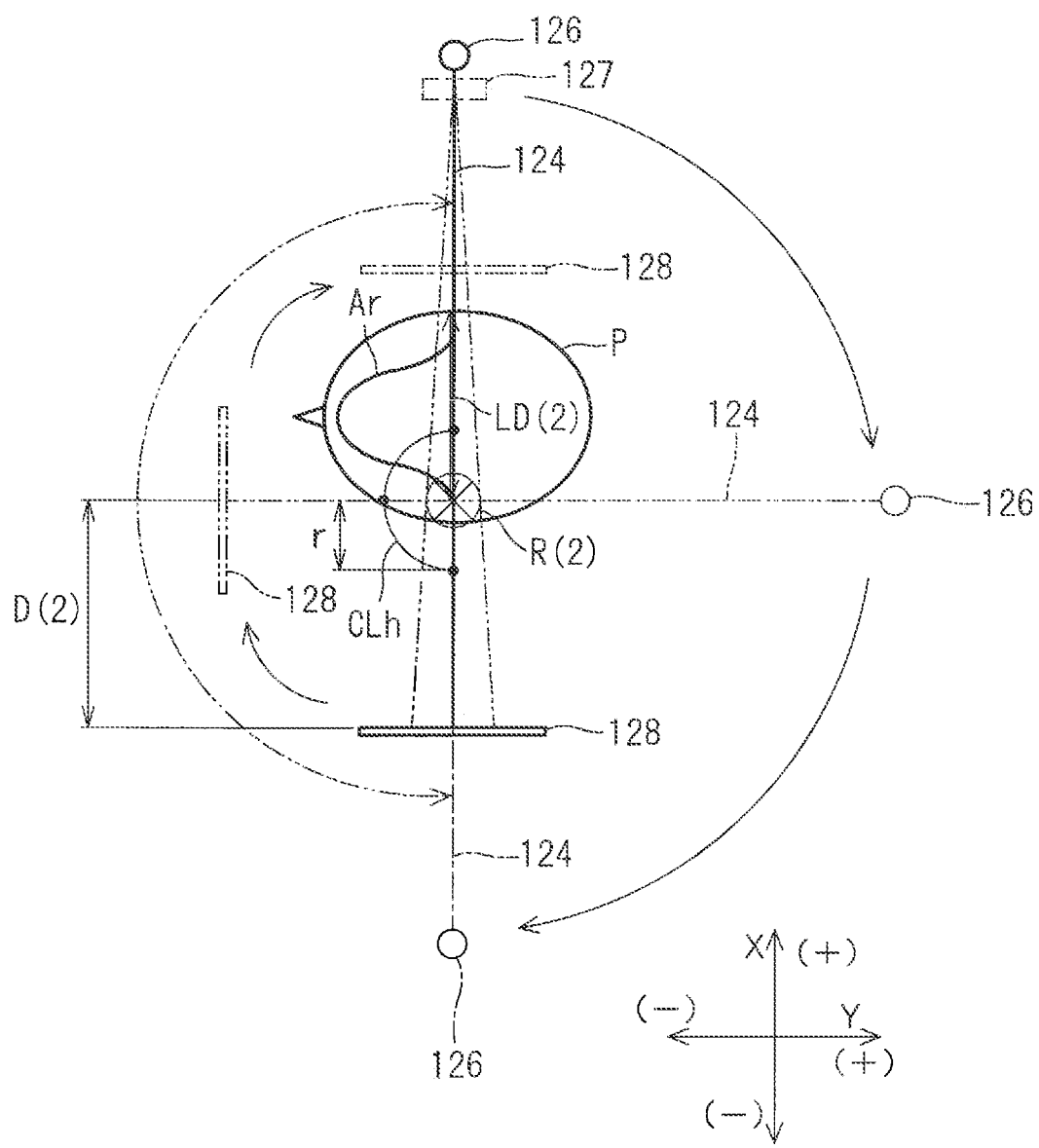
FIG. 13 is a view illustrating an example of the turning operation of the modification.

For example, as illustrated in FIGS. 12 and 13, it is assumed that the X-ray detector 128 turns about the imaging region R so as to pass from one side of the head P toward the other side through the front. The X-ray generator 126 turns about the imaging region R so as to pass from the other side of the head P to one side through the rear.

First, the case where the position of the imaging region R(1) is the front tooth of the dental arch Ar is considered as illustrated in FIG. 12. In the example of FIG. 12, the X-ray detector 128 turns closer to the center A of the imaging region R(1) than the X-ray generator 126. The turning range of the X-ray detector 128 turns by 180 degrees in both the left and right directions around the front of the head P. The maximum distance LD(1) of the surface of the head P with respect to the center A of the imaging region R(1) in the turning range becomes the distance between the center A and the side portion of the head P. The trajectory in which the X-ray detector 128 passes through the rear of the head is avoided by setting the orbits of the X-ray generator 126 and the X-ray detector 128 in this way.

Therefore, the position of the mechanical turning axis X1 with respect to the center A of the imaging region R is set such that the separation distance D(1) is larger than the maximum distance LD(1).

In this case, the turning support 124 is turned while the mechanical turning axis X1 is matched with the center A of the imaging region R(1). In this case the distance between the center A and the X-ray detector 128 is the separation distance D (1). In this case, the separation distance D(1) is identical to the distance between the mechanical turning axis X1 and the X-ray detector 128.

Consequently, the X-ray detector 128 can be turned about the imaging region R(1) while the contact of the X-ray detector 128 with the head P is avoided. At this point, while the X-ray detector 128 is brought closer to the imaging region R(1), the more stable turning can be obtained by placing the turning axis X1 at one place, and the clear X-ray CT image can be obtained.

On the other hand, the case where the position of the imaging region R(2) is set to the molar tooth of the dental arch Ar is considered as illustrated the head P indicated by the two-dot chain line in FIG. 12. In this case, the maximum distance LD(2) of the surface of the head P with respect to the center A of the imaging region R(2) in the turning range of the X-ray detector 128 becomes the distance between the center A and one of the side portions of the head P farther from the center A. The maximum distance LD(2) is larger than the maximum distance LD(1). For this reason, the X-ray detector 128 is in danger of the contact with the head P when being turned on the same turning trajectory.

Therefore, as illustrated in FIG. 13, the position of the mechanical turning axis X1 with respect to the center A of the imaging region R is set such that the separation distance D(2) is larger than the maximum distance LD(2).

In this case, the turning support 124 is turned about the mechanical turning axis X1 while the mechanical turning axis X1 is turned with the radius r about the center A of the imaging region R(2). That is, the mechanical turning axis X1 moves on a semicircular orbit CLh having the radius r. The turning axis X1 moves on the semicircular orbit CLh while being located between the center A and the X-ray detector 128. In this case, the distance between the center A and the X-ray detector 128 is the separation distance D(2). At this point, the separation distance D(2) is a value obtained by adding the radius r to the distance between the mechanical turning axis X1 and the X-ray detector 128. Compared with the case in FIG. 12, the separation distance D(2) becomes the value obtained by adding the radius r to the separation distance D(1).

Consequently, the X-ray detector 128 can be turned about the imaging region R(2) while the X-ray detector 128 is prevented from contacting with the head P. At this point, the X-ray detector 128 can be brought as close as possible to the imaging region R(2), and the clear X-ray CT image can be obtained.

In this modification, the X-ray generator 126 and the X-ray detector 128 are rotated by less than 360° (preferably, 270° or less, in this case, 180°), so that one of the X-ray generator 126 and the X-ray detector 128 that is closer to the center A of the imaging region R (in this case, the X-ray detector 128) can be prevented from turning behind the head P. Thus, in the range in which one of the X-ray generator 126 and the X-ray detector 128 that is closer to the center A of the imaging region R turns, the position of the turning axis X1 is controlled such that the X-ray generator 126 and the X-ray detector 128 do not contact with the head P.

At this point, it is assumed that the X-ray detector 128 is closer to the center A of the imaging region R than the X-ray generator 126, and that the X-ray detector 128 turns in a first half of the head P. In this case, the position of the turning axis X1 is controlled such that the X-ray detector 128 in the case where the X-ray CT imaging is performed on the front tooth turns at the position farther from the center A of the imaging region R than the X-ray detector 128 in the case where the X-ray CT imaging is performed on the molar tooth.

In the second embodiment and the modification, by way of example, the case where the mechanical turning axis X1 is fixed to the position of the center A of the imaging region R and the case where the turning axis X1 is turned about the center A are switched to control the position of the turning axis X1. However, the position of the turning axis X1 may be controlled in another way.

Figure 14:
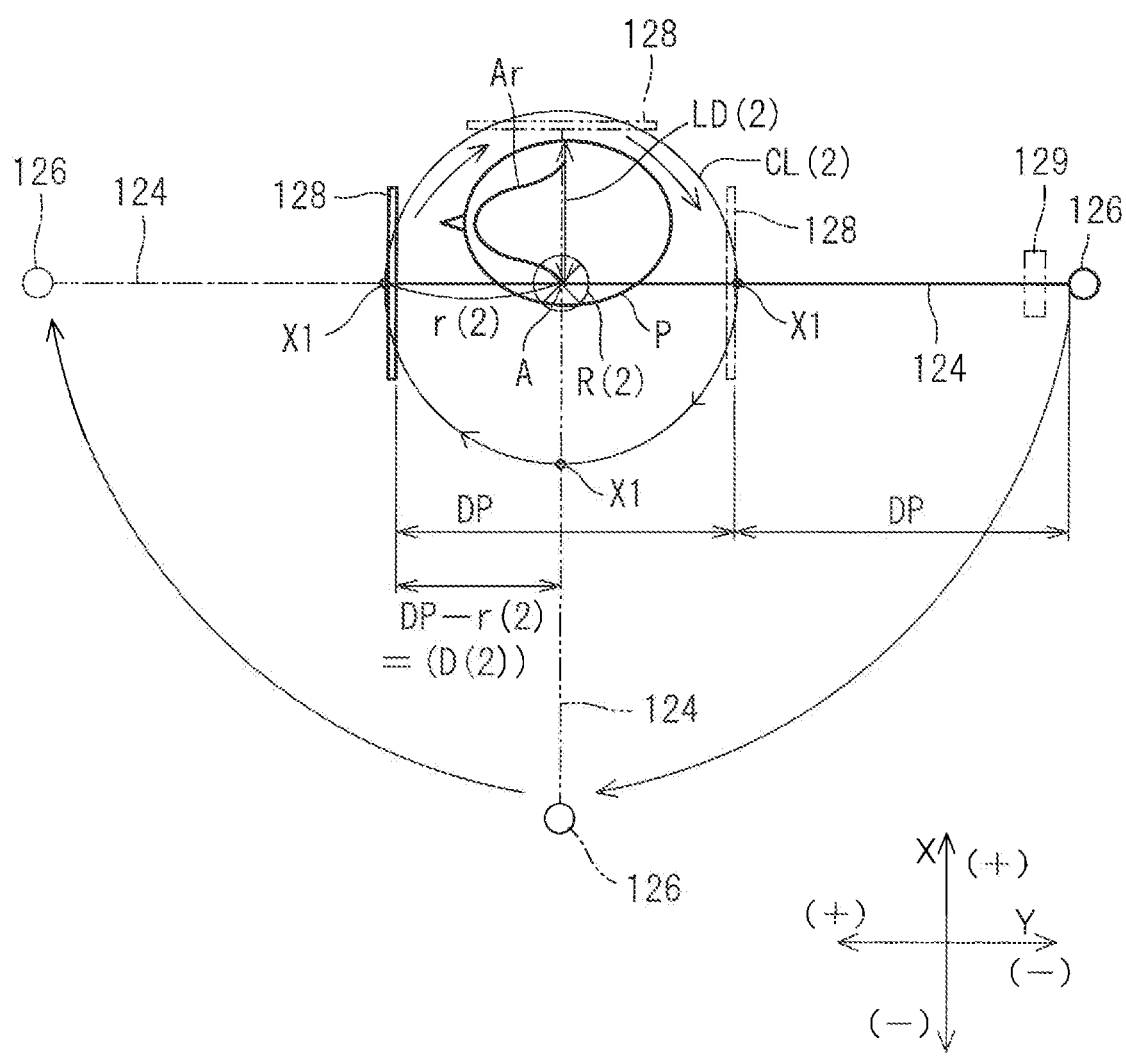
FIG. 14 is a view illustrating an example of the turning operation according to another modification.
Figure 15:
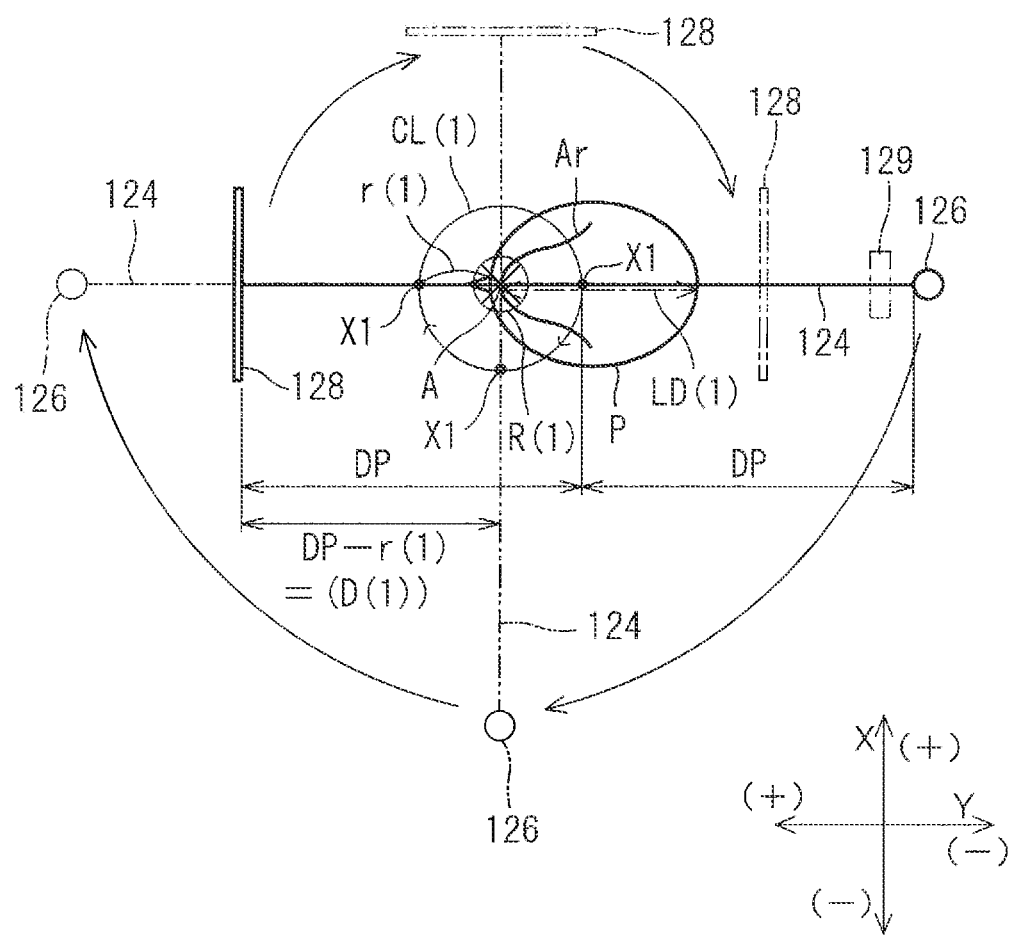
FIG. 15 is a view illustrating an example of the turning operation of another modification.

In a modification of FIGS. 14 and 15, the distance between the mechanical turning axis X1 and the center A of the imaging region R is changed according to the position of the imaging region R when the turning support 124 is caused to perform the combined motion. That is, in the modification, when the molar tooth (the imaging region R(2) where the maximum distance LD(2) is relatively small) is set, and when the front tooth (the imaging region R(1) where the maximum distance LD(1) is relatively large) is set, the position of the mechanical turning axis X1 with respect to the center A of the imaging region R is controlled such that the position of the mechanical turning axis X1 is separated from the center A of the imaging regions R(1), R(2).

FIG. 14 is an explanatory view illustrating the turning operation when the molar tooth (the imaging region R(2) where the maximum distance LD(2) is relatively small) is set, and FIG. 15 is an explanatory view illustrating the turning operation when the front tooth (the imaging region R(1) where the maximum distance LD(1) is relatively large). In the first modification, the mechanical turning axis X1 is located at the central position between the X-ray generator 126 and the X-ray detector 128. For this reason, the distance of the X-ray generator 126 to the mechanical turning axis X1 and the distance of the X-ray detector 128 to the turning axis X1 are equal to each other. For convenience, FIGS. 14 and 15 illustrate the range in which the turning support 124 is turned by 180 degrees. However, the turning support 124 is rotated by 360 degrees by drawing a similar trajectory. The CT imaging may be performed by rotating the turning support 124 by 180 degrees.

When the molar region is set to the imaging region R(2), the maximum distance LD(2) becomes relatively small. In this case, as illustrated in FIG. 14, the turning support 124 is turned about the mechanical turning axis X1 while the mechanical turning axis X1 is turned with a radius r(2) about the center A of the imaging region R(2). More specifically, the mechanical turning axis X1 is turned with the radius r(2) about the center A of the imaging region R by the turning axis moving mechanism 134 in synchronization with the turning of the turning support 124 about the mechanical turning axis X1 using the turning mechanism 132. That is, the mechanical turning axis X1 moves on a circular orbit CL(2) having the radius r(2). In the modification, in order to bring the X-ray detector 128 closer to the center A of the imaging region R, the mechanical turning axis X1 is moved toward the side of the X-ray generator 126. That is, the mechanical turning axis X1 turns about the center A of the imaging region R while being located between the center A of the imaging region R and the X-ray generator 126.

When the CT imaging is performed by turning the X-ray generator 126 and the X-ray detector 128 while the mechanical turning axis X1 is matched with the center A of the imaging region R, the X-ray detector 128 is largely separated from the imaging region R. When the X-ray detector 128 is brought as close as possible to the imaging region R to perform the imaging while the contact with the head P is avoided, the orbit in FIG. 14 is preferably used.

In this case, assuming that DP is the distance of the X-ray generator 126 to the mechanical turning axis X1 and the distance of the X-ray detector 128 to the turning axis X1, the distance between the center A of the imaging region R and the X-ray generator 126 during the turning is distance DP+radius r(2), and is kept constant. The distance between the center A of the imaging region R and the X-ray detector 128 during the turning is distance DP−radius r(2), and is kept constant. Distance DP−radius r(2), which is smaller one, becomes the separation distance D(2). The separation distance D(2) is set to be larger than the maximum distance LD(2) in the direction orthogonal to the turning axis X1. Consequently, the X-ray detector 128 can turn about the head P without contacting with the head P when the imaging region R(2) where the maximum distance LD(2) is relatively small is set. The X-ray generator 126 turns at the position farther from the X-ray detector 128 with respect to the center A of the imaging region R, so that the X-ray generator 126 can also turn about the head P without contacting with the head P that is the subject.

In the case where the imaging region R(1) where the maximum distance LD(1) is relatively large is set, the X-ray detector 128 possibly contacts with the rear portion of the head P when the X-ray detector 128 turns in the same manner as described above.

For this reason, in the example of FIG. 15, the turning support 124 is turned about the mechanical turning axis X1 while the mechanical turning axis X1 is turned with a radius r(1) about the center A of the imaging region R. More specifically, the turning axis moving mechanism 134 turns the mechanical turning axis X1 with the radius r(1) about the center A of the imaging region R in synchronization with the turning of the turning support 124 about the mechanical turning axis X1 using the turning mechanism 132. At this point, radius r(1)<radius r(2) holds. The mechanical turning axis X1 moves on a circular orbit CL(1) having the radius r(1). Also in the modification, the mechanical turning axis X1 turns about the center A of the imaging region R while being located between the center A of the imaging region R and the X-ray generator 126.

The orbit in FIG. 15 is preferably used when the X-ray detector 128 is brought as close as possible to the imaging region R to perform the imaging while the contact with the head P is avoided.

In this case, the distance between the center A of the imaging region R and the X-ray generator 126 during the turning is distance DP+radius r(1), and is kept constant. The distance between the center A of the imaging region R and the X-ray detector 128 during the turning is distance DP−radius r(1), and is kept constant. Distance DP−radius r(1), which is the smaller one, becomes the separation distance D(1). Because of radius r(1)<radius r(2), the separation distance D(1) is larger than the separation distance D(2). The separation distance D(1) is set to larger than the maximum distance LD(1) in the direction orthogonal to the turning axis X1. For this reason, the X-ray detector 128 can turn about the head P without contacting with the head P when the maximum distance LD(1) is set to the relatively large imaging region R(1). The X-ray generator 126 turns at the position farther from the X-ray detector 128 with respect to the center A of the imaging region R, so that the X-ray generator 126 can also turn about the head P without contacting with the head P that is the subject.

In this way, when the molar tooth (the imaging region R(2) where the maximum distance LD(2) is relatively small)

is set, and when the front tooth (the imaging region R(1) where the maximum distance LD(1) is relatively large) is set, the mechanical turning axis X1 may be separated from the center A of the imaging region R. In this case, the magnitude relationship between the radii r(1) and r(2) may be reversed depending on the positional relationship of the turning axis X1 between the X-ray generator 126 and the X-ray detector 128.

As described in the second embodiment, the turning support 124 may be turned about the mechanical turning axis X1 while the mechanical turning axis X1 is turned with the radius r about the center A of the imaging region R when the imaging region R(2) where the maximum distance LD(2) is relatively small is set, and the turning support 124 may be turned while the mechanical turning axis X1 is matched with the center A of the imaging region R when the imaging region R(1) where the maximum distance LD(1) is relatively large is set. For example, in the case where the mechanical turning axis X1 is located at or near the central position between the X-ray generator 126 and the X-ray detector 128 as in the modification, the turning support 124 may be turned while the mechanical turning axis X1 is matched with the center A of the imaging region R when the imaging region R(1) where the maximum distance LD(1) is relatively large is set.

Third Embodiment

An X-ray CT imaging apparatus according to a third embodiment will be described. In the description of the third embodiment, the same components as those described in the second embodiment are denoted by the same reference numerals, and description thereof will be omitted.

FIG. 16 is a block diagram illustrating an electric configuration of an X-ray CT imaging apparatus 210. The X-ray CT imaging apparatus 210 of the third embodiment is mounted on the apparatus having the same configuration as the X-ray CT imaging apparatus 110 of the second embodiment.

The X-ray CT imaging apparatus 210 is different from the X-ray CT imaging apparatus 110 in that the X-ray CT imaging apparatus 210 includes a subject physique setting unit 251a (hereinafter, abbreviated to a physique setting unit 251a), and that an imaging program 253a corresponding to the imaging program 153a includes processing of controlling the position of the mechanical turning axis X1 with respect to the center A of the imaging region R according to the size of the physique of the subject set by the physique setting unit 251a. Thus, based on the imaging program 253a, a turning controller 251b corresponding to the turning controller 151b controls the position of the mechanical turning axis X1 with respect to the center A of the imaging region R according to the size of the physique of the subject set by the physique setting unit 251a. For example, the turning controller 251b changes the position of the mechanical turning axis X1 with respect to the center A of the imaging region R such that the separation distance D in the case where the set physique of the subject is the first physique is larger than the separation distance D in the case where the set physique of the subject is the second physique smaller than the first physique according to the size of the physique of the subject set by the physique setting unit 251a.

As described in the first embodiment or the second embodiment, an example of the position control of the turning axis X1 according to the size of the physique of the subject is performed by switching between the drive control in which the turning support 124 is caused to perform the combined motion and the drive control in which the turning support 124 is turned while the turning axis X1 is fixed to the position of the center A of the imaging region R according to the size of the physique of the subject. Alternatively, the position of the turning axis X1 may be controlled by changing the distance between the turning axis X1 and the center A of the imaging region R according to the size of the physique of the subject when the turning support 124 is caused to perform the combined motion.

FIG. 17 is a flowchart illustrating processing performed by the turning controller 251b.

That is, when the X-ray CT imaging is performed, in step S21, the setting of the size of the imaging region R is received through the imaging region position setting unit 151a. The setting of the size of the imaging region R can be received in the same manner as described in the second embodiment. As illustrated in FIG. 8, when the operator touches the imaging region setting image 194, the plurality of imaging region selection images 194a, 194b, 194c, 194d, 194e corresponding to the imaging region setting image 194 are displayed according to the touch operation. The X-ray CT imaging targeting the local part of the dental arch is received when one of the imaging region selection images 194a, 194b is touched. The X-ray CT imaging targeting the whole of the dental arch is received when one of the imaging region selection images 194c, 194d, 194e is touched.

In step S22, whether the X-ray CT imaging targeting the local part of the dental arch or the X-ray CT imaging targeting the whole of the dental arch is selected is determined according to the setting reception of the size of the imaging region R received in step S21. The processing proceeds to step S23 when the X-ray CT imaging targeting the local part of the dental arch is selected, and the processing proceeds to step S29 when the X-ray CT imaging targeting the whole of the dental arch is selected.

The input setting of the physique is received in step S23.

Figure 18:
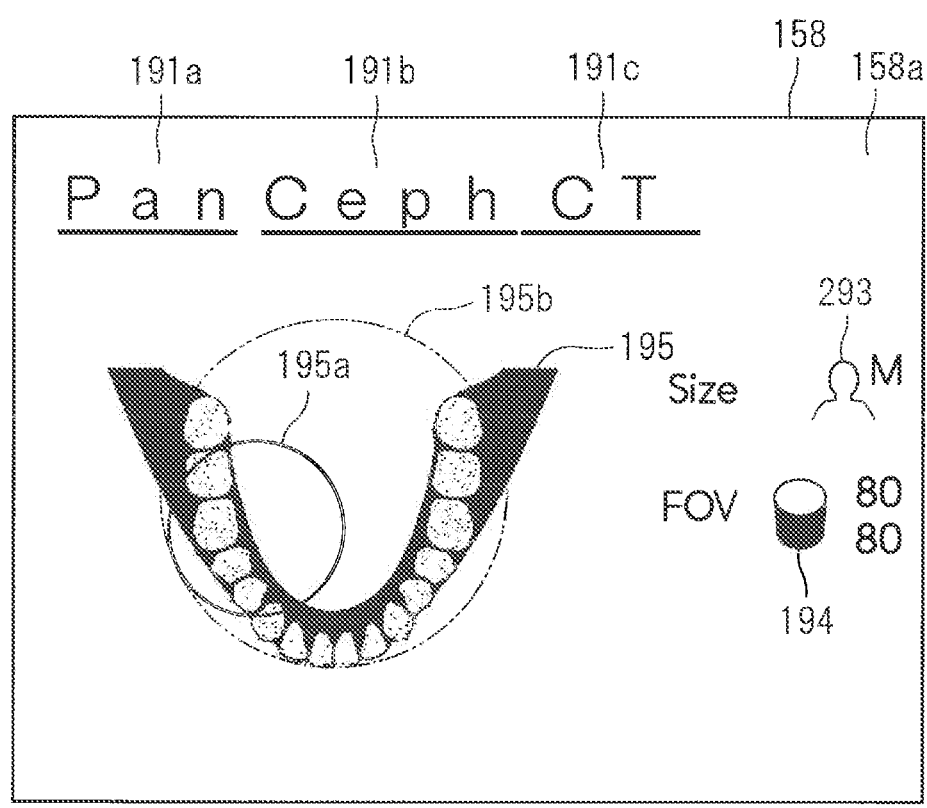
FIG. 18 is a view illustrating a display example in an operation panel apparatus.

An example of the reception of the operation to input the physique will be described. FIG. 18 illustrates a display example in which an image for receiving a physique input operation is added to the display example of the operation panel apparatus 158 described in the second embodiment. A physique setting image 293 is additionally displayed on the display 158a of the operation panel apparatus 158. In this case, the physique setting image 293 is displayed on the right side of the display 158a and above the imaging region setting image 194.

Figure 19:
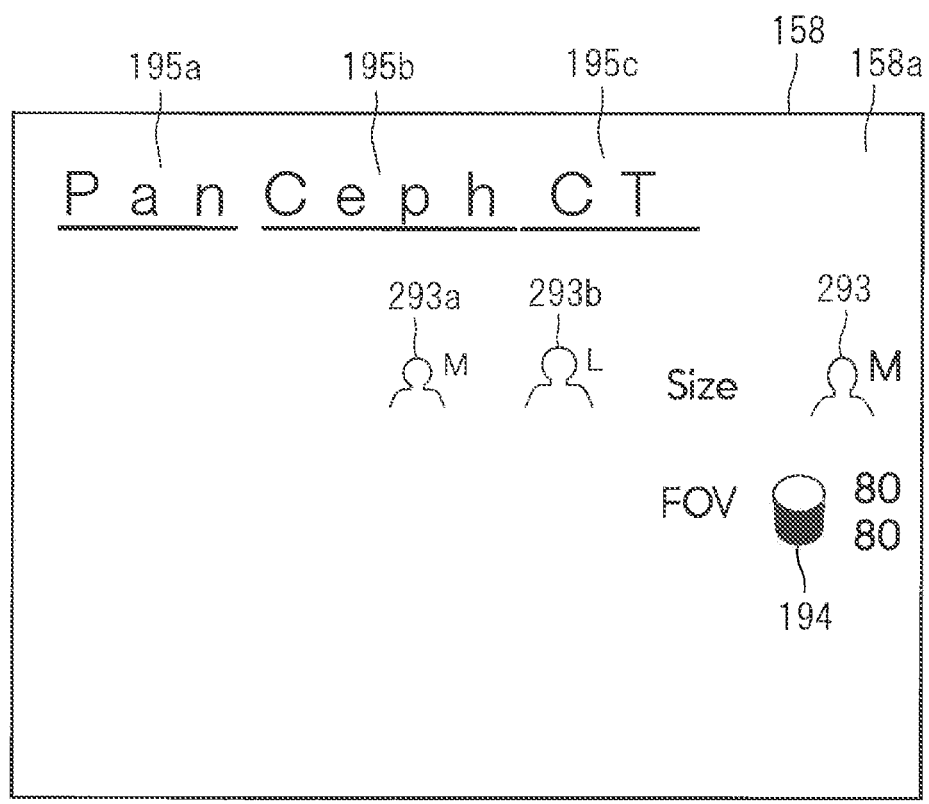
FIG. 19 is a view illustrating a display example in the operation panel apparatus.

When the operator touches the physique setting image 293, a selected image corresponding to the physique setting image 293 is displayed as shown in FIG. 19. A normal-size selection image 293a (M size) and a large-size selection image 293b (L size) are displayed as a plurality of physique selection images. The operation to input the physique of the head P that is the subject is received when the user selectively touches one of the normal-size selection image 293a and the large-size selection image 293b.

In the above example, the physique is set using the touch panel, the designation of the imaging region. Alternatively, the setting of the physique may be received through a switch (push button) that physically receives the operation.

Returning to FIG. 17, in step S24, when receiving the operation to input the physique of the head P through the operation panel apparatus 158, the physique setting unit 251a sets the physique of the head P to the turning controller 251b according to the received content. The physique setting unit 251a receives the input operation to select one of the normal-size selection image 293a and the large-size selection image 293b, which are physique sizes of a plurality of selection candidates, through the operation panel apparatus 158, thereby setting the physique of the head P. The large-size selection image 293*b* is an image for receiving the first physique, and the normal-size selection image 293*a* is an image for receiving the second physique smaller than the first physique, and the first physique and the second physique are selectively set by selecting one of the large-size selection image 293*b* and the normal-size selection image 293*a*.

The physique setting unit 251*a* may automatically recognize the physique of the head P, and set the physique. As an example in which the physique of the head P is automatically recognized, the head P that is the subject is imaged to extract the head region from the captured image and the size of the head is recognized from the extracted head region to set the physique, or a holder that holds the head P while sandwiching the head P from the left or right direction or the front-back direction is provided in the head fixing apparatus 142 that fixes the head, an opening degree of the holder is detected with a sensor or the like to recognize the physique of the head, and the physique is set.

The position setting of the imaging region R is received in step S25. The reception can be performed in the same manner as described in the second embodiment.

In step S26, the turning control content and the regulation amount are decided according to the set position of the imaging region R and the set physique. The turning control content and the regulation amount are expressed in the same manner as described in the second embodiment.

The turning control content and the regulation amount for the imaging region R can be decided in the same manner as described in the second embodiment. The third embodiment is different from the second embodiment in that the turning control content and the regulation amount are decided according to the physique of the head P.

That is, in the case where the position of the mechanical turning axis X1 is adjusted according to the position of the imaging region R on the assumption of a fixed size (standard size) of the head P, the X-ray generator 126 or the X-ray detector 128 is in danger of the contact with the head P when the physique of the head P is large. For this reason, the turning control content and the regulation amount are decided in consideration of the physique of the head P.

In this case, according to the size of the physique of the head P set in the physique setting unit 251*a*, the position of the mechanical turning axis X1 with respect to the center A of the imaging region R is changed such that the separation distance D in the case where the set physique of the head P is the first physique becomes larger than the separation distance D in the case where the set physique of the head P is the second physical physique.

For example, the turning control content and the regulation amount according to the set position of the imaging region R and the set physique can be decided by referring to a reference table in FIG. 20. That is, as in the second embodiment, the reference table in which the turning control content, the separation distance D (magnification m), and the regulation width W are associated with the position of the imaging region is previously registered. The reference table is different from the reference table of the second embodiment in that the turning control content, the separation distance D (magnification m), and the regulation width W are associated with not only the position of the imaging region but also the physique.

In the example of FIG. 20, the same table as that in FIG. 9 is set for each of the normal physique P(M) and the large physique P(L).

The turning of the mechanical turning axis X1 with a radius r(M1) about the center A of the imaging region R, the separation distance D(M1) (magnification m(M1)), and the regulation width W(M1) are associated with the case where the position of the imaging region R is the front tooth for the normal physique P(M) as the turning control content. The turning of the mechanical turning axis X1 with the mechanical turning axis X1 matched with the center A of the imaging region R, the separation distance D(M2) (magnification m(M2)), and the regulation width W(M2) are associated with the case where the position of the imaging region R is the molar tooth for the normal physique P(M) as the turning control content.

The turning of the mechanical turning axis X1 with a radius r(L1) about the center A of the imaging region R, the separation distance D(L1) (magnification m(L1)), and the regulation width W(L1) are associated with the case where the position of the imaging region R is the front tooth for the large physique P(L). The turning of the mechanical turning axis X1 with a radius r(L2) about the center A of the imaging region R, the separation distance D(L2) (magnification m(L2)), and the regulation width W(L2) are associated with the case where the position of the imaging region R is the molar tooth for the large physique P(L).

Based on the case where the position of the imaging region is the molar tooth for the normal physique P(M), the separation distance D(M2) that is smaller one of the distance between the X-ray generator 126 and the center A of the imaging region R and the distance between the X-ray detector 128 and the center A of the imaging region R can be minimized as described in the second embodiment. As described in the second embodiment, assuming that the mechanical turning axis X1 is closer to the X-ray detector 128 than the X-ray generator 126, the magnification m(M2) can be set to the smallest one, and the width W(M2) can be set to the smallest one.

On the other hand, in the case where the position of the imaging region is the front tooth for the normal physique P(M), the maximum distance LD increases as described in the second embodiment. For this reason, the separation distance D(M1) is increased larger than the separation distance D(M2) by turning the mechanical turning axis X1 with the radius r(M1) about the center A of the imaging region R. It is necessary to set the magnification m(M1) larger than the magnification m(M2), and to set the regulation width W(M1) larger than the regulation width W(M2).

It is assumed that the position of the imaging region is the molar tooth for the large physique P(L). In this case, in order not to contact with the head P having the large physique P(L), the mechanical turning axis X1 is turned with the radius r(L2) about the center A of the imaging region R, whereby it is necessary to set the separation distance D(L2) larger than the separation distance D(M2). It is also necessary to set the magnification m(L2) larger than the magnification m(M2), and to set the regulation width W(L2) larger than the regulation width W(M2).

Assuming the case where the position of the imaging region is the front tooth for the large physique P(L), in order not to contact with the head P having the large physique P(L), the mechanical turning axis X1 is turned with the radius r(L1) about the center A of the imaging region R. At this time, it is necessary to set the separation distance D(L1) larger than the separation distance D(M1) by setting the radius r(L1) larger than the radius r(M1). It is also necessary to set the magnification m(L1) larger than the magnification m(M1), and to set the regulation width W(L1) larger than the regulation width W(M1).

In step S27, the X-ray regulating unit 129 is controlled according to the regulation widths W(M1), W(M2), W(L1), W(L2) that are the decided regulation amount, and the X-ray detector 128 emits the X-ray having the width corresponding to the imaging region R.

In step S28, the CT imaging is performed by controlling the turning based on the decided turning control content. The turning control is one in which the size of the physique of the head P is considered in the turning control described in the second embodiment.

Figure 22:
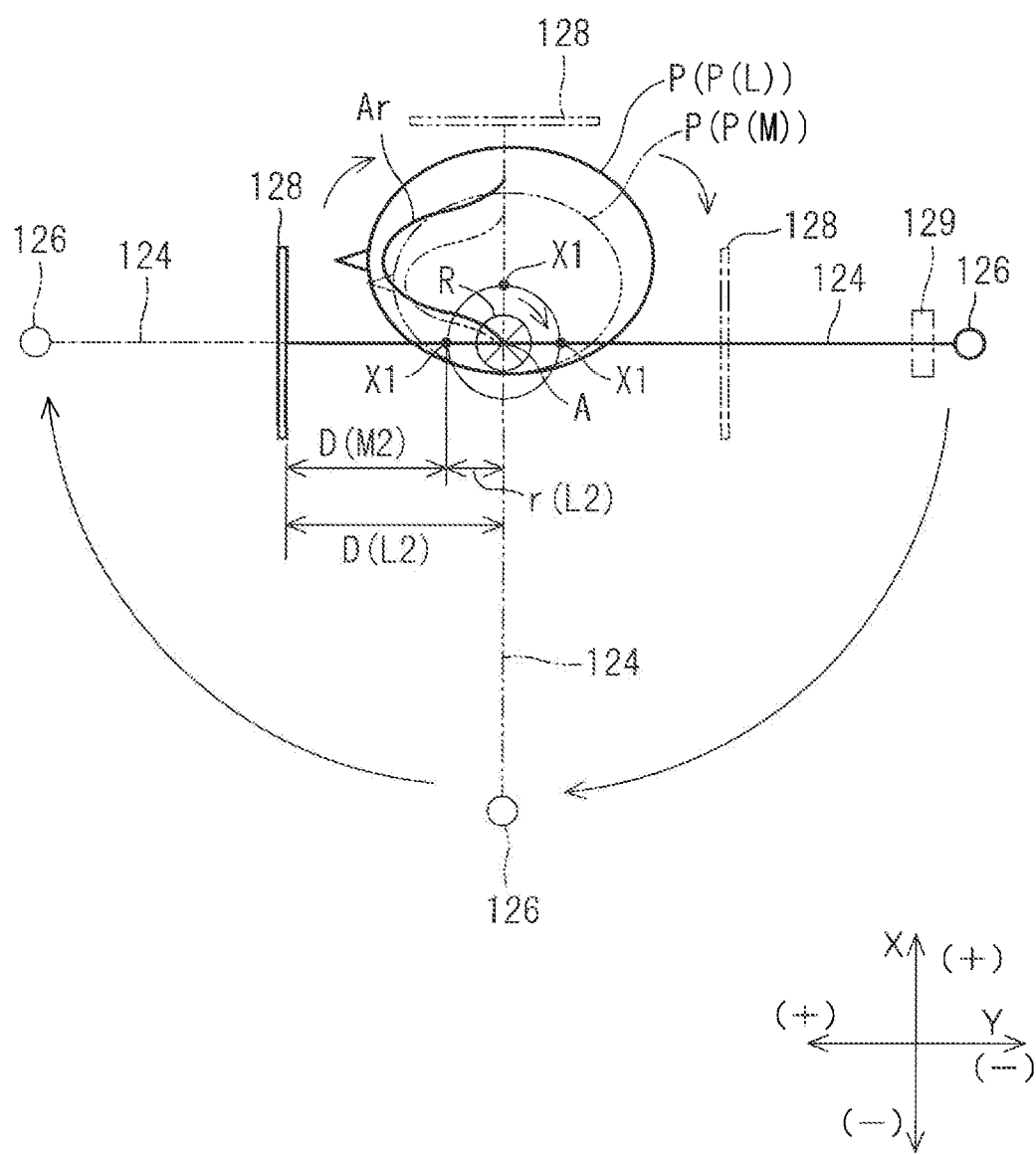
FIG. 22 is a view illustrating an example of the turning operation.

The turning operation based on the turning control will be described more specifically with reference to FIGS. 22 and 23.

First, it is assumed that the turning operation in the case of the normal physique P(M) is as described in FIGS. 10 and 11 in the second embodiment.

That is, the case where the position of the imaging region R is the molar tooth for the normal P(M) is considered. In this case, when the turning support 124 is turned while the mechanical turning axis X1 is matched with the center A of the imaging region R, the X-ray generator 126 and the X-ray detector 128 can turn about the imaging region R without contacting with the head P (see FIG. 10). In this case, the separation distance D(M2) matches the distance between the mechanical turning axis X1 and the X-ray detector 128.

In the case where the position of the imaging region R is the molar tooth for the large physique P(L), the X-ray generator 126 or the X-ray detector 128 possibly contacts with the head P when the turning support 124 is turned while the mechanical turning axis X1 is aligned with the center A of the imaging region R. For this reason, as illustrated in FIG. 22, the X-ray detector 128 turns on a further outer circumferential side with respect to the center A of the imaging region R.

At this point, as defined in the above reference table, the mechanical turning axis X1 is turned with the radius r(L2) about the center A of the imaging region R. Consequently, based on the separation distance D(M2) (see the separation distance D(2) in FIG. 10, the separation distance D(M2) is equal to the distance between the center A of the imaging region R and the mechanical turning axis X1), the separation distance D(L2) becomes the separation distance in which the radius r(L2) is added to the separation distance D(M2), and is larger than the separation distance D(M2). Thus, the magnification m(L2) is larger than the magnification m(M2). As can be seen from FIG. 22, the imaging region R comes close to the side of the X-ray generator 126, and it is necessary to set the regulation width W(L2) larger than the regulation width W(M2).

In the case where the position of the imaging region R is the front tooth for the normal physique P(M), the mechanical turning axis X1 is turned with the radius r(M1) about the center A of the imaging region R (see FIG. 11). In this case, based on the separation distance D(M2) (referred to as the separation distance D(2) in FIG. 10, the separation distance D(M2) is equal to the distance between the center A of the imaging region R and the mechanical turning axis X1), the distance D(M1) between the center A of the imaging region R and the X-ray detector 128 becomes the distance in which the radius r(M1) is added to the separation distance D(M2). Even when the position of the imaging region R is the front tooth for the large physique P(L), the X-ray generator 126 or the X-ray detector 128 possibly contacts with the head P when being turned by the same turning operation. For this reason, as illustrated in FIG. 23, the X-ray detector 128 turns on the further outer circumferential side with respect to the center A of the imaging region R.

At this point, as defined in the above reference table, the mechanical turning axis X1 is turned with the radius r(L1) about the center A of the imaging region R. The radius r(L1) is set larger than the radius r(M1). In this case, based on the separation distance D(M2) (referred to as the separation distance D(2) in FIG. 10, the separation distance D(M2) is equal to the distance between the center A of the imaging region R and the mechanical turning axis X1), the separation distance D(L1) becomes the separation distance in which the radius r(L1) is added to the separation distance D(M2), and is larger than the separation distance D(M1). Thus, the magnification m(L1) is larger than the magnification m(M1). As can be seen from FIG. 23, the imaging region R comes close to the side of the X-ray generator 126, and it is necessary to set the regulation width W(L1) larger than the regulation width W(M1).

The X-ray image data necessary for generating the X-ray CT image of the imaging region R of the local part of the dental arch is obtained by turning the X-ray generator 126 and the X-ray detector 128 about the imaging region R of the head P, and the X-ray CT image is generated based on the obtained X-ray image data.

At this point, the description of the configuration in which the turning support 124 is turned while the mechanical turning axis X1 is matched with the center A of the imaging region will be supplemented.

When that the turning support 124 is turned with the mechanical turning axis X1 matched with the center A of the imaging region (see FIG. 10) and that the turning support 124 is turned while the mechanical turning axis X1 is turned with the radius r about the center A of the imaging region (see FIG. 11) are considered while compared to each other, that the turning support 124 is turned with the mechanical turning axis X1 matched with the center A of the imaging region can be regarded as the case where the radius of the circular movement of the mechanical turning axis X1 by the turning axis moving mechanism 134 has a value of zero. When the radius of the circular movement is referred to as a radius r(M2), a relationship of radius r(M1)>radius r(M2) holds between the radius r(M1) and the radius r(M2) for the configuration, in which the radius r(M2)=0 and the mechanical turning axis X1 is located closer to the X-ray detector 128 than the center position between the X-ray generator 126 and the X-ray detector 128.

On the other hand, the processing proceeds to step S29 when the X-ray CT imaging targeting the whole of the dental arch is determined to be selected in step S22.

The input setting of the physique is received in step S29, and the physique is set based on the received physique in step S30. Steps S29 and S30 are the same as steps S23 and S24.

In step S31, the turning control content and the regulation amount are decided according to the set physique. The turning control content and the regulation amount are expressed in the same manner as described in the second embodiment.

That is, when the X-ray CT imaging targeting the whole of the dental arch is selected, the center A of the imaging region R with respect to the head P is kept constant. However, in the case where the physique of the head P is different, the X-ray generator 126 or the X-ray detector 128 is in danger of the contact with the head P when the physique is large. When the trajectories of the X-ray generator 126 and the X-ray detector 128 are set according to the large physique, for example, the X-ray detector 128 is separated far away from the imaging region R, and the clear image is hardly obtained. For this reason, the turning control content and the regulation amount are decided according to the set physique.

For example, the turning control content and the regulation amount according to the physique can be decided by referring to the reference table in FIG. 21. That is, the reference table in which the turning control content, the separation distance D (magnification m), and the regulation width W are correlated with the physique is previously registered.

In the example of FIG. 21, that the mechanical turning axis X1 is turned while matched with the center A of the imaging region R, the separation distance D(M) (magnification m(M)), and the regulating width W(M) are associated with the normal physique P(M) as the turning control content. For the physique P(L) larger than the normal physique P(M), the mechanical turning axis X1 is turned with a radius r about the center A of the imaging region R, the separation distance D(L) (magnification factor m(L)), and a regulating width W(L) are correlated with one another as the turning control content. Specific numerical values are specified as the separation distance D(M), the magnification m(M), the regulation width W(M), the separation distance D(L), the magnification m(L), the regulation width W(L), and the radius r. Separation distance D(M)<separation distance D(L), magnification m(M)<magnification m(L), regulation width W(M)<regulation width W(L) hold because the physique P(L) is larger than the physique P(M).

In step S32, the X-ray regulating unit 129 is controlled according to the regulation widths W(M), W(L) corresponding to the decided regulation amount, and the X-ray generator 126 emits the X-ray having the width corresponding to the imaging region R.

In step S33, the CT imaging is performed by controlling the turning based on the decided turning control content. When the X-ray CT imaging is performed by irradiating the head P with the X-ray generated from the X-ray generator 126 and the movement of the mechanical turning axis X1 is needed, the turning axis moving mechanism 134 moves the mechanical turning axis X1 in synchronization with the turning of the turning support 124 about the mechanical turning axis X1 using the turning mechanism 132, and the turning support 124 is caused to perform the combined motion, which allows the X-ray generator 126 and the X-ray detector 128 to be turned about the center A of the imaging region R. When the mechanical turning axis X1 is matched with the center A of the imaging region R, the turning mechanism 132 turns the turning support 124 about the mechanical turning axis X1 while the mechanical turning axis X1 is fixed to the position of the center A of the imaging region R. Consequently, when the X-ray generator 126 and the X-ray detector 128 are turned about the center A of the imaging region R, the position of the mechanical turning axis X1 with respect to the center A of the imaging region R is changed according to the physique P(M) or the physique P(L) of the head P set by the physique setting unit 251a such that the separation distance D(L) in the case where the set physique is the first physique P(L) is larger than the separation distance D(M) in the case where the set physique is the second physique P(M) small than the first physique P(L). In the second embodiment, the mechanical turning axis X1 turns about the center A of the imaging region R while the positional relationship provided between the center A of the imaging region R and the X-ray detector 128 is maintained.

In this case, for the relatively large first physique P(L), when the X-ray CT imaging is performed by irradiating the head P with the X-ray generated from the X-ray generator 126, the turning axis moving mechanism 134 rotates the mechanical turning axis X1 about the center A of the imaging region R in synchronization with the turning of the turning support 124 about the mechanical turning axis X1 using the turning mechanism 132.

Figure 24:
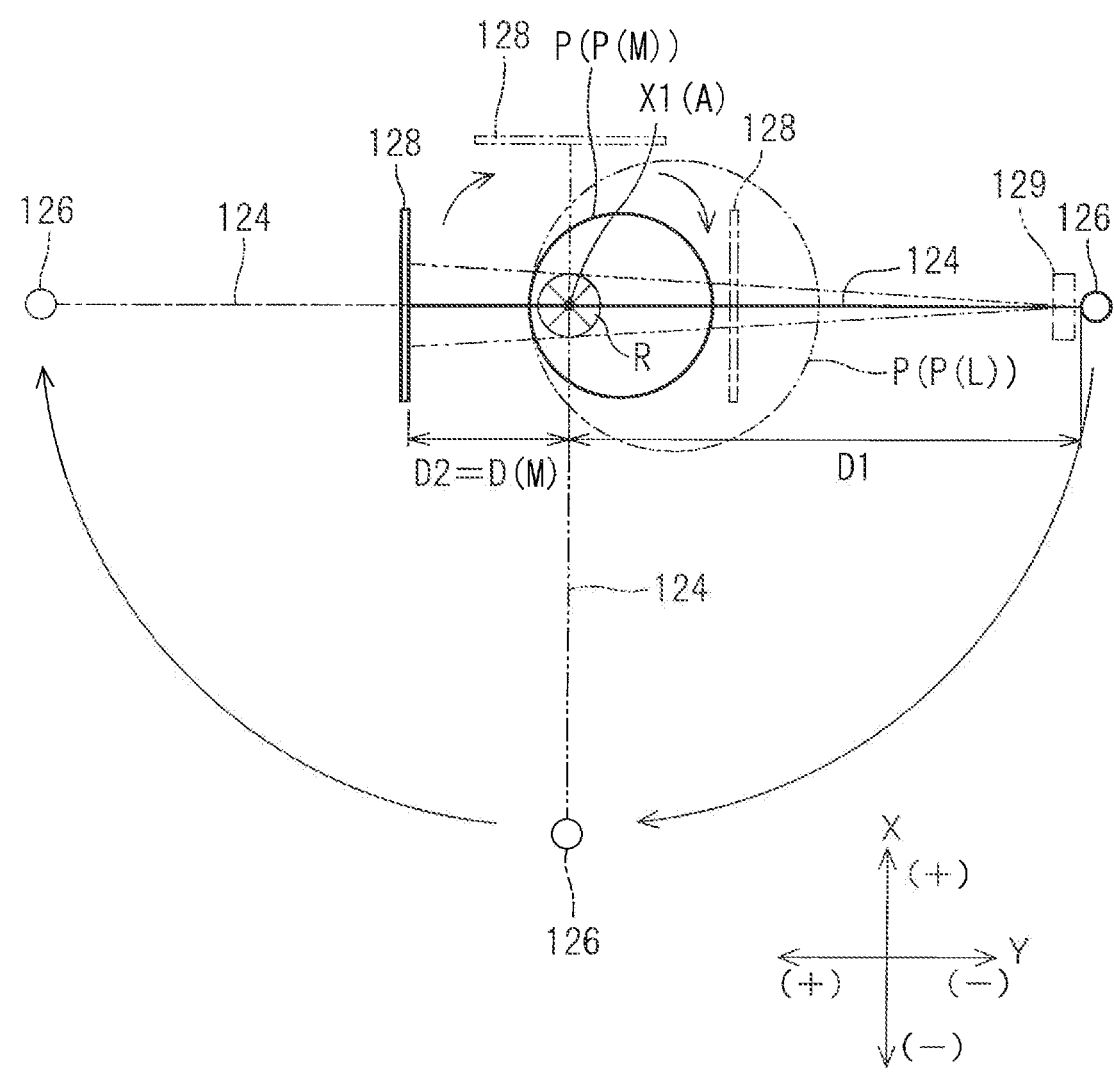
FIG. 24 is a view illustrating an example of the turning operation.
Figure 25:
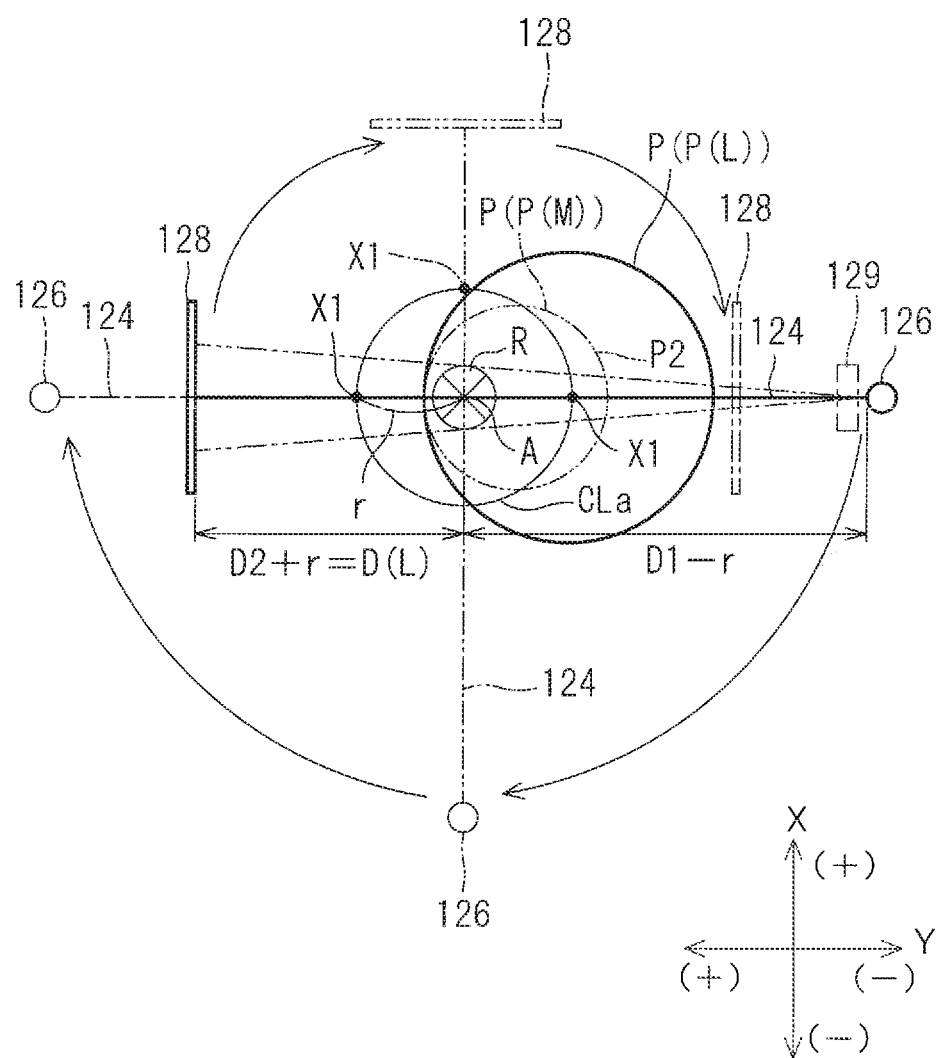
FIG. 25 is a view illustrating an example of the turning operation.

The turning operation will be described more specifically with reference to FIGS. 24 and 25. FIG. 24 is an explanatory view illustrating the turning operation for the relatively small second physique P(M), and FIG. 25 is an explanatory view illustrating the turning operation for the relatively large first physique P(L). For convenience, FIGS. 24 and 25 illustrate the range in which the turning support 124 is turned by 180 degrees. However, the turning support 124 is rotated by 360 degrees by drawing the same trajectory. The CT imaging may be performed by rotating the turning support 124 by 180 degrees.

For the relatively small second physique P(M), as illustrated in FIG. 24, the turning support 124 is turned while the mechanical turning axis X1 is matched with the center A of the imaging region R. In this case, the X-ray generator 126 and the X-ray detector 128 turn about the mechanical turning axis X1 matched with the center A of the imaging region R. During the turning, the distance between the center A of the imaging region R and the X-ray generator 126 is maintained at D1, and the distance between the center A of the imaging region R and the X-ray detector 128 is maintained at D2. Because the X-ray detector 128 is located closer to the center A of the imaging region R than the X-ray generator 126 on the orbits of the X-ray generator 126 and the X-ray detector 128, which are set for the imaging region R, during the X-ray imaging, the separation distance D(M) becomes the distance D2 between the center A of the imaging region R and the X-ray detector 128. The separation distance D(M) is set larger than the maximum distance between the center A of the imaging region R and the surface of the head P(P2) having the smaller second physique P(M) in the direction orthogonal to the turning axis X1. For this reason, the X-ray detector 128 can turn about the head P(P2) having the smaller second physique P(M) without contacting with the head P(P2). The X-ray generator 126 turns at a position farther from the center A of the imaging region R than the X-ray detector 128, so that the X-ray generator 126 can turn around the head P(P2) without contacting with the head P(P2). The separation distance D (not illustrated) becomes the distance between the center A of the imaging region R and the X-ray generator 126 when the X-ray generator 126 is closer to the imaging center A than the X-ray detector 128 on the orbits of the X-ray generator 126 and the X-ray detector 128, which set for the imaging region R, during the X-ray imaging.

The chin rest 142a is commonly used for the head P having the second physique P(M) and the head P having the first physique P(L). For this reason, in both the heads P, the imaging region R is located at the common position in the front portion of the head, and an occipital region of the head P having the first physique P(L) occupies a larger region on the −Y-side than the head P having the second physique P(M). For the relatively large first physique P(L), when the X-ray detector 128 turns in the same manner as described above, t the X-ray detector 128 possibly abuts on the head P having the first physique P(L).

For this reason, for the relatively large first physique P(L), as illustrated in FIG. 25, the turning support 124 is turned about the mechanical turning axis X1 while the mechanical turning axis X1 is turned with the radius r about the center A of the imaging region R. That is, the mechanical turning axis X1 moves on a circular orbit CLa having the radius r.

That is, the position of the mechanical turning axis X1 with respect to the center A of the imaging region R is changed such that the mechanical turning axis X1 is moved away from the center A of the imaging region R. More specifically, the mechanical turning axis X1 is turned with the radius r about the center A of the imaging region R by the turning axis moving mechanism 134 in synchronization with the turning of the turning support 124 about the mechanical turning axis X1 using the turning mechanism 132. In order to move the X-ray detector 128 away from the center A of the imaging region R, the mechanical turning axis X1 is shifted to the side of the X-ray detector 128. That is, the mechanical turning axis X1 turns about the center A of the imaging region R while being provided between the center A of the imaging region R and the X-ray detector 128.

In this case, the X-ray generator 126 and the X-ray detector 128 turn about the mechanical turning axis X1. When the distance D1 in FIG. 24 is a reference, the distance between the center A of the imaging region R and the X-ray generator 126 during the turning is distance D1−radius r, and is kept constant. When the distance D2 in FIG. 24 is a reference, the distance between the center A of the imaging region R and the X-ray detector 128 during the turning is distance D2+radius r, and is kept constant. The smaller one becomes the separation distance D(L). At this point, it is assumed that the radius r is decided within the range of (distance D1−radius r)≥(distance D2+radius r). For this reason, the separation distance D(L) is distance D2+radius r. The separation distance D(L) is set larger than the maximum distance between the center A of the imaging region R and the surface of the head P having the larger first physique P(L) in the direction orthogonal to the turning axis X1. Consequently, the X-ray detector 128 can turn about the head P having the larger first physique P(L) without contacting with the head P. The X-ray generator 126 turns at a position as far as or far away from the X-ray detector 128 with respect to the center A of the imaging region R, so that the X-ray generator 126 can turn around the head P without contacting with the head P.

In the example of FIG. 25, during the X-ray CT imaging, a bias of the mechanical turning axis X1 with respect to the center A is generated on the side of the X-ray detector 128. The direction from the center A toward the mechanical turning axis X1 and the direction from the X-ray generator 126 toward the X-ray detector 128 are maintained in parallel.

When the relatively small second physique P(M) in FIG. 24 is compared to the relatively large first physique P(L) in FIG. 25, the relatively small second physique P(M) is smaller than the relatively large first physique P(L) in the distance between the center A of the imaging region R and the X-ray detector 128. For this reason, in order that the X-rays emitted from the X-ray generator 126 passes through the whole of the imaging region R, the regulating width W(M) of the X-ray by the X-ray regulating unit 129 for the second physique P(M) may be set larger than the regulating width W(L) of the X-ray by the X-ray regulating unit 129 for the first physique P(L). Consequently, the X-ray can be emitted in the range corresponding to the imaging region R. That is, when the X-ray generator 126 and the X-ray detector 128 are rotated about the center A of the imaging region R, the regulation widths W(L), W(M) are set according to the distance between the X-ray generator 126 and the center A of imaging region R. The X-ray regulating unit 129 adjusts the regulation amount of the X-ray generated from the X-ray generator 126 according to the distance.

In the regulation width W of the X-ray by the X-ray regulating unit 129, only a regulation width Wx in the x-direction may be adjusted, and a regulation width Wy in the y-direction may also be adjusted.

The X-ray image data necessary for generating the X-ray CT image of the imaging region R targeting the whole of the dental arch is obtained by turning the X-ray generator 126 and the X-ray detector 128 about the imaging region R of the head P, and the X-ray CT image is generated based on the obtained X-ray image data.

<Effect>

With the X-ray CT imaging apparatus 210 of the third embodiment, the same operation and effect as those of the X-ray CT imaging apparatus 110 of the second embodiment can be obtained.

Additionally, the position of the turning axis X1 is controlled according to the size of the physique of the subject (head P) set by the physique setting unit 251a. In this case, the position of the mechanical turning axis X1 with respect to the center A of the imaging region R is changed such that the separation distance D for the large physique is larger than the separation distance D for the small physique of the subject. Consequently, the X-ray generator 126 and the X-ray detector 128, which turn about the subject, can be prevented from contacting with the subject. The turning trajectory of the X-ray detector 128 is changed according to the size of the physique, so that the X-ray CT imaging can be performed by bringing the X-ray detector 128 as close as possible to the head P while the contact between the X-ray detector 128 and the head P is prevented. Consequently, the clear X-ray image can be generated.

In the case where the CT imaging is performed on the whole of the dental arch, the position of the mechanical turning axis X1 with respect to the center A of the imaging region R is changed such that when the physique of the subject is the second physique P(M), the mechanical turning axis X1 is matched with the position of the center A of the imaging region R, and when the physique of the subject is the first physique P(L), the position of the mechanical turning axis X1 is separated from the center A of the imaging region R. Consequently, the separation distance D can be increased for the large first physique P(L).

When the X-ray CT imaging is performed on the local part or whole of the dental arch, the turning axis moving mechanism 134 moves the mechanical turning axis X1 in synchronization with the turning of the turning support 124 about the mechanical turning axis X1 using the turning mechanism 132, and the turning support 124 is caused to perform the combined motion, which allows the X-ray generator 126 and the X-ray detector 128 to turn about the center A of the imaging region R. At this point, the turning axis moving mechanism 134 rotates the mechanical turning axis X1 about the center A of the imaging region R, so that the X-ray generator 126 and the X-ray detector 128 can be turned along the orbit as close as possible to a circle even if the mechanical turning axis X1 is move during the performance of the X-ray CT imaging.

While the X-ray CT imaging is performed by irradiating the subject with the X-ray generated from the X-ray generator 126, each of the distance between the X-ray generator 126 and the center A of the imaging region R and the distance between the X-ray detector 128 and the center A of the imaging region R is kept constant, and the X-ray CT imaging can be performed.

<Modifications>

In the third embodiment, the position of the mechanical turning axis X1 with respect to the center A of the imaging region R is changed according to the set physique when the CT imaging is performed on the local part of the dental arch and when the X-ray CT imaging is performed on the whole of the dental arch. However, the position of the mechanical turning axis X1 is not necessarily changed according to the set physique. Only when the CT imaging is performed on the local part of the dental arch, the position of the mechanical turning axis X1 with respect to the center A of the imaging region R may be changed according to the set physique. In this case, only when the CT imaging is performed on a specific tooth of the dental arch (for example, the front tooth or the molar tooth), the position of the mechanical turning axis X1 with respect to the center A of the imaging region R may be changed according to the set physique. Only when the X-ray CT imaging is performed on the whole of the dental arch, the position of the mechanical turning axis X1 with respect to the center A of the imaging region R may be changed according to the set physique.

The description has been made mainly on that the turning trajectories of the X-ray generator and the X-ray detector are changed when the CT imaging is performed on the first physique and the second physique smaller than the first physique. Alternatively, the turning trajectories of the X-ray generator and the X-ray detector may be changed according to the sizes of at least three physiques. Alternatively, the turning trajectories of the X-ray generator and the X-ray detector may continuously be changed according to the setting of the continuous size of the physique. In any case, the turning trajectories of the X-ray generator and the X-ray detector may be controlled as in each of the above examples when the sizes of two physiques are assumed.

<Modifications>

In each of the above embodiments and each of modifications, the X-ray generator and the X-ray detector have the circular turning orbit. Alternatively, the X-ray generator and the X-ray detector may turn while drawing an elliptical trajectory or a trajectory in which the circle and the ellipse are combined.

The description has been made on that in each of the above embodiments and modifications, the positions of the two imaging regions are different, and the turning trajectories of the X-ray generator and the X-ray detector are changed according to the positions of the two imaging regions. Alternatively, the turning trajectory of the X-ray generator and the X-ray detector may be changed according to the positions of at least three imaging regions. Alternatively, the turning trajectories of the X-ray generator and the X-ray detector may continuously be changed according to the difference of the continuous position of the imaging region. In any case, the turning trajectories of the X-ray generator and the X-ray detector may be controlled as in each of the above examples when the two imaging regions having the different positions are compared to each other.

In each of the above embodiments and modifications, the description is made on the assumption of the normal scan in which the whole of the imaging region R is irradiated with the X-ray. However, the above embodiments and modifications can also be applied to the case where offset scan in which the region, which is narrower than the imaging region and shifted from the center of the imaging region, is irradiated with the X-ray.

In the X-ray CT imaging apparatus of the present invention, each of the embodiments and modifications may independently be provided. Alternatively, the embodiments and modifications may be combined as long as inconsistency is not generated. The application to different local parts of the same head and the application to each local part of a plurality of subjects having different sizes can be cited as an example of both the second embodiment and the third embodiment.

Regarding the configuration in which the turning support 124 is turned while the mechanical turning axis X1 is turned about the center A of the imaging region, as described above, in the present invention, the radius can be switched or changed between large and small for the radius of the orbit of the circular movement of the mechanical turning axis X1.

Assuming that the radius r(n) is the value of the radius, the relationship of the radius r(n1)>the radius r(n2) can be switched or changed.

The radius r(n2) includes the case where the radius r(M2) has a value of zero, and also includes the case of the radius larger than zero.

An intermediate radius r(nm) having a relationship of radius r(n1)>radius r(nm) >radius r(n2) is defined between the radius r(n1) and the radius r(n2), the radius r(n1), the radius r(nm), and the radius r(n2) may be switched or changed according to the position of the imaging region R, and a plurality of intermediate radii r(nm) may be decided from small to large.

A configuration, such as a configuration in which a coordinate is calculated after the position of the imaging region R is designated, in which the radius r(n2) to the radius r(n1) may steplessly be decided.

The radius r(n2), the radius r(nm), and the radius r(n1) may be applied to the same head according to the position of the imaging region R, or applied according to the position of the imaging region R among the heads having different physiques.

An example in which aspects of the present invention or constituent elements of the present application are expressed in another language will be described.

The horizontal arm 123 may be referred to as a support beam 123.

The turning support 20 and the turning support 124 may be referred to as a rotational supporter 20 and a rotational supporter 124, respectively. The turning support 20 and the turning support 124 may simply be referred to as a supporter 20 and a supporter 124, respectively.

The arm body 124a may be regarded as the main supporter 124a, and the hanging support 124b may be regarded as the sub-supporter 124b.

The head fixing apparatus arm 141 may be referred to as a head support beam 141.

The head fixing apparatus 142 may be referred to as a head supporter 142.

The member forming the X-ray regulating hole of the X-ray regulating unit 129 is a shield.

The shaft 33 and the shaft 124 may be referred to as a shaft 33 and a shaft 124c, respectively.

The mechanical turning axis X1 may be referred to as a mechanical rotation axis X1.

The turning drive mechanism 30 and the turning drive mechanism 130 may be referred to as a rotational movement drive apparatus 30 and a rotational movement drive apparatus 130, respectively. The turning drive mechanism 30 and the turning drive mechanism 130 may be referred to as a rotational movement driver 30 and a rotational movement driver 130, respectively.

The turning axis moving mechanism 38 and the turning axis moving mechanism 134 may be referred to as a rotation axis moving apparatus 38 and a rotation axis moving apparatus 134, respectively. The turning axis moving mechanism 38 and the turning axis moving mechanism 134 may be referred to as a rotation axis driver 38 and a rotation axis driver 134, respectively.

The turning mechanism 32 and the turning mechanism 132 may be referred to as a rotation apparatus 32 and a rotation apparatus 132, respectively. The turning mechanism 32 and the turning mechanism 132 may be referred to as a rotation driver 32 and a rotation driver 132, respectively. The turning mechanism 32 and the turning mechanism 132 may be referred to as a rotary 32 and a rotary 132, respectively.

The information processing main body 182 also functions as a controller for the X-ray image processing apparatus 180.

The main body controller 150 includes a CPU 151, the information processing main body 182 that is the controller includes a CPU 183, and the CPU 151 and the CPU 183 are processors.

The main body controller 150 and the information processing main body 182 are constructed with circuits.

The imaging region position setting unit 151a is a component of the CPU 151 that works when executing the setting of the imaging region position. More particularly, the imaging region position setting unit 151a is a circuit element of the CPU 151.

The imaging region position setting unit 40 has the same configuration as the imaging region position setting unit 151a.

The turning controller 151b and the turning controller 251b are components of the CPU 151 that works when executing the turning control. More particularly, the imaging region position setting unit 151a is a circuit element of the CPU 151.

The turning controller 60 has the same configuration as the turning controller 151b.

The subject physique setting unit 251a is a component of the CPU 151 that works when executing the turning control. More particularly, the imaging region position setting unit 151a is a circuit element of the CPU 151.

The image output unit 156 and the image output unit 188a may be referred to as an image output circuit 156 and an image output circuit 188a, respectively.

The operation input unit 155 and the operation input unit 189a may be referred to as an operation input circuit 155 and an operation input circuit 189a, respectively.

The operation panel apparatus 158 functions as the operating unit. The operation panel apparatus 158 and the operating unit 189 are configured to receive the physical operations, such as a mouse, a keyboard, a voice detector, and a gesture detector. The operation panel apparatus 158 and the operating unit 189 may be regarded as a physical interface 158 and a physical interface 189, respectively.

The input and output unit 154a, the input and output unit 154b, and the input and output unit 186 may be referred to as an input and output circuit 154a, an input and output circuit 154b, and an input and output circuit 186, respectively.

As described above, the present invention can also be expressed as follows.

<First Aspect>

An X-ray CT imaging apparatus comprising: a supporter that supports an X-ray generator and an X-ray detector such that the X-ray generator and the X-ray detector are opposed to each other with a subject sandwiched therebetween; a rotational movement driver including a rotation driver that turns the supporter about a mechanical rotation axis located between the X-ray generator and the X-ray detector and a rotation axis driver that moves the mechanical rotation axis in a direction intersecting with an axial direction of the mechanical rotation axis; and a processor that receives a setting of a position of an X-ray CT imaging region with respect to a local part of a dental arch of a head of the subject and controls the rotation driver and the rotation axis driver. The rotation axis driver moves the mechanical rotation axis in synchronization with turning of the supporter about the mechanical rotation axis using the rotation driver, and the supporter is caused to perform combined motion, which allows the X-ray generator and the X-ray detector to turn about the X-ray CT imaging region, and a position of the mechanical rotation axis is controlled according to the set position of the X-ray CT imaging region.

<Second Aspect>

In the X-ray CT imaging apparatus of the first aspect, when X-ray CT imaging is performed on a molar tooth of the dental arch as the X-ray CT imaging region, the position of the mechanical rotation axis is controlled such that the X-ray detector passes through a trajectory closer to a center of the X-ray CT imaging region than the X-ray detector during the performance of the X-ray CT imaging on a front tooth of the dental arch as the X-ray CT imaging region.

<Third Aspect>

In the X-ray CT imaging apparatus of the first aspect, drive control in which the supporter is caused to perform the combined motion and drive control in which the supporter is turned while the mechanical rotation axis is fixed to the position of the center of the X-ray CT imaging region are switched according to the set position of the X-ray CT imaging region.

<Fourth Aspect>

In the X-ray CT imaging apparatus of the third aspect, drive control in which the supporter is caused to perform the combined motion when X-ray CT imaging is performed on a front tooth of the dental arch as the X-ray CT imaging region, and drive control in which the supporter is turned while the mechanical rotation axis is fixed to the position of the center of the X-ray CT imaging region when X-ray CT imaging is performed on a molar tooth of the dental arch as the X-ray CT imaging region.

<Fifth Aspect>

In the X-ray CT imaging apparatus of the first aspect, a distance between the mechanical rotation axis and the center of the X-ray CT imaging region is changed according to the set position of the X-ray CT imaging region when the supporter is caused to perform the combined motion.

<Sixth Aspect>

In the X-ray CT imaging apparatus of the first aspect, when X-ray CT imaging is performed on a local part of the dental arch according to the set position of the X-ray CT imaging region, the position of the mechanical rotation axis with respect to the center of the X-ray CT imaging region is changed such that a separation distance is larger than a maximum distance on assumption that smaller one of a distance between the center of the X-ray CT imaging region and the X-ray generator and a distance between the center of the X-ray CT imaging region and the X-ray detector is set to the separation distance, and that the maximum distance between a surface of the head and the center of the X-ray CT imaging region is set in a turning range of the X-ray generator or the X-ray detector closer to the center of the X-ray CT imaging region.

<Seventh Aspect>

In the X-ray CT imaging apparatus of the sixth aspect, the processor can receive a first imaging region and a second imaging region where the maximum distance is smaller than the maximum distance of the first imaging region as the X-ray CT imaging region, and according to the set position of the X-ray CT imaging region, the position of the mechanical rotation axis with respect to the center of the X-ray CT imaging region is changed such that the separation distance when the X-ray CT imaging region is the first imaging region is larger than the separation distance when the X-ray CT imaging region is the second imaging region.

<Eighth Aspect>

In the X-ray CT imaging apparatus of the seventh aspect, drive control in which the supporter is caused to perform the combined motion is performed when the X-ray CT imaging region is the first imaging region, and drive control in which the supporter is turned while the mechanical rotation axis is fixed to the position of the center of the X-ray CT imaging region is performed when the X-ray CT imaging region is the second imaging region.

<Ninth Aspect>

In the X-ray CT imaging apparatus of the first aspect, the mechanical rotation axis is set at a position closer to the X-ray detector than the X-ray generator.

<Tenth Aspect>

In the X-ray CT imaging apparatus of the first aspect, the processor performs a subject physique setting capable of setting a first physique and a second physique smaller than the first physique as a setting of a size of the physique of the subject, and controls the position of the mechanical rotation axis according to the size of the set physique of the subject.

<Eleventh Aspect>

In the X-ray CT imaging apparatus of the tenth aspect, drive control in which the supporter is caused to perform the combined motion and drive control in which the supporter is turned while the mechanical rotation axis is fixed to the position of the center of the X-ray CT imaging region are switched according to the size of the set physique of the subject.

<Twelfth Aspect>

In the X-ray CT imaging apparatus of the tenth aspect, a distance between the mechanical rotation axis and the center of the X-ray CT imaging region is changed according to the size of the set physique of the subject when the supporter is caused to perform the combined motion.

<Thirteenth Aspect>

In the X-ray CT imaging apparatus of the first aspect, when the supporter is caused to perform the combined motion, the rotation axis driver rotates the mechanical rotation axis about the center of the X-ray CT imaging region in synchronization with the turning of the supporter about the mechanical rotation axis using the rotation driver.

<Fourteenth Aspect>

The X-ray CT imaging apparatus of the first aspect, the distance of the X-ray generator to the center of the X-ray CT imaging region and the distance of the X-ray detector to the center of the X-ray CT imaging region are kept constant while the X-ray CT imaging is performed by irradiating the subject with an X-ray generated from the X-ray generator.

<Fifteenth Aspect>

A method of controlling an X-ray CT imaging apparatus including: a supporter that supports an X-ray generator and an X-ray detector such that the X-ray generator and the X-ray detector are opposed to each other with a subject sandwiched therebetween; a rotational movement driver including a rotation driver that turns the supporter about a mechanical rotation axis located between the X-ray generator and the X-ray detector and a rotation axis driver that moves the mechanical rotation axis in a direction intersecting with an axial direction of the mechanical rotation axis; and a processor that controls the rotation driver and the rotation axis driver, the method includes: turning the supporter about the mechanical rotation axis using the rotation driver in synchronization with movement of the mechanical rotation axis using the rotation axis driver, and causing the supporter to perform combined motion, which allows the X-ray generator and the X-ray detector to turn about the X-ray CT imaging region; and controlling a position of the mechanical rotation axis according to a setting of the position of the X-ray CT imaging region to a local part of a dental arch of a head of the subject.

Although the present invention is described in detail, the above description is illustrative in all aspects, but the invention is not limited thereto. Innumerable modifications not illustrated can be envisaged without departing from the scope of the present invention.

REFERENCE SIGNS LIST

10, 110, 210: X-ray CT imaging apparatus
20, 124: turning support
22, 126: X-ray generator
24, 128: X-ray detector
30, 130: turning drive mechanism
32, 132: turning mechanism
38, 134: turning axis moving mechanism
40, 151a: imaging region position setting unit
60, 151b, 251b: turning controller
142: head fixing apparatus
150: main body controller
158: operation panel apparatus
158a: display
158b: touch detector
194: imaging region setting image
194a, 194b, 194c, 194d, 194e: imaging region selection image
195: illustration image
195a, 195b: imaging region image
251a: subject physique setting unit
293: physique setting image
293a: normal-size selection image
293b: large-size selection image
A: center
Ar: dental arch
D: separation distance
LD: maximum distance
P: head
P(L): first physique
P(M): second physique
R: X-ray CT imaging region
R(1): first imaging region
R(2): second imaging region
X1: mechanical turning axis

The invention claimed is:

1. An X-ray CT imaging apparatus comprising:
a supporter that supports an X-ray generator and an X-ray detector such that the X-ray generator and the X-ray detector are opposed to each other with a subject sandwiched therebetween;
motors configured to turn the supporter including
a first motor that turns the supporter about a shaft having an axis located between the X-ray generator and the X-ray detector, the axis located closer to the X-ray detector than a center position between the X-ray generator and the X-ray detector, and
a second motor that moves the shaft in a direction intersecting with an axial direction of the shaft; and
a processor that receives a setting of a position of an X-ray CT imaging region with respect to a local part of a dental arch of a head of the subject and controls the first motor and the second motor, wherein the processor allows the second motor to move the shaft in synchronization with turning of the supporter about the shaft using the first motor, and the supporter is caused to perform combined motion, whereby the X-ray generator and the X-ray detector turn about the X-ray CT imaging region, a position of the shaft is controlled according to the set position of the X-ray CT imaging region, and a first distance between the X-ray CT imaging region and the X-ray detector when the X-ray detector passes through a trajectory behind a back of the head during performance of X-ray CT imaging on a molar tooth of the dental arch is smaller than a second distance between the X-ray CT imaging region and the X-ray detector when the X-ray detector passes through a trajectory behind the back of the head during performance of X-ray CT imaging on a front tooth of the dental arch.

2. The X-ray CT imaging apparatus according to claim 1, wherein when the X-ray CT imaging is performed, the position of the shaft is controlled such that the X-ray detector passing behind the back of the head in the X-ray CT imaging on the molar tooth of the dental arch as the X-ray CT imaging region is located closer to a center of the X-ray CT imaging region than the X-ray detector passing behind the back of the head in the X-ray CT imaging on the front tooth of the dental arch as the X-ray CT imaging region.

3. The X-ray CT imaging apparatus according to claim 1, wherein drive control in which the supporter is caused to perform the combined motion and drive control in which the supporter is turned while the axis of the shaft is fixed to the position of the center of the X-ray CT imaging region are switched according to the set position of the X-ray CT imaging region.

4. The X-ray CT imaging apparatus according to claim 3, wherein the drive control in which the supporter is caused to perform the combined motion when the X-ray CT imaging is performed on the front tooth of the dental arch as the X-ray CT imaging region, and drive control in which the supporter is turned while the axis of the shaft is fixed to the position of the center of the X-ray CT imaging region when the X-ray CT imaging is performed on the molar tooth of the dental arch as the X-ray CT imaging region.

5. The X-ray CT imaging apparatus according to claim 1, wherein a distance between the shaft and the center of the X-ray CT imaging region is changed according to the set position of the X-ray CT imaging region when the supporter is caused to perform the combined motion.

6. The X-ray CT imaging apparatus according to claim 1, wherein when X-ray CT imaging is performed on a local part of the dental arch according to the set position of the X-ray CT imaging region, the position of the shaft with respect to the center of the X-ray CT imaging region is changed such that a separation distance is larger than a maximum distance on assumption that smaller one of a distance between the center of the X-ray CT imaging region and the X-ray generator and a distance between the center of the X-ray CT imaging region and the X-ray detector is set to the separation distance, and that the maximum distance between a surface of the head and the center of the X-ray CT imaging region is set in a turning range of the X-ray generator or the X-ray detector closer to the center of the X-ray CT imaging region.

7. The X-ray CT imaging apparatus according to claim 6, wherein the processor is configured to receive a first imaging region and a second imaging region where the maximum distance is smaller than the maximum distance of the first imaging region as the X-ray CT imaging region, and according to the set position of the X-ray CT imaging region, the position of the shaft with respect to the center of the X-ray CT imaging region is changed such that the separation distance when the X-ray CT imaging region is the first imaging region is larger than the separation distance when the X-ray CT imaging region is the second imaging region.

8. The X-ray CT imaging apparatus according to claim 7, wherein drive control in which the supporter is caused to perform the combined motion is performed when the X-ray CT imaging region is the first imaging region, and drive control in which the supporter is turned while axis of the shaft is fixed to the position of the center of the X-ray CT imaging region is performed when the X-ray CT imaging region is the second imaging region.

9. The X-ray CT imaging apparatus according to claim 1, wherein the shaft is set at a position closer to the X-ray detector than the X-ray generator.

10. The X-ray CT imaging apparatus according to claim 1, wherein the processor performs a subject physique setting configured to set a first physique and a second physique smaller than the first physique as a setting of a size of the physique of the subject, and controls the position of the shaft according to the size of the set physique of the subject.

11. The X-ray CT imaging apparatus according to claim 10, wherein drive control in which the supporter is caused to perform the combined motion and drive control in which the supporter is turned while the axis of the shaft is fixed to the position of the center of the X-ray CT imaging region are switched according to the size of the set physique of the subject.

12. The X-ray CT imaging apparatus according to claim 10, wherein a distance between the shaft and the center of the X-ray CT imaging region is changed according to the size of the set physique of the subject when the supporter is caused to perform the combined motion.

13. The X-ray CT imaging apparatus according to claim 1, wherein when the supporter is caused to perform the combined motion, the second motor rotates the shaft about the center of the X-ray CT imaging region in synchronization with the turning of the supporter about the shaft using the second motor.

14. The X-ray CT imaging apparatus according to claim 1, wherein a distance of the X-ray generator to the center of the X-ray CT imaging region and a distance of the X-ray detector to the center of the X-ray CT imaging region are kept constant while the X-ray CT imaging is performed by irradiating the subject with an X-ray generated from the X-ray generator.

15. A method of controlling an X-ray CT imaging apparatus including a supporter that supports an X-ray generator and an X-ray detector such that the X-ray generator and the X-ray detector are opposed to each other with a subject sandwiched therebetween;

a rotational movement driver including
a first motor that turns the supporter about a shaft having an axis located between the X-ray generator and the X-ray detector, the axis located closer to the X-ray detector than a center position between the X-ray generator and the X-ray detector, and
a second motor that moves the shaft in a direction intersecting with an axial direction of the shaft; and a processor that controls the first motor and the second motor, the method comprising:

allowing to turn the supporter about the shaft using the first motor in synchronization with movement of the shaft using the second motor, and causing the supporter to perform combined motion, which allows the X-ray generator and the X-ray detector to turn about an X-ray CT imaging region; and controlling a position of the shaft according to a setting of the position of the X-ray CT imaging region to a local part of a dental arch of a head of the subject, wherein a first distance between the X-ray CT imaging region and the X-ray detector when the X-ray detector passes through a trajectory behind a back of the head during performance of X-ray CT imaging on a molar tooth of the dental arch is smaller than a second distance between the X-ray CT imaging region and the X-ray detector when the X-ray detector passes through a trajectory behind the back of the head during performance of X-ray CT imaging on a front tooth of the dental arch.

* * * * *